(12) United States Patent  
Giovannini et al.

(10) Patent No.: US 8,648,118 B2  
(45) Date of Patent: *Feb. 11, 2014

(54) BICYCLIC RING SYSTEM SUBSTITUTED AMIDE FUNCTIONALISED PHENOLS AS MEDICAMENTS

(75) Inventors: Riccardo Giovannini, Verona (IT); Dieter Hamprecht, Pozzolengo (IT); Barbara Kistler, Pfungstadt (DE); Iain Lingard, Monza (IT)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 47 days.

This patent is subject to a terminal disclaimer.

(21) Appl. No.: 13/324,245

(22) Filed: Dec. 13, 2011

(65) Prior Publication Data

US 2012/0329773 A1 Dec. 27, 2012

(30) Foreign Application Priority Data

Dec. 17, 2010 (EP) .................................... 10195639

(51) Int. Cl.
```
A01N 27/00      (2006.01)
A61K 31/015     (2006.01)
A01N 43/00      (2006.01)
A61K 31/397     (2006.01)
A61K 31/54      (2006.01)
A01N 43/40      (2006.01)
A61K 31/435     (2006.01)
C07D 345/00     (2006.01)
C07D 517/00     (2006.01)
```
(52) U.S. Cl.
USPC .................. 514/764; 514/210.01; 514/222.2; 514/277; 540/1

(58) Field of Classification Search  
None  
See application file for complete search history.

(56) References Cited

U.S. PATENT DOCUMENTS

2004/0097547 A1 5/2004 Taveras et al.

FOREIGN PATENT DOCUMENTS

| WO | 2002057230 A1 | 7/2002 |
| WO | 2008148790 A1 | 12/2008 |
| WO | 2010015613 A1 | 2/2010 |
| WO | 2010063802 A1 | 6/2010 |

OTHER PUBLICATIONS

International Search Report and Written Opinion for PCT/EP2011/073026 mailed Mar. 16, 2012.  
International Search Report and Written Opinion for PCT/EP2011/073025 mailed Mar. 14, 2012.

*Primary Examiner* — Jeffrey S. Lundgren  
*Assistant Examiner* — Michael Schmitt  
(74) *Attorney, Agent, or Firm* — Michael P. Morris; Edward S. Lazer

(57) ABSTRACT

This invention relates to bicyclic ring system substituted amide functionalized phenols of general formula 1,

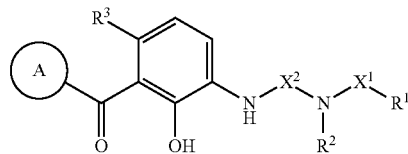

their use as inhibitors of CXCR2 activity, pharmaceutical compositions containing the same, and methods of using the same as agents for treatment and/or prevention of respiratory or gastrointestinal complaints or diseases, inflammatory diseases of the joints, skin, or eyes, diseases of the peripheral or central nervous system or cancers, as well as pharmaceutical compositions which contain these compounds.

11 Claims, No Drawings

BICYCLIC RING SYSTEM SUBSTITUTED AMIDE FUNCTIONALISED PHENOLS AS MEDICAMENTS

FIELD OF THE INVENTION

This invention relates to bicyclic ring system substituted amide functionalized phenols and their use as inhibitors of CXCR2 activity, pharmaceutical compositions containing the same, and methods of using the same as agents for treatment and/or prevention of respiratory or gastrointestinal complaints or diseases, inflammatory diseases of the joints, skin, or eyes, diseases of the peripheral or central nervous system or cancers, as well as pharmaceutical compositions which contain these compounds.

BACKGROUND INFORMATION

WO9625157 discloses acyclic and monocyclic amide functionalized phenolic ureas for use as interleukin-8 receptor antagonists WO0164208 discloses acyclic and monocyclic amide functionalized phenolic squarates for use as interleukin-8 receptor antagonists US20040097547 discloses acyclic and monocyclic amide functionalized phenolic squarates for use as CXC-Chemokine receptor ligands

BRIEF SUMMARY OF THE INVENTION

Cellular movement and placement represents a fundamental property of cells of the immune system. It enables their mobilization and expansion to sites of pathogen challenge. Cell movement is also essential for the complex T cell, B cell and dendritic cell interactions to orchestrate the immune response. For cell migration chemoattractants that signal through seven-transmembrane-G-protein-coupled receptors are of central importance.

The most important facilitators of leukocyte migration are chemoattractant cytokines (chemokines) that bind a large subfamily of the G protein-coupled receptors.

Virtually all cell types, including T and B lymphocytes, natural killer (NK) cells, neutrophils, eosinophils, basophils, dendritic cells (DC) and nonleukocytic cells, such as endothelial cells, fibroblasts, smooth muscle cells, are able to respond to chemotactic stimuli.

Chemokines have been classified into 4 subfamilies based on the presence of cysteines at the N-terminal part of the protein. CXC, CC, CX3C and C. CXC chemokines can be further subclassified into Glutamin-Leucin-Arginine containing (ELR+) and ELR− chemokines (not containing this tripeptide motif). All members of the ELR+ family of chemokines (CXCL1-3 and CXCL5-8) bind to and activate the CXC chemokines receptor 2 (CXCR2), two members (CXCL6 and 8) additionally bind and activate CXCR1. CXCR2 is expressed in the myeloid compartment (e.g. neutrophils, monocytes). It has attracted particular attention, as it has been shown to play a crucial role in the development and promotion of numerous inflammatory diseases and tumor progression.

In many animal models, functional blockade of CXCR2 has been shown to dampen inflammatory processes.

In vitro assays of chemotaxis in general reflect in vivo inflammatory responses and are therefore regarded as correlates of cellular immunity. Therefore it would be desirable to design CXCR2 antagonists that are particularly efficacious in CXCR2 dependent chemotaxis.

The present invention describes low molecular weight bicyclic ring system substituted amide functionalized phenols with CXCR2 antagonist activity. It has been surprisingly found that the compounds of the present invention have a superior efficacy in inhibition of CXCR2 dependent chemotaxis. In addition, compounds of the present invention have been found to have satisfactory pharmacokinetic properties.

DETAILED DESCRIPTION OF THE INVENTION

A compound of formula 1,

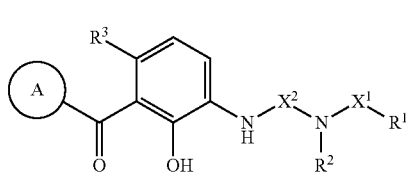

wherein
$R^1$ is an 5-10 membered aromatic, hetero aromatic, non aromatic cyclic or heterocyclic, single or condensed multiring system, optionally substituted by 1-4 residues selected from halogen or $C_{1-6}$-alkyl, optionally substituted with one or more F atoms;
$X^1$ is absent or methylene optionally substituted with $C_{1-5}$-alkyl, said alkyl optionally substituted with one or more F atoms, $C_{1-4}$-alkyl-O—, CN or $C_{3-8}$-cycloalkyl, wherein optionally one carbon atom is replaced by an O;
$R^2$ is H;
$X^2$ is

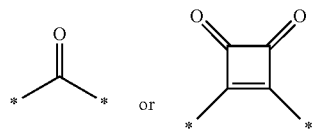

$R^3$ is H, halogen, CN, $C_{1-6}$-alkyl, optionally substituted with one or more F atoms; preferably H or Cl; preferably H;
A is a N-linked 7-13 membered non-aromatic bicyclic system in which the two rings are either condensed to each other or joined in a spiro system and in which if present one CH group can be optionally replaced by N and one, two three or four $CH_2$ groups in said system are optionally replaced by NH, CO, O, S, SO, $SO_2$, and one, two three or four positions on said ring system are optionally substituted with one or more F atoms, $C_{1-6}$-alkyl, optionally substituted with one or more F atoms, $C_{1-6}$-alkyl-OC(O)—, HO—$C_{1-6}$-alkyl- or $C_{1-6}$-alkyl-O—$C_{1-6}$-alkyl- and in which optionally two of these substituents are joined to form an additional ring.
or a pharmaceutically acceptable salt thereof.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like OH, $NH_2$, SO, $SO_2$, CN (cyano), COOH, $CF_3$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

For example, the term "3-carboxypropyl-group" represents the following substituent:

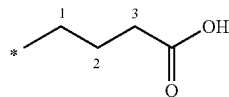

wherein the carboxy group is attached to the third carbon atom of the propyl group. The terms "1-methylpropyl-", "2,2-dimethylpropyl-" or "cyclopropylmethyl-" group represent the following groups:

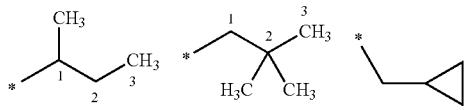

The asterisk may be used in sub-formulas to indicate the bond which is connected to the core molecule as defined.

Many of the followings terms may be used repeatedly in the definition of a formula or group and in each case have one of the meanings given above, independently of one another.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term halogen generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "carbocyclyl" as used either alone or in combination with another radical, means a mono- bi- or tricyclic ring structure consisting of 3 to 14 carbon atoms. The term "carbocycle" refers to fully saturated and aromatic ring systems and partially saturated ring systems. The term "carbocycle" encompasses fused, bridged and spirocyclic systems.

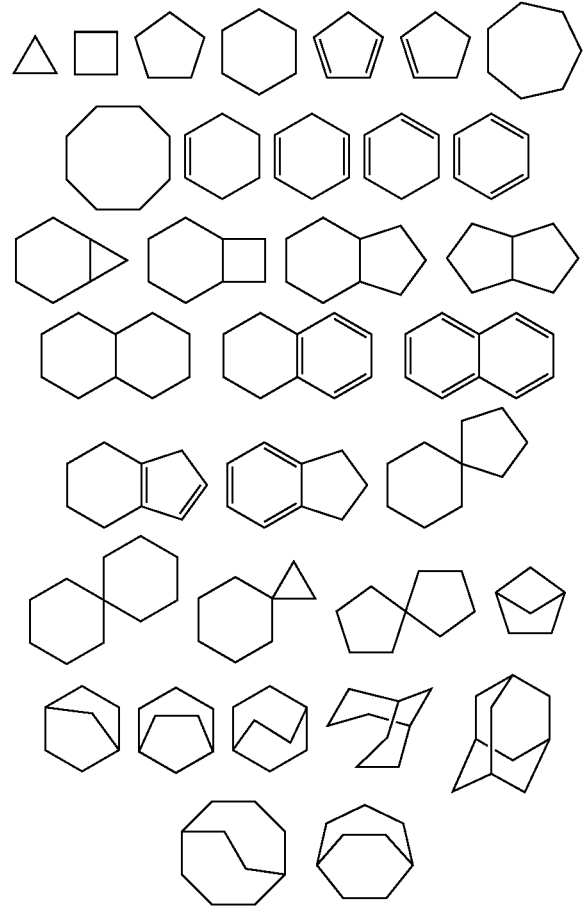

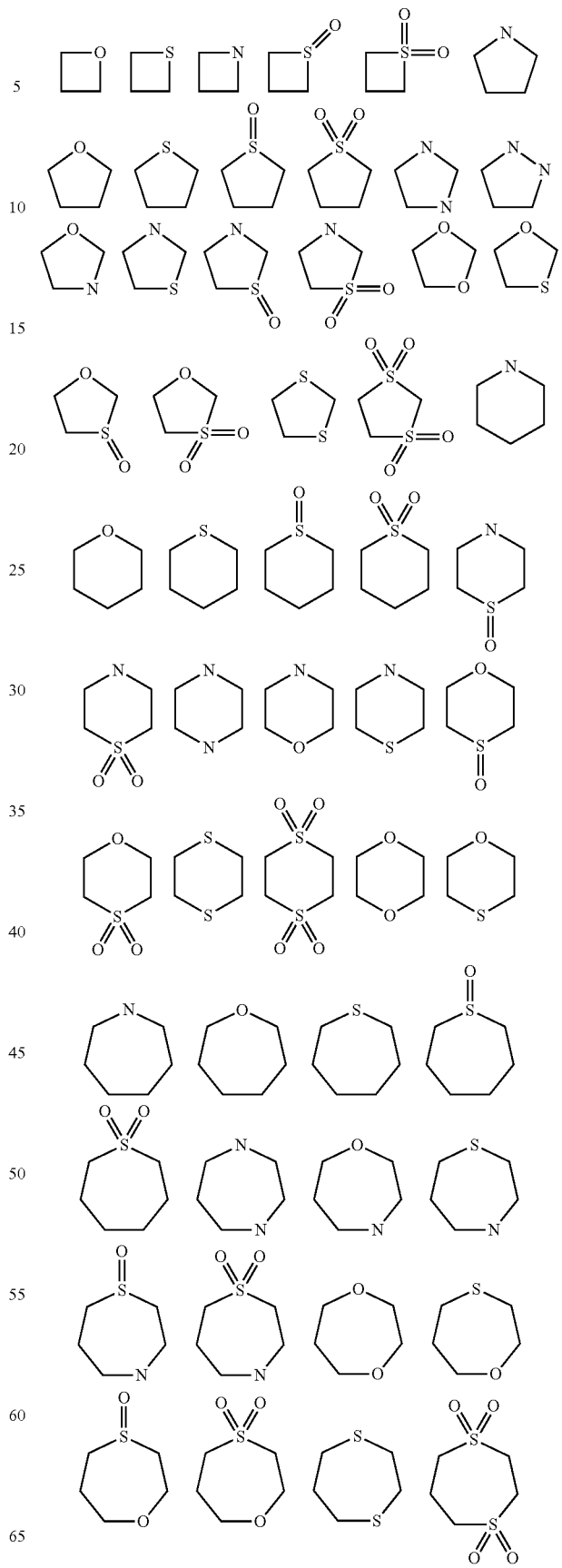

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" means a saturated or unsaturated mono- or polycyclic-ring systems including aromatic ring system containing one or more heteroatoms selected from N, O or $S(O)_r$, wherein r=0, 1 or 2, consisting of 3 to 14 ring atoms wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

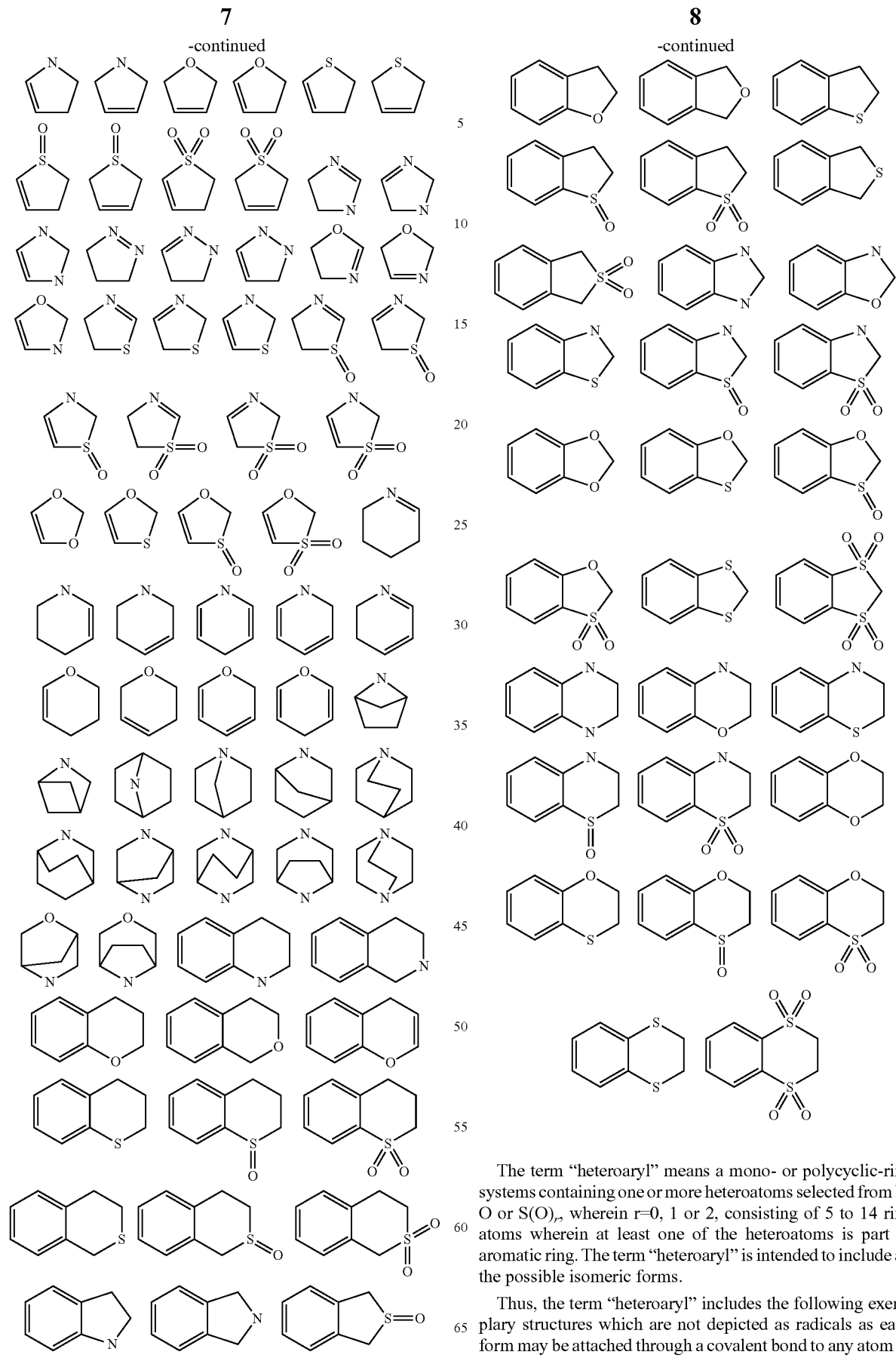

The term "heteroaryl" means a mono- or polycyclic-ring systems containing one or more heteroatoms selected from N, O or $S(O)_r$, wherein $r=0$, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

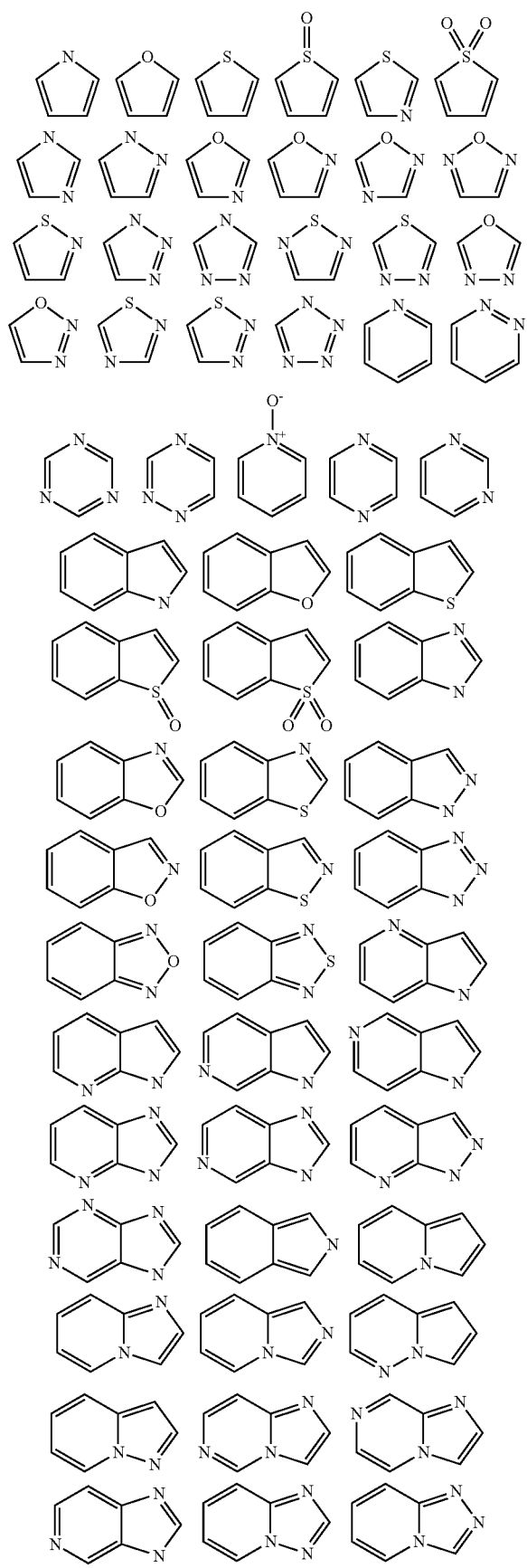

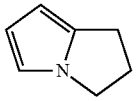

Preferred Embodiments

Preferred are the above mentioned compounds of formula 1 wherein $R^1$ is a 5 or 6 membered aromatic, hetero aromatic, non aromatic cyclic or heterocyclic ring system, optionally substituted by one, two or three residues selected from halogen or $C_{1-6}$-alkyl, optionally substituted with one or more F atoms.

Preferred are the above mentioned compounds of formula 1 wherein $R^1$ is a 5 or 6 membered aryl, heterocyclyl or heteroaryl ring optionally substituted by one, two or three residues selected from halogen or $C_{1-6}$-alkyl, optionally substituted with one or more F atoms.

Preferred are the above mentioned compounds of formula 1 wherein $R^1$ is phenyl or furanyl, optionally substituted by one or two residues selected from halogen or $C_{1-6}$-alkyl, optionally substituted with one or more F atoms.

Preferred are the above mentioned compounds of formula 1 wherein A is a N-linked four-, five- or six membered non-aromatic ring, with an additional condensed or spiro attached four-, five- or six membered ring, forming a bicyclic heterocyclic ring system, wherein
  if present one CH group is optionally replaced by N; and
  one, two or three $CH_2$ groups are optionally replaced by $C_{1-6}$-alkyl-CH—, $(C_{1-6}$-alkyl$)_2$-C—, $C_{1-6}$-alkyl-OC(O)CH—, CO, O, NH, $(C_{1-6}$-alkyl)N—, $SO_2$, wherein $C_{1-6}$-alkyl groups are optionally substituted by OH.

Preferred are the above mentioned compounds of formula 1 wherein A is a bicyclic heterocyclic system of the formula wherein
  if present one CH group is optionally replaced by N; and
  one, two or three $CH_2$ groups are optionally replaced by $C_{1-6}$-alkyl-CH—, $(C_{1-6}$-alkyl$)_2$-C—$C_{1-6}$-alkyl-OC(O)CH—, CO, O, NH, $(C_{1-6}$-alkyl)N—, $SO_2$, wherein $C_{1-6}$-alkyl groups are optionally substituted by OH Preferred are the above mentioned compounds of formula 1 wherein
$R^1$ is selected from the group consisting of phenyl, furanyl, optionally substituted by one or two residues selected from halogen or $C_{1-6}$-alkyl, optionally substituted with one or more F atoms;
$X^1$ is absent or $C_{1-6}$-alkyl; said alkyl optionally substituted with one or more F atoms;
$R^2$ is H;
$X^2$ is

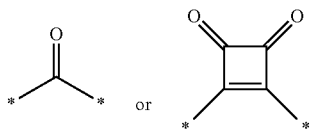

$R^3$ is H, halogen, CN, $C_{1-6}$-alkyl, optionally substituted with one or more F atoms; preferably H or Cl; preferably H;
A is a N-linked four-, five- or six membered non-aromatic ring, with an additional condensed or spiro attached four-, five- or six membered ring, forming a bicyclic heterocyclic ring system, wherein
if present one CH group is optionally replaced by N; and one, two or three $CH_2$ groups are optionally replaced by $C_{1-6}$-alkyl-CH—, $(C_{1-6}$-alkyl$)_2$-C—, $C_{1-6}$-alkyl-OC(O)CH—, CO, O, NH, $(C_{1-6}$-alkyl)N—, $SO_2$, wherein $C_{1-6}$-alkyl groups are optionally substituted by OH.
or a pharmaceutically acceptable salt thereof.

Preferred are the above mentioned compounds of formula 1 wherein
$R^1$ is selected from the group consisting of phenyl, furanyl, optionally substituted by one or two residues selected from halogen or $C_{1-4}$-alkyl, optionally substituted with one or more F atoms;
$X^1$ is absent or a branched or unbranched $C_{1-4}$-alkyl; said alkyl optionally substituted with one or more F atoms;
$R^2$ is H;
$X^2$ is

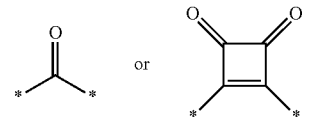

$R^3$ is H, halogen, CN, $C_{1-4}$-alkyl, optionally substituted with F; preferably H or Cl; preferably H;
A is a N-linked four-, five- or six membered non-aromatic ring, with an additional condensed or spiro attached four-, five- or six membered ring, forming a bicyclic heterocyclic ring system, wherein
if present one CH group is optionally replaced by N; and one, two or three $CH_2$ groups are optionally replaced by $C_{1-6}$-alkyl-CH—, $(C_{1-6}$-alkyl$)_2$-C—, $C_{1-6}$-alkyl-OC(O)CH—, CO, O, NH, $(C_{1-6}$-alkyl)N—, $SO_2$, wherein $C_{1-6}$-alkyl groups are optionally substituted by OH
or a pharmaceutically acceptable salt thereof.

Preferred are the above mentioned compounds of formula 1 wherein
$R^1$ is selected from the group consisting of phenyl, furanyl, optionally substituted by one or two residues selected from halogen or $C_{1-4}$-alkyl, optionally substituted with one or more F atoms;
$X^1$ is absent or a branched or unbranched $C_{1-4}$-alkyl; said alkyl optionally substituted with one or more F atoms;
$R^2$ is H;

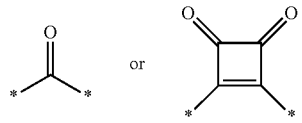

$R^3$ is H, halogen, CN, $C_{1-4}$-alkyl, optionally substituted with F; preferably H or Cl; preferably H;
A is a bicyclic heterocyclic system of the formula

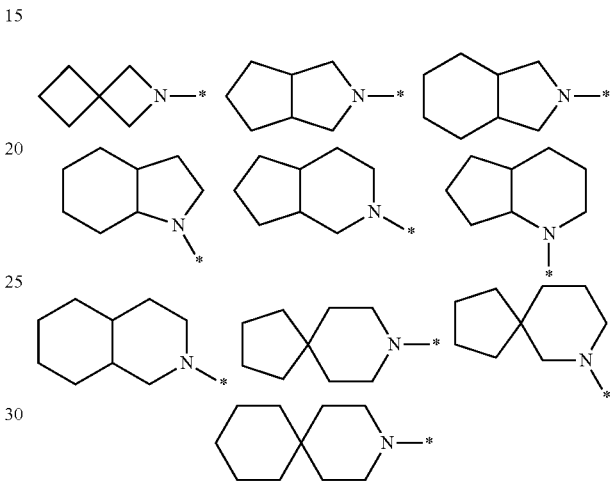

wherein
if present one CH group is optionally replaced by N; and one, two or three $CH_2$ groups are optionally replaced by $C_{1-6}$-alkyl-CH—, $(C_{1-6}$-alkyl$)_2$-C—, $C_{1-6}$-alkyl-OC(O)CH—, CO, O, NH, $(C_{1-6}$-alkyl)N—, $SO_2$, wherein $C_{1-6}$-alkyl groups are optionally substituted by OH
or a pharmaceutically acceptable salt thereof.

Preferred are the above mentioned compounds of formula 1 wherein
$R^1$ is selected from the group consisting of phenyl, furanyl, optionally substituted by one or two residues selected from Me, $CF_3$, F, Cl;
$X^1$ is absent or a branched or unbranched $C_{1-4}$-alkyl; said alkyl optionally substituted with one or more F atoms; preferably absent or $CH(CH_2CH_3)$;
$R^2$ is H;
$X^2$ is

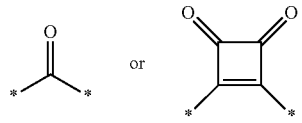

$R^3$ is H, Cl, CN, $CF_3$; preferably H or Cl; preferably H;
A is a bicyclic heterocyclic system of the formula

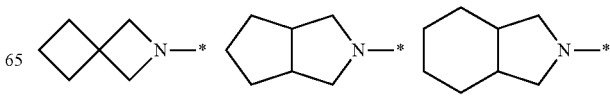

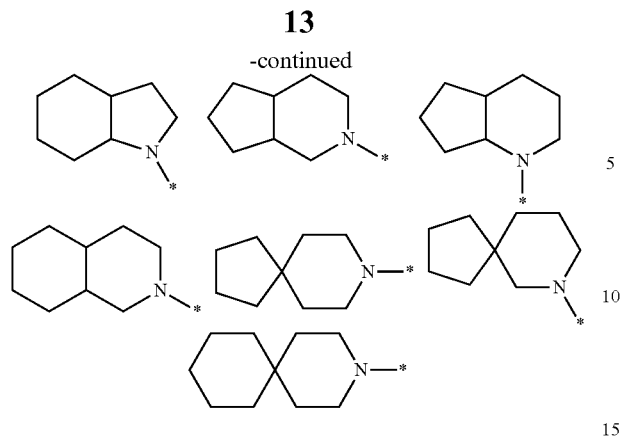

wherein
if present one CH group is optionally replaced by N; and
one, two or three CH₂ groups are optionally replaced by CHMe, CMe₂, CHCH₂OH, CHCOOMe, CO, O, NH, NMe, SO₂.

or a pharmaceutically acceptable salt thereof.

Preferred are the above mentioned compounds of formula 1 wherein $R^1$ is selected from the group consisting of phenyl, furanyl, optionally substituted by one or two residues selected from Me, CF₃, F, Cl;

$X^1$ is absent or a branched or unbranched $C_{1-4}$-alkyl; said alkyl optionally substituted with one or more F atoms; preferably absent or CH(CH₂CH₃);

$R^2$ is H;

$X^2$ is

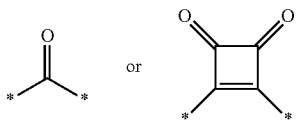

$R^3$ is H, Cl, CN, CF₃; preferably H;

A is a bicyclic heterocyclic system selected from the group consisting of

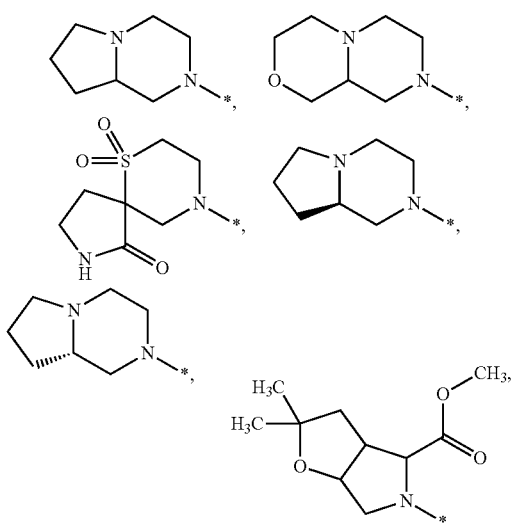

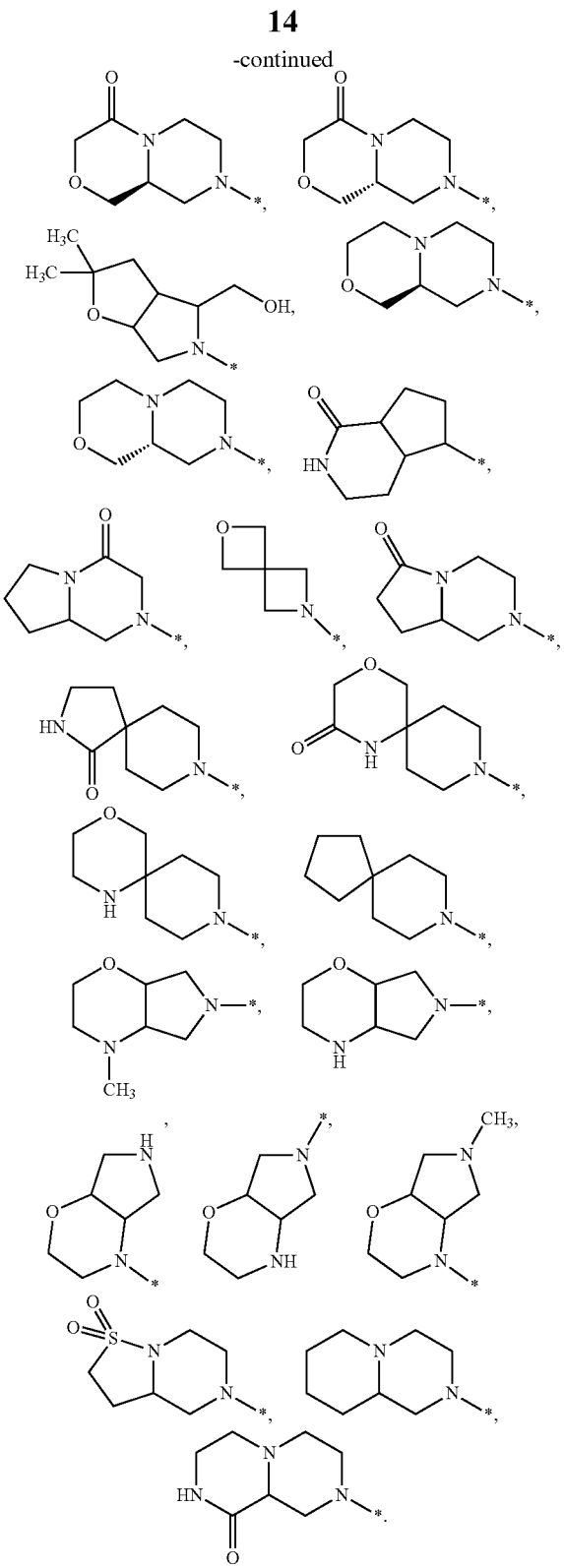

or a pharmaceutically acceptable salt thereof.

Preferred are the above mentioned compounds of formula 1 wherein $R^1$ is selected from the group consisting of phenyl, furanyl, optionally substituted by one or two residues selected from Me, CF₃, F, Cl;

$X^1$ is absent or a branched or unbranched $C_{1-4}$-alkyl; said alkyl optionally substituted with one or more F atoms; preferably absent or $CH(CH_2CH_3)$;
$R^2$ is H;
$X^2$ is

[chemical structures]

$R^3$ is H, Cl, CN, $CF_3$; preferably H;
A is a bicyclic heterocyclic system of the formula

[chemical structures]

wherein
  if present one CH group is optionally replaced by N; and
  one, two or three $CH_2$ groups are optionally replaced by $CHMe$, $CMe_2$, $CHCH_2OH$, $CHCOOMe$, CO, O, NH, NMe.
or a pharmaceutically acceptable salt thereof.

Preferred are the above mentioned compounds of formula 1 wherein
$R^1$ is selected from the group consisting of phenyl, furanyl, optionally substituted by one or two residues selected from Me, $CF_3$, F, Cl;
$X^1$ is absent or a branched or unbranched $C_{1-4}$-alkyl; said alkyl optionally substituted with one or more F atoms; preferably absent or $CH(CH_2CH_3)$;
$R^2$ is H;
$X^2$ is

[chemical structures]

$R^3$ is H;
A is a bicyclic heterocyclic system selected from the group consisting of

[chemical structures]

-continued

[chemical structures]

or a pharmaceutically acceptable salt thereof.

Preferred are the above mentioned compounds of formula 1 wherein
$R^1$ is selected from the group consisting of phenyl, furanyl, optionally substituted by one or two residues selected from Me, $CF_3$, F, Cl;
$X^1$ is absent or a branched or unbranched $C_{1-4}$-alkyl; said alkyl optionally substituted with one or more F atoms; preferably absent or $CH(CH_2CH_3)$;
$R^2$ is H;
$X^2$ is

[chemical structures]

$R^3$ is H, Cl, CN, $CF_3$; preferably H;

A is a bicyclic heterocyclic system of the formula

[Chemical structures of bicyclic heterocyclic systems]

wherein
one CH group is optionally replaced by N; and
one or two CH$_2$ groups are optionally replaced by CHMe, CMe$_2$, CHCH$_2$OH, CHCOOMe, CO, O, NH, NMe.

or a pharmaceutically acceptable salt thereof.

Preferred are the above mentioned compounds of formula 1 wherein

R$^1$ is selected from the group consisting of phenyl, furanyl, optionally substituted by one or two residues selected from Me, CF$_3$, F, Cl;

X$^1$ is absent or a branched or unbranched C$_{1-4}$-alkyl; said alkyl optionally substituted with one or more F atoms; preferably absent or CH(CH$_2$CH$_3$);

R$^2$ is H;

X$^2$ is

[Chemical structures: acyl and squarate groups]

R$^3$ is H;

A is a bicyclic heterocyclic system selected from the group consisting of

[Chemical structures of bicyclic heterocyclic systems]

-continued

[Chemical structures continued]

or a pharmaceutically acceptable salt thereof.

Preferred are the above mentioned compounds of formula 1 wherein

R$^1$ is selected from the group consisting of phenyl, furanyl, optionally substituted by one or two residues selected from Me, CF$_3$, F, Cl;

X$^1$ is absent or a branched or unbranched C$_{1-4}$-alkyl; said alkyl optionally substituted with one or more F atoms; preferably absent or CH(CH$_2$CH$_3$);

R$^2$ is H;

X$^2$ is

[Chemical structures: acyl and squarate groups]

R$^3$ is H, Cl, CN, CF$_3$; preferably H;

A is a bicyclic heterocyclic system of the formula

[Chemical structures of bicyclic heterocyclic systems]

wherein
one CH group is optionally replaced by N; and
one, two or three CH$_2$ groups are optionally replaced by CHMe, CMe$_2$, CO, O, NH, NMe; preferably CO, O, NH, NMe.

or a pharmaceutically acceptable salt thereof.

Preferred are the above mentioned compounds of formula 1 wherein

R$^1$ is selected from the group consisting of phenyl, furanyl, optionally substituted by one or two residues selected from Me, CF$_3$, F, Cl;

X$^1$ is absent or a branched or unbranched C$_{1-4}$-alkyl; said alkyl optionally substituted with one or more F atoms; preferably absent or CH(CH$_2$CH$_3$);

R$^2$ is H;

$X^2$ is

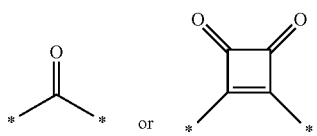

$R^3$ is H;

A is a bicyclic heterocyclic system selected from the group consisting of

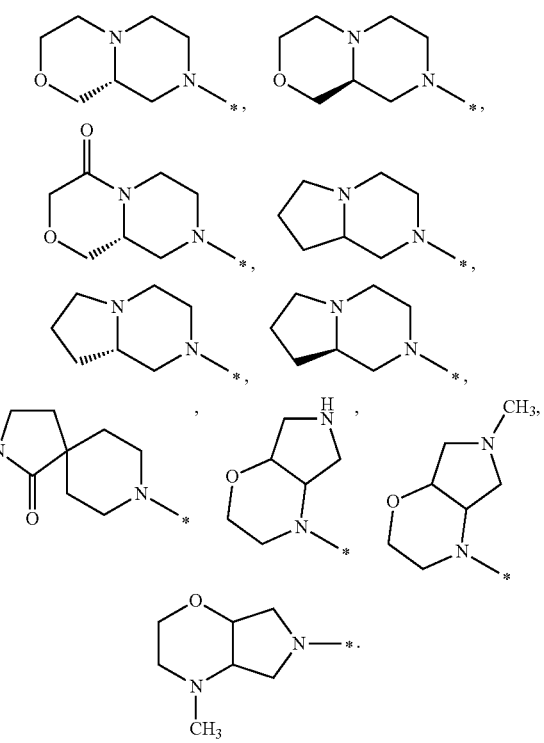

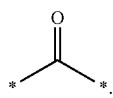

or a pharmaceutically acceptable salt thereof.

Preferred are the above mentioned compounds of formula 1 wherein $R^1$, $R^2$, $R^3$ and A are defined as above and $X^2$ is

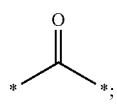

Preferred are the above mentioned compounds of formula 1 wherein $R^1$, $R^2$, $R^3$ and A are defined as above and $X^2$ is

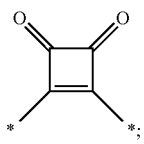

Preferred are the above mentioned compounds of formula 1 wherein $R^1$, $R^2$, $R^3$ and A are defined as above and when $X^2$ is

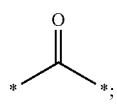

$X^1$ is absent;

Preferred are the above mentioned compounds of formula 1 wherein $R^1$, $R^2$, $R^3$ and A are defined as above and when $X^2$ is

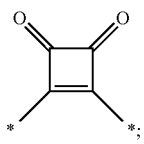

$X^1$ is absent or $CH(CH_2CH_3)$.

Preparation

General Procedures

Compounds of general formula (Z)

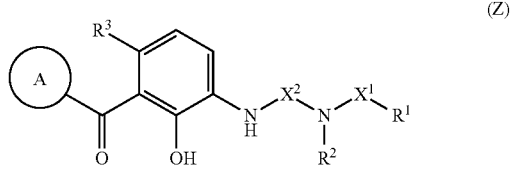

Can be synthesised according to the following general procedures using suitable reagents and methods known to those skilled in the art:

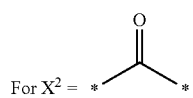

3-Nitrosalicylic acid, protected with protecting group P where necessary, is activated with a suitable reagent and coupled with a bicyclic amine to give intermediate A. The nitro group is reduced under suitable conditions to give intermediate B which is reacted with an isocyanate or equivalent reagent to give intermediate C. Protecting groups (if used) are then removed to give the required product as shown in the general Scheme 1 below.

Scheme 1

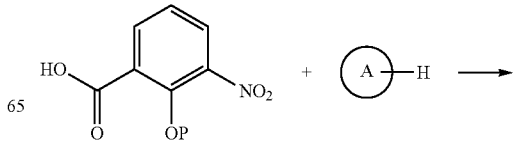

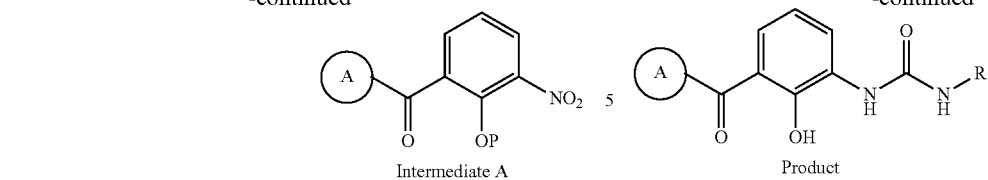

If the required isocyanate or equivalent reagent is not readily available, an amine can be reacted with a suitable chloroformate reagent to give an activated intermediate D which is then reacted with intermediate B to give intermediate C. Protecting groups (if used) are then removed to give the required product as shown in the general Scheme 2 below

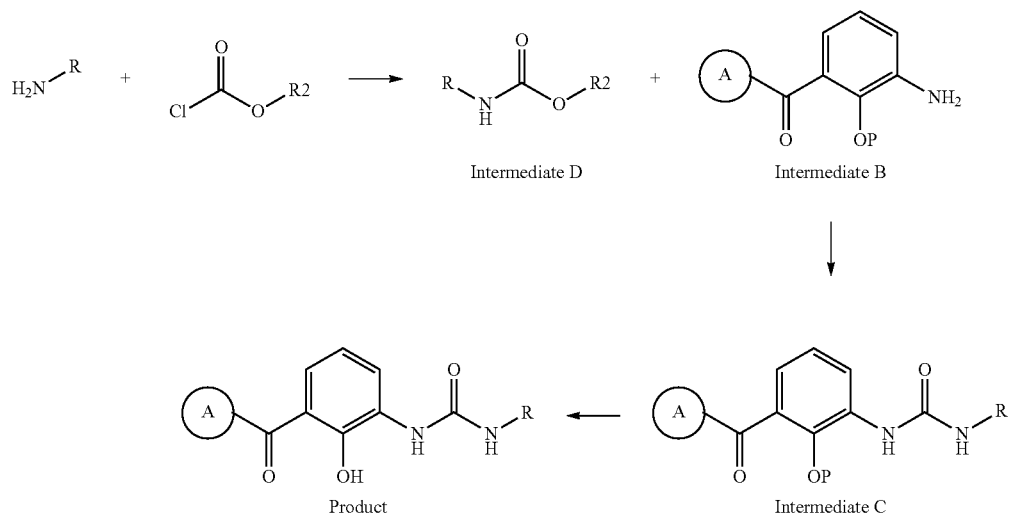

Alternatively, 3-aminosalicylic acid, protected with protecting group P where necessary, is reacted with an isocyanate or equivalent reagent to give intermediate E, which is activated with a suitable reagent and coupled with a bicyclic amine to give intermediate C. Protecting groups (if used) are then removed to give the required product as shown in the general Scheme 3 below.

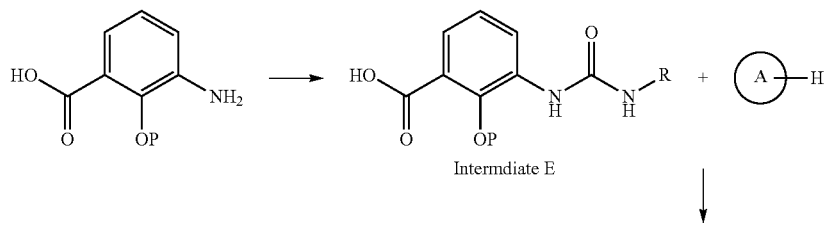

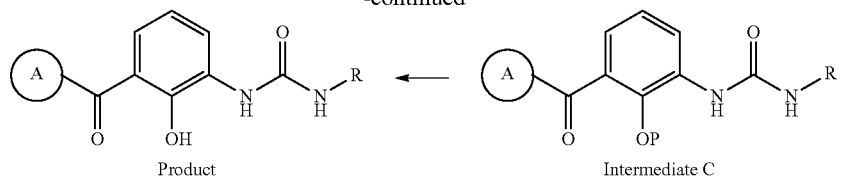

If the required isocyanate or equivalent reagent is not readily available, an amine can be reacted with a suitable chloroformate reagent to give an activated intermediate D which is then reacted with 3-aminosalicylic acid, protected with protecting group P where necessary to give intermediate E. as shown in the general Scheme 4 below, the synthesis is then completed as described in Scheme 3.

Scheme 4

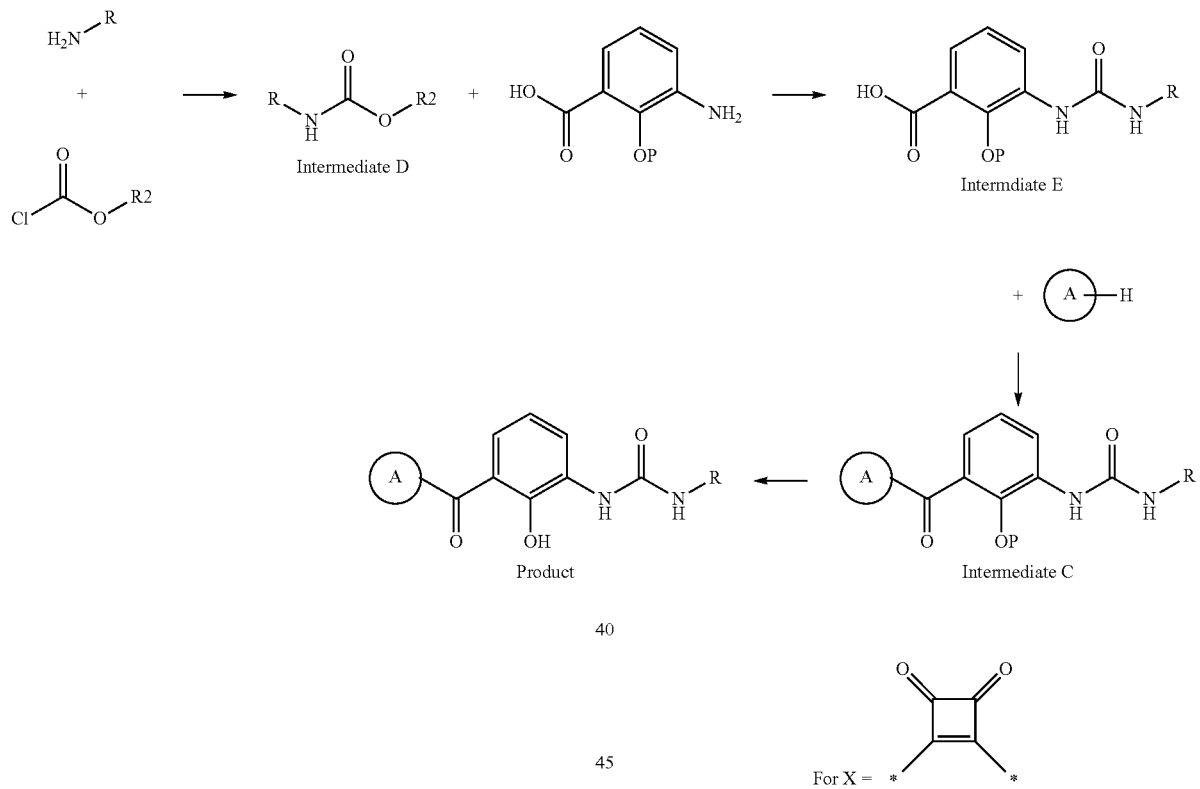

Intermediate B, synthesised as described in general Scheme 1 is reacted with 3,4-diethoxy-3-cyclobutene-1,2-dione or a similar reagent to give intermediate G, which is reacted with a suitable amine to give intermediate H. Protecting groups (if used) are then removed to give the required product as shown in the general Scheme 5 below.

Scheme 5

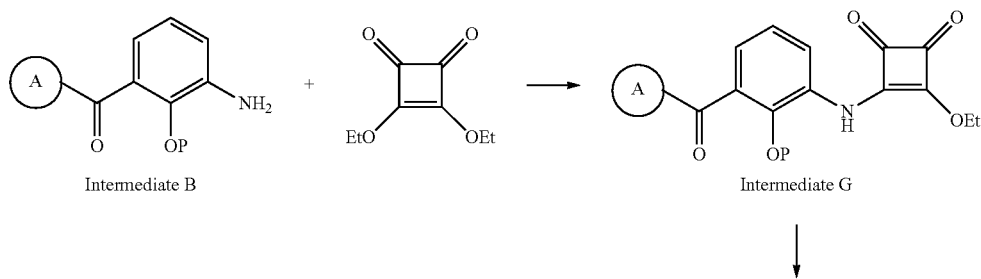

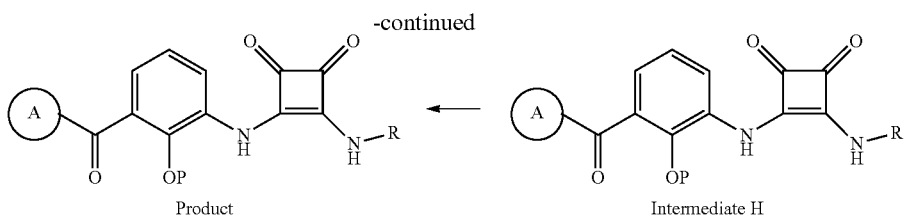

Alternatively, 3-aminosalicylic acid, protected with protecting group P where necessary, is reacted with 3,4-diethoxy-3-cyclobutene-1,2-dione or a similar reagent to give intermediate I, which is reacted with a suitable amine to give intermediate J. This is activated with a suitable reagent and coupled with a bicyclic amine to give intermediate H. Protecting groups (if used) are then removed to give the required product as shown in the general Scheme 6 below.

| ABBREVIATIONS | |
|---|---|
| ACN | acetonitrile |
| APCI | atmospheric pressure chemicalionization (in MS) |
| BOP | Benzotriazole-1-yl-oxy-tris-(dimethylamino)-phosphonium hexafluorophosphate |

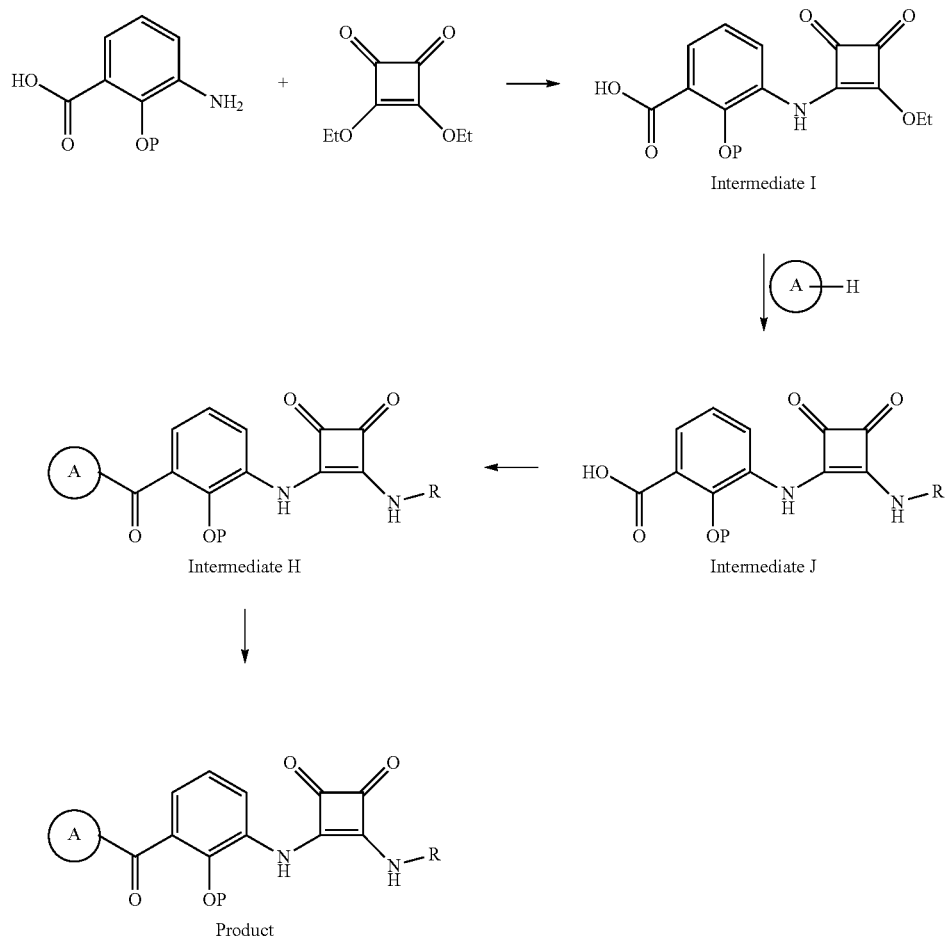

Suitable protecting groups P for the syntheses described above and suitable conditions for their use can be chosen by those skilled in the art from examples described in "Protecting Groups, 3$^{rd}$ Edition", Philip J. Kocienski, Theime, 2005 or "Greene's Protective Groups in Organic Synthesis, 4th Edition", Peter G. M. Wuts, Theodora W. Greene, John Wiley and Sons, 2007.

| -continued | |
|---|---|
| ABBREVIATIONS | |
| br | broad (NMR) |
| Ctrl | control |
| DAD | diode array detector |

ABBREVIATIONS

| | |
|---|---|
| DCM | dichloromethane |
| d | doublet (NMR) |
| DMA | N,N-dimethylacetamide |
| DMF | N,N-dimethylformamide |
| DMSO | dimethyl sulfoxide |
| EI | electron impact (in MS) |
| ES | electrospray (in MS) |
| GC/MS | gas chromatography with mass spectrometric detection |
| h | hour(s) |
| HATU | O-(7-azabenzotriazol-1-yl)-N,N,N',N'-tetramethyluronium hexafluoro-phosphate |
| HPLC | high performance liquid chromatography |
| HPLC/MS | coupled high performance liquid chromatography-mass spectrometry |
| m | multiplet (NMR) |
| min | minutes |
| MS | mass spectrometry |
| NMP | N-Methyl-2-pyrrolidinone |
| NMR | nuclear magnetic resonance |
| PyBOP | (Benzotriazol-1-yloxy)tripyrrolidinophosphonium hexafluorophosphate |
| Rt | retention time (in HPLC) |
| s | singlet (NMR) |
| SCX | Strong Cation Exchange |
| sec | secondary |
| t | triplet (NMR) |
| TBTU | O-(1H-benzo-1,2,3-triazol-1-yl)-N,N,N',N'-tetramethyluronium tetrafluoroborate |
| tert | tertiary |
| TFA | trifluoroacetic acid |
| THF | tetrahydrofuran |
| TLC | thin-layer chromatography |
| UV | ultraviolet absorption |

Analytical Methods

HPLC-MS and HPLC-MS are performed according to the following methods:

HPLC Method 1

| | |
|---|---|
| Instrument: | LC/MS Waters Acquity UPLC System DAD, SQD single quadrupole |
| Column: | HSS C18 1.8 μm 2.1 × 50 mm, Temp 35° C. |
| Mobile phase: | A = H$_2$O 90% + 10% CH$_3$CN + CF$_3$COOH 0.1%<br>B = CH$_3$CN 90% + H$_2$O 10% |

| Time in min | % A | % B | flow rate in ml/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

| | |
|---|---|
| Detection: | UV 254 nm |
| Detection: | SQD, single quadrupole |
| Ion source: | ES+/ES− |
| Scan range: | 90-900 amu |

HPLC Method 2

| | |
|---|---|
| Instrument: | LC/MS Waters Acquity UPLC System DAD, SQD single quadrupole |
| Column: | BEH C18 1.7 μm 2.1 × 50 mm, Temp 35° C. |
| Mobile phase: | A = H$_2$O 90% + 10% CH$_3$CN + CF$_3$COOH 5 mM<br>B = CH$_3$CN 90% + H$_2$O 10% |

| Time in min | % A | % B | flow rate in ml/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

| | |
|---|---|
| Detection: | UV 254 nm |
| Detection: | SQD, single quadrupole |
| Ion source: | ES+/ES− |
| Scan range: | 90-900 amu |

HPLC Method 3

Instrument: LC/MS Waters. HPLC Alliance 2695 DAD, ZQ Quadrupole.
Column: Zorbax Eclipse Plus C18, 3.5 μm, 4.6×50 mm
Mobile phase: A=H$_2$O 90%+NH$_4$COOH 5 mM+10% ACN
B=ACN
Flow rate: 1300 μL/min
Gradient: A/B(90:10), then to A/B (10:90) in 3.50 minutes for 1 minute
Detection: UV @ 254 nm
Detection: Waters ZQ, Quadrupole
Ion source: ES
Scan range: 120-900

HPLC Method 4

Instrument: LC/MS Waters. HPLC Alliance 2695 DAD, ZQ Quadrupole.
Column: Gemini C18, 3 μm, 4.6×50 mm
Mobile phase: A=H$_2$O 90%+0.1% TFA+10% ACN
B=ACN
Flow rate: 1300 μL/min
Gradient: A/B (70:30), then to A/B (10:90) in 3.50 minutes for 1 minute
Detection: UV @ 254 nm
Detection: Waters ZQ, Quadrupole
Ion source: ES
Scan range: 120-900

HPLC Method 5

| | |
|---|---|
| Instrument: | LC/MS ThermoFinnigan HPLC Surveyor DAD, MSQ single quadrupole |
| Column: | Synergy Hydro RP80A, 4 μm, 4.6 × 100 mm |
| Mobile phase: | A = H$_2$O 90% + 10% ACN + NH$_4$COOH 10 mM<br>B = ACN 90% + H$_2$O 10% + NH$_4$COOH 10 mM |

| Time in min: | % A | % B | Flow rate in ml/min |
|---|---|---|---|
| 0.00 | 100 | 0 | 1.2 |
| 1.50 | 100 | 0 | 1.2 |
| 11.5 | 0 | 100 | 1.2 |
| 13 | 0 | 100 | 1.2 |

| | | | |
|---|---|---|---|
| 13.5 | 100 | 0 | 1.2 |
| 15 | 100 | 0 | 1.2 |

| | |
|---|---|
| Detection: | UV 254 nm |
| Detection: | Finnigan MSQ, single quadrupole |
| Ion source: | APCI+/APCI– |
| Scan range: | 100-900 amu |

HPLC Method 6

| | |
|---|---|
| Instrument: | LC/MS ThermoFinnigan HPLC Surveyor DAD, LCQDuo Ion Trap |
| Column: | Symmetry Shield RP8, 5 μm, 4.6 × 150 mm |
| Mobile phase: | A = H$_2$O 90% + 10% ACN + HCOOH 0.1%<br>B = ACN 90% + H$_2$O 10% + HCOOH 0.1% |

| Time in min: | % A | % B | Flow rate in ml/min |
|---|---|---|---|
| 0.00 | 95 | 5 | 1 |
| 1.50 | 95 | 5 | 1 |
| 11.5 | 5 | 95 | 1 |
| 13 | 5 | 95 | 1 |
| 13.5 | 95 | 5 | 1 |
| 15 | 95 | 5 | 1 |

| | |
|---|---|
| Detection: | UV 254 nm |
| Detection: | Finnigan LCQDuo, Ion Trap |
| Ion source: | ES+ |
| Scan range: | 100-900 amu |

GC/MS were performed under the following conditions:
GC/MS Method 7
Instrument: GC/MS Thermo Scientific TRACE GC ULTRA, DSQ II MS single quadrupole
Column: Agilent DB-5MS, 25m×0.25 mm×0.25 μm
Carrier gas: Helium, 1 ml/min constant flow
Oven Program: 50° C., to 100° C. in 10° C./min, to 200° C. in 20° C./min, to 320° C. in 30° C./min (hold 10 min)
Detection: DSQ II MS single quadrupole
Ion source: EI
Scan range: 50-450 amu
NMR are recorded on Varian 400 MHz or Varian Inova 500 MHz instruments. Chemical shifts are expressed in parts per million (ppm) relative to tetramethylsilane using the solvent residual peak as internal standard.

SYNTHETIC EXAMPLES

All materials used are purchased from commercial sources unless otherwise stated. References are given for the syntheses of non-commercially available reagents.

Flash chromatography is performed on prepacked silica gel columns from Biotage using FlashVac (IST), Flashmaster (Argonaut) SP1 or Isolera (Biotage) manual and automatic purification systems.

SCX columns are purchased from Biotage or Phenomenex and are washed with methanol prior to use.

Reactions are monitored by TLC using suitable solvents and visualisation by UV absorbance or a suitable staining reagent.

Semi-preparative reverse phase HPLC is performed on a C18 column using a gradient of acetonitrile: 0.5% TFA in water, 1:9-9:1 or a gradient of acetonitrile: 0.5% NH$_4$COOH in water, 1:9-9:1. Automatic fraction collection is triggered by mass spectrometry.

Synthesis of Example 1

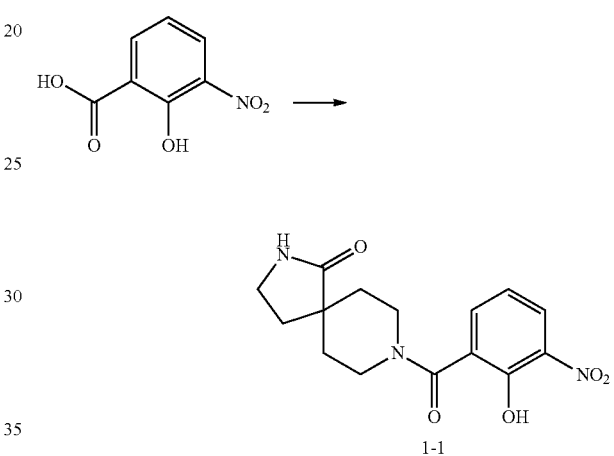

To a solution of 3-nitrosalicyclic acid (500 mg, 2.73 mmol) in dichloromethane (10 mL) is added oxalylchloride (2 M in dichloromethane, 1.50 ml, 3 mmol) and three drops of N,N-dimethylformamide. The mixture is stirred at room temperature overnight. The solvent is evaporated under vacuum to leave a crude residue, a portion of which (127 mg, 0.63 mmol) is dissolved in dichloromethane (5 mL) and the solution cooled to 0° C. Triethylamine (0.22 mL, 1.57 mmol) is added followed by 2,8-diaza-spiro[4.5]decan-1-one hydrochloride (100 mg, 0.52 mmol). The mixture is allowed to warm to room temperature and stirred overnight. Water is added, the phases separated, the organic layer dried over MgSO$_4$ and evaporated under reduced pressure to give compound 1-1.

Yield: 200 mg

ES mass spectrum: [M+H]$^+$=320

Retention time: 0.69 min (HPLC method 2)

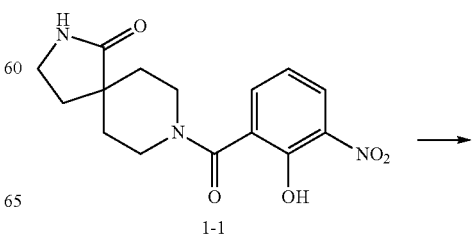
1-1

-continued

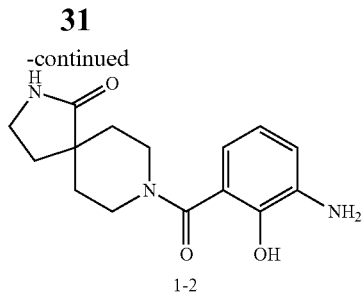

1-2

A solution of compound 1-1 (200 mg, 0.63 mmol) in ethanol (20 mL) is hydrogenated at 3 Bar using 30 mg of 10% Pd/C as the catalyst for 6 h. The reaction mixture is filtered through celite, the solvent removed under vacuum and the crude material purified by flash chromatography (Silica Gel, gradient: cyclohexane/ethyl acetate from 100:0 to 0:100) to give compound 1-2.

Yield: 130 mg
ES mass spectrum: [M+H]$^+$=290
Retention time: 0.65 min (HPLC method 2)

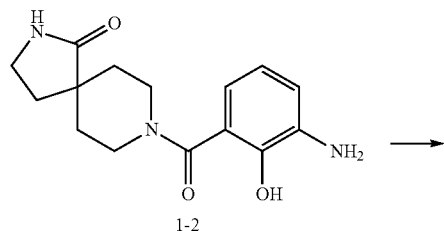

1-2

-continued

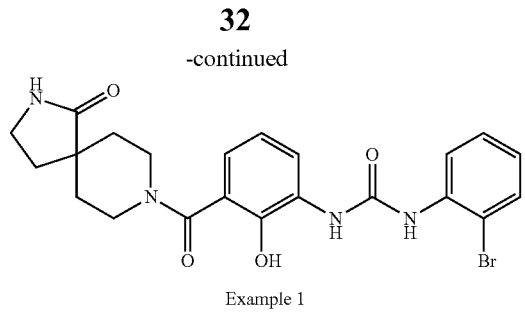

Example 1

Compound 1-2 (20 mg, 0.069 mmol) is dissolved in dichloromethane (1 mL), 2-bromophenylisocyanate (8.52 μL, 0.069 mmol) is added and the mixture stirred at room temperature overnight. The volatiles are removed under vacuum and the crude material purified via semi-preparative reversed phase HPLC to give Example 1.

Yield: 4 mg
ES mass spectrum: [M+H]$^+$=487
Retention time: 7.53 min (HPLC Method 5)
$^1$H NMR (Varian Inova 500 MHz. DMSO-d6; 27° C.) 8.82 (1H, br); 8.49 (1H, br); 7.93 (1H, dd); 7.86 (1H, dd); 7.59 (2H, m); 7.33 (1H, m); 6.99 (1H, m); 6.82 (2H, m); 3.88 (2H, br); 3.18 (2H, m); 3.10 (2H, m); 1.99 (2H, t); 1.66 (2H, m); 1.39 (2H, m); 1 H not observed.

The following compounds are prepared in a manner analogous to that described for the preparation of Example 1 by reacting compound 1-2 with the appropriate isocyanate.

| Example | Structure | Analysis |
| --- | --- | --- |
| 2 | 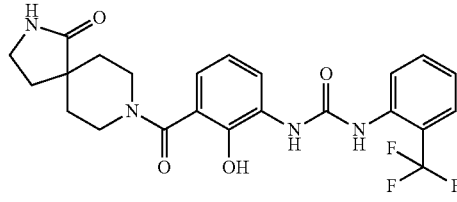<br>2-1 | ES mass spectrum: [M + H]$^+$ = 477<br>Retention time: 7.50 min (HPLC Method 5)<br>$^1$H NMR (Varian Inova 500 MHz. DMSO-d6; 27° C.)9.11 (1H, br); 8.79 (1H, br); 7.91 (1H, dd); 7.83 (1H, d); 7.63 (3H, m); 7.29 (1H, t); 6.83 (2H, m); 3.90 (2H, br); 3.12 (4H, m); 1.98 (2H, t); 1.64 (2H, m); 1.38 (2H, m); 1 H not observed. |
| 3 | 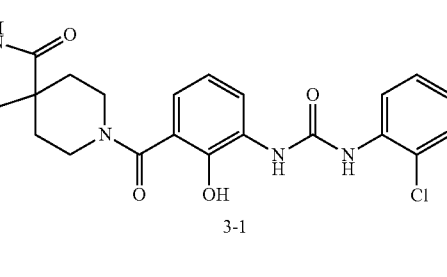<br>3-1 | ES mass spectrum: [M + H]$^+$ = 477<br>Retention time: 8.22 min (HPLC Method 5) $^1$H NMR (Varian Inova 500 MHz. DMSO-d6; 27° C.) 9.24(1H, s); 9.10 (1H, br); 8.09 (1H, dd); 7.85 (1H, dd); 7.58 (1H, s); 7.33-7.13 (3H, m); 6.87 (1H, t); 6.82 (1H, dd ); 3.80-4.03 (2H, br); 3.18 (2H, t); (2H, dt); 1.99 (2H, t); 1.67 (2H, m); 1.39 (2H, m). |

Synthesis of Example 4

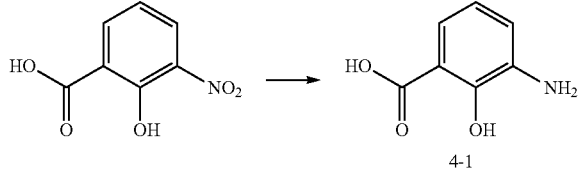

4-1

3-Nitrosalicylic acid (1.0 g, 5.46 mmol) is dissolved in absolute ethanol (60 mL) and hydrogenated at 3 Bar for 6 hours using 10% palladium on activated charcoal (116 mg) as the catalyst. The suspension is filtered through Celite and the solvent removed under reduced pressure to give compound 4-1.

Yield: 600 mg

ES mass spectrum: [M+H]$^+$=154

Retention time: 0.28 min (HPLC method 2)

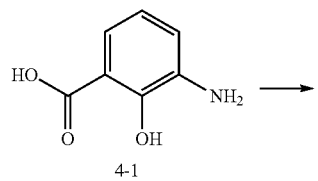

4-1

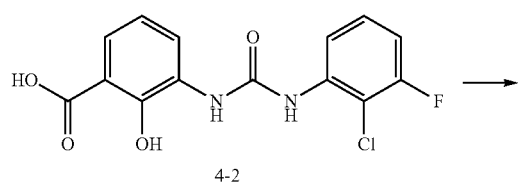

4-2

4-Nitrophenylchloroformate (868 mg, 4.31 mmol) is dissolved in dry dichloromethane (10 mL) and cooled to 0° C. A solution of 2-chloro-3-fluoroaniline (627 mg, 4.31 mmol) and pyridine (355 µL 4.48 mmol) in dry DCM (10 mL) is added dropwise and the mixture stirred for 15 minutes. Compound 4-1 (600 mg, 3.92 mmol) is added followed by pyridine (1.2 mL, 15.1 mmol) and the mixture stirred for 3 days. The mixture is shaken with 0.2 M HCl solution and the phases allowed to separate. The organic phase is dried and the solvent removed. The residue is triturated with diethyl ether to give compound 4-2.

Yield: 850 mg

ES mass spectrum: [M+H]$^+$=325

Retention time: 1.19 min (HPLC method 1)

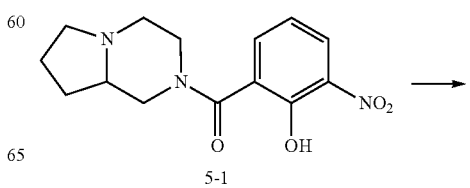

4-2

-continued

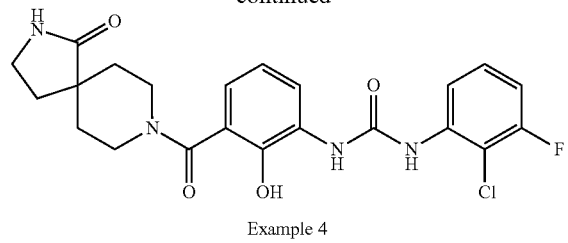

Example 4

Compound 4-2 (50 mg, 0.15 mmol) and PyBOP (160 mg, 0.31 mmol) are dissolved in DMF (1.5 mL) and stirred for 20 minutes. 2,8-Diaza-spiro[4.5]decan-1-one hydrochloride (41 mg, 0.22 mmol) and triethylamine (86 µL, 0.62 mmol) are added and the mixture stirred overnight. The solvent is removed under reduced pressure, the residue dissolved in DCM and washed with 5% aqueous NaHCO$_3$ solution, dried and the solvent removed. The residue is purified by flash chromatography (Silica Gel, gradient: DCM/methanol from 98:2 to 90:10) to give Example 4.

Yield: 14 mg

ES mass spectrum: [M+H]$^+$=461

Retention time: 9.95 min (Method 6)

$^1$H NMR (Varian 400 MHz. DMSO-d6; 28° C.) 9.57 (1H, br); 9.17 (1H, s); 9.08 (1H, s); 7.97 (2H, m); 7.57 (1H, s); 7.31 (1H, m); 7.05 (1H, m); 6.84 (2H, m); 3.91 (1H, br); 3.09 (5H, m); 1.99 (2H, m); 1.67 (2H, m); 1.39 (2H, m).

Synthesis of Example 5

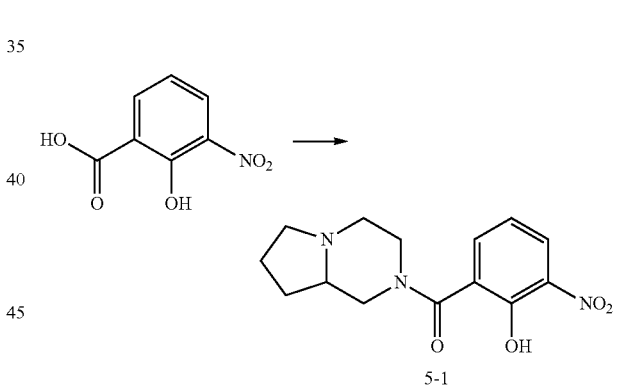

5-1

Compound 5-1 is prepared in a manner analogous to that described for compound 1-1 using octahydro-pyrrolo[1,2-a]pyrazine instead of 2,8-diaza-spiro[4.5]decan-1-one hydrochloride.

Yield: 600 mg

ES mass spectrum: [M+H]+=292

Retention time: 0.64 min (HPLC method 2)

-continued

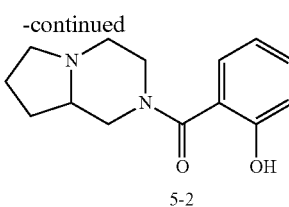
5-2

Compound 5-2 is prepared from compound 5-1 in a manner analogous to that described for compound 1-2.

Yield: 120 mg

ES mass spectrum: [M+H]+=262

Retention time: 5.96 min (HPLC Method 5)

Compound 5-2 is treated in a manner analogous to that described for Example 1 to give Example 5.

Yield: 17 mg

ES mass spectrum: $[M+H]^+=459$

Retention time: 8.83 min (HPLC Method 5)

$^1$H NMR (Varian Inova 500 MHz. DMSO-d6; 27° C.) 9.15 (1H, s); 8.8 (1H, s); 7.94 (1H, dd); 7.88 (1H, dd); 7.62 (1H, dd); 7.33 (1H, t); 6.98 (1H, t); 6.84 (1H, t); 6.79 (1H, d); 3-3.94 (3H, m); 2.05 (2H, m); 1.89 (1H, m); 1.72-1.66 (3H, m); 1.28 (2H, m); 3 H not observed.

The following compounds are prepared in a manner analogous to that described for the preparation of Example 1 by reacting compound 5-2 with the appropriate isocyanate.

| Example | Structure | Analysis |
|---|---|---|
| 6 | 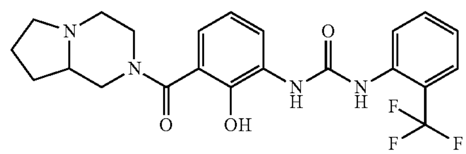 [SMILES: O=C(Nc1ccccc1C(F)(F)F)Nc1cccc(C(=O)N2CCN3CCCC3C2)c1O] | ES mass spectrum: $[M + H]^+ = 449$ Retention time: 8.76 min (HPLC Method 5) $^1$H NMR (Varian 400 MHz. DMSO-d6; 28° C.) 9.1(1H, s); 8.79 (1H, s); 7.91 (1H, dd); 7.84 (1H, dd); 7.63-7.69 (2H, m); 7.28 (1H, t); 6.85 (1H, t); 6.80 (1H, m); 3-3.94 (3H, m); 2.05 (2H, m); 1.90 (1H, m); 1.72-1.66(3H, m); 1.28 (2H, m); 3 H not observed. |
| 7 | 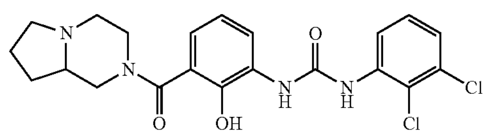 [SMILES: O=C(Nc1cccc(C(=O)N2CCN3CCCC3C2)c1O)Nc1cccc(Cl)c1Cl] | ES mass spectrum: $[M + H]^+ = 449$ Retention time: 9.76 min (HPLC Method 5) $^1$H NMR (Varian Inova 500 MHz. DMSO-d6; 27° C.) 9.28 (2H, br); 8.43 (2H, br); 8.08 (1H, d); 7.90 (1H, d); 7.30 (2H, m); 6.83 (2H, m); 2.97 (2H, m); 2.06 (2H, m); 1.88 (2H, m); 1.68 (4H, m); 1.28 (2H, m). |

Synthesis of Example 8

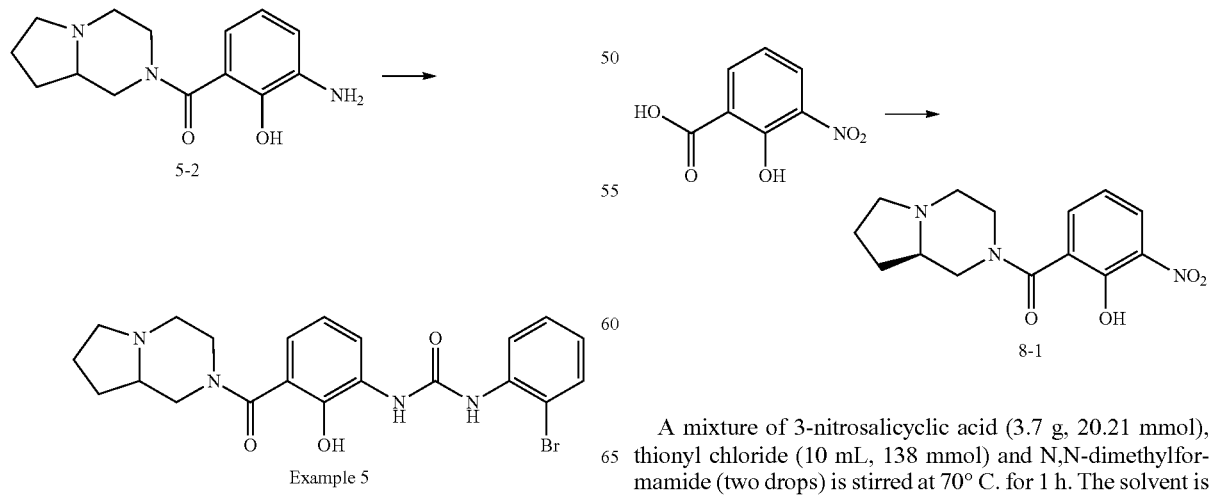

A mixture of 3-nitrosalicyclic acid (3.7 g, 20.21 mmol), thionyl chloride (10 mL, 138 mmol) and N,N-dimethylformamide (two drops) is stirred at 70° C. for 1 h. The solvent is evaporated under vacuum to leave a crude residue which is dissolved in dichloromethane (30 mL). Triethylamine (3.31 mL, 23.8 mmol) is added followed by (R)-octahydro-pyrrolo[1,2-a]pyrazine (1 g, 7.92 mmol). The mixture is stirred at room temperature overnight. The solvent is removed under reduced pressure and the crude residue purified by flash chromatography (Silica Gel, gradient: dichloromethane/methanol from 100:0 to 80:20) to give compound 8-1.

Yield: 2.25 g

ES mass spectrum: [M+H]$^+$=291

Retention time: 1.54 min (HPLC Method 3)

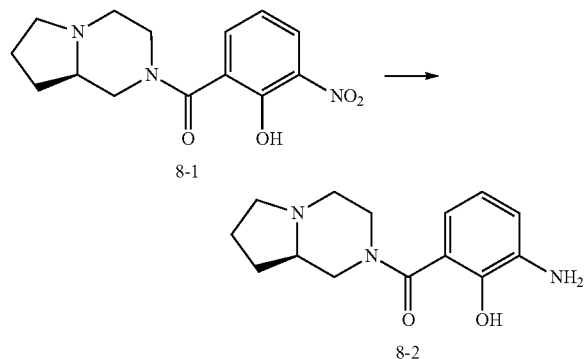

Compound 8-2 is prepared from compound 8-1 in a manner analogous to that described for compound 1-2. The product is purified by flash chromatography (Silica Gel, gradient: dichloromethane/methanol/ammonia from 100:0:0 to 90:10:1).

Yield: 1.12 g

ES mass spectrum: [M+H]$^+$=262

Retention time: 5.80 (HPLC Method 5)

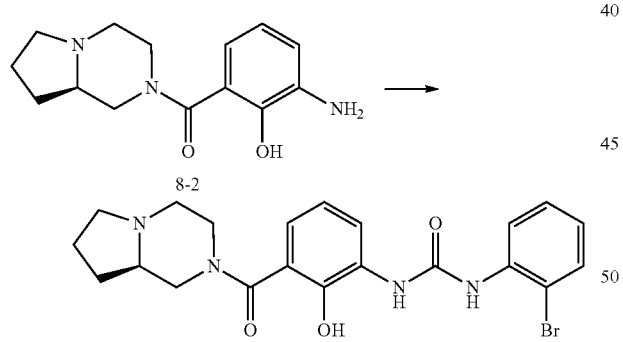

Example 8

Compound 8-2 is treated in a manner analogous to that described for Example 1. The product is isolated by flash chromatography (Silica Gel, gradient: dichloromethane/methanol from 100:0 to 90:10) to give Example 8.

Yield: 40 mg

ES mass spectrum: [M+H]$^+$=459

Retention time: 6.58 (HPLC Method 6)

$^1$H NMR (Varian Inova 500 MHz. DMSO-d6; 27° C.) 9.63 (1H, s); 9.12 (1H, s); 8.79 (1H, s); 7.95 (1H, dd); 7.89 (1H, dd); 7.61 (1H, dd); 7.33 (1H, dt); 6.99 (1H, dt); 6.85 (1H, t); 6.80 (1H, dd); 2.97 (4H, m); 2.65 (1H, br); 2.05 (2H, m); 1.89 (1H, m); 1.67 (3H, m); 1.28 (1H, m); 1 H not observed.

Synthesis of Example 9

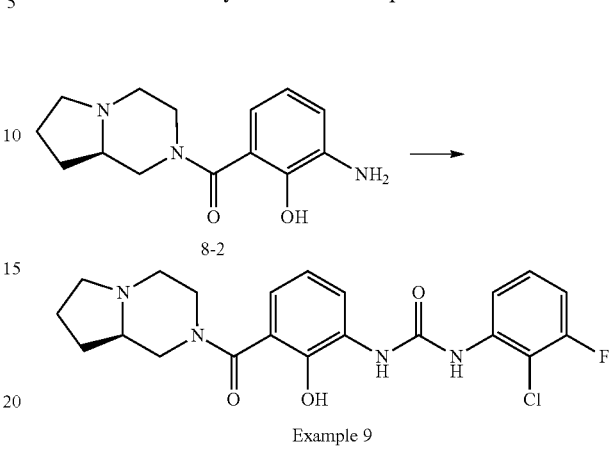

Example 9

To a solution of 4-nitro-phenyl-chloroformate (41.54 mg, 0.206 mmol) in dichloromethane (6 mL) cooled to 0° C. is added dropwise a solution of 2-chloro-3-fluoro-aniline (30 mg, 0.206 mmol) and pyridine (18 µL, 0.23 mmol) in dichloromethane (2 mL). The reaction mixture is stirred at 0° C. for 5 min, then allowed to warm to room temperature. After 1 h, a solution of compound 8-2 (40 mg, 0.15 mmol) and pyridine (36 µL, 0.45 mmol) in dichloromethane (3 mL) is added and the mixture stirred at room temperature overnight. The solvent is removed under vacuum and the crude material purified via semi-preparative reversed phase HPLC. The material obtained is dissolved in methanol, loaded onto an SCX cartridge, washed with methanol and then eluted with 1 M NH$_3$ in methanol to give Example 9.

Yield: 46 mg

ES mass spectrum: [M+H]$^+$=433

Retention time: 9.20 (HPLC Method 5)

$^1$H NMR (Varian 400 MHz. DMSO-d6; 28° C.) 9.63 (1H, br); 9.19 (1H, br); 9.11 (1H, br); 7.98 (1H, d); 7.93 (1H, dd); 7.30 (1H, m); 7.05 (1H, m); 6.89-6.80 (2H, m); 4.20-3.80 (2H, br); 2.99 (3H, m); 2.66 (1H, m); 2.07-2.00 (2H, m); 1.86 (1H, m); 1.70 (3H, m); 1.28 (1H, m); 1 H not observed.

Synthesis of Example 10

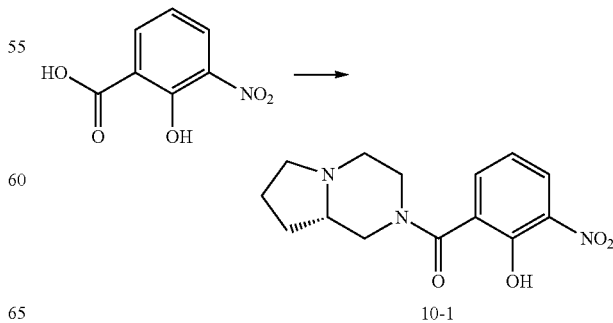

10-1

Compound 10-1 is prepared in a manner analogous to that described for compound 8-1 using (S)-octahydro-pyrrolo[1,2-a]pyrazine instead of (R)-octahydro-pyrrolo[1,2-a]pyrazine.

Yield: 2.3 g

ES mass spectrum: [M+H]$^+$=291

Retention time: 1.52 min (HPLC Method 3)

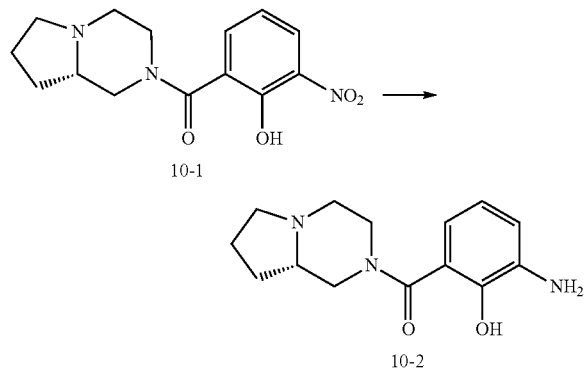

Compound 10-2 is prepared from compound 10-1 in a manner analogous to that described for compound I-2. The product is purified by flash chromatography (Silica Gel, gradient: dichloromethane/methanol/ammonia from 100:0:0 to 90:10:1)

Yield: 1.52 g

ES mass spectrum: [M+H]$^+$=262

Retention time: 6.02 (HPLC Method 5)

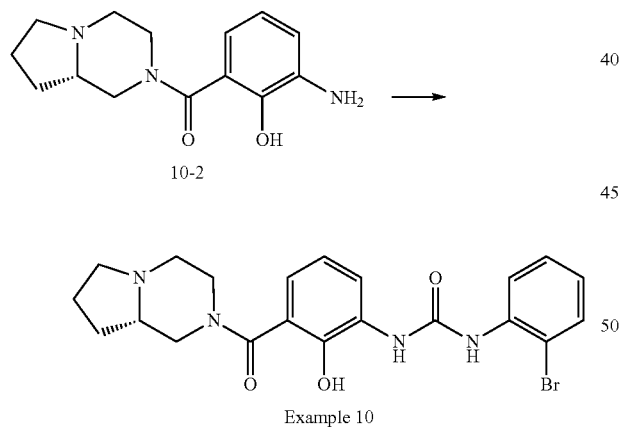

Compound 10-2 is treated in a manner analogous to that described for Example 1. The product is isolated by flash chromatography (Silica Gel, gradient: dichloromethane/methanol from 100:0 to 0:100) to give Example 10.

Yield: 30 mg

ES mass spectrum: [M+H]$^+$=459

Retention time: 6.65 (HPLC Method 6)

$^1$H NMR (Varian Inova 500 MHz. DMSO-d6; 27° C.) 9.63 (1H, s); 9.12 (1H, s); 8.79 (1H, s); 7.95 (1H, dd); 7.89 (1H, dd); 7.61 (1H, dd); 7.32 (1H, dt); 6.99 (1H, dt); 6.85 (1H, t); 6.79 (1H, dd); 2.98 (4H, m); 2.65 (1H, br); 2.05 (2H, m); 1.89 (1H, m); 1.68 (3H, m); 1.28 (1H, m); 1 H not observed.

Synthesis of Example 11

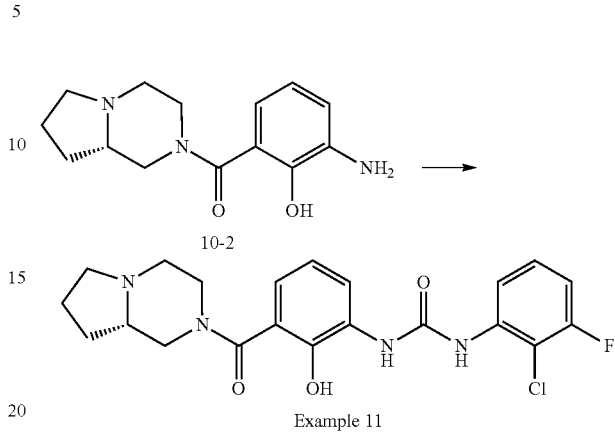

Compound 10-2 is treated in a manner analogous to that described for compound 9-1. The product is further purified by flash chromatography (Silica Gel, gradient: ethyl acetate/methanol from 100:0:0 to 90:10) to give Example 11.

Yield: 40 mg

ES mass spectrum: [M+H]$^+$=433

Retention time: 9.40 (HPLC Method 5)

$^1$H NMR (Varian 400 MHz. DMSO-d6; 28° C.) 9.63 (1H, br); 9.19 (1H, br); 9.10 (1H, br); 7.98 (1H, d); 7.93 (1H, dd); 7.31 (1H, m); 7.03 (1H, m); 6.85 (1H, t); 6.80 (1H, dd); 4.20-3.80 (2H, br); 2.96 (3H, m); 2.67 (1H, m); 2.07-2.00 (2H, m); 1.88 (1H, m); 1.66 (3H, m); 1.25 (1H, m).

Synthesis of Example 12

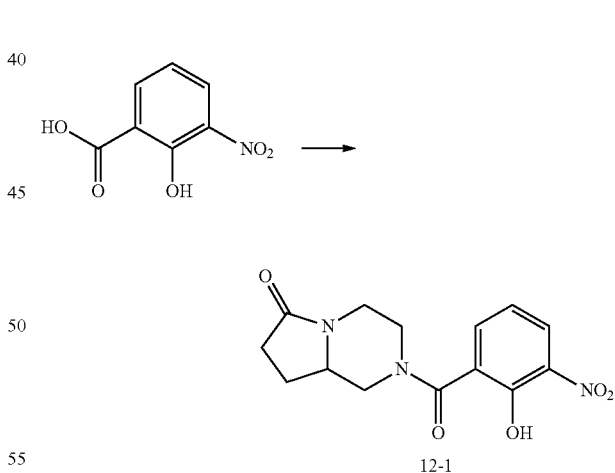

A mixture of 3-nitrosalicyclic acid (5 g, 27.30 mmol), thionyl chloride (25 mL, 137.85 mmol) and N,N-dimethylformamide (two drops) is stirred at 70° C. for 1 h. The solvent is evaporated under vacuum to leave a crude residue. A portion of this (2 g) is dissolved in dichloromethane (7 mL) and the solution cooled to 0° C. Triethylamine (1.5 mL, 10.70 mmol) is added followed by hexahydro-pyrrolo[1,2-a]pyrazin-6-one (500 mg, 3.57 mmol). The mixture is allowed to warm to room temperature and stirred overnight. The solvent is removed under reduced pressure and the crude residue purified by flash chromatography (Silica Gel, gradient: cyclohexane/ethyl acetate from 100:0 to 0:100) to give compound 12-1.

Yield: 900 mg

ES mass spectrum: [M+H]⁺=306

Retention time: 0.74 min (HPLC Method 4)

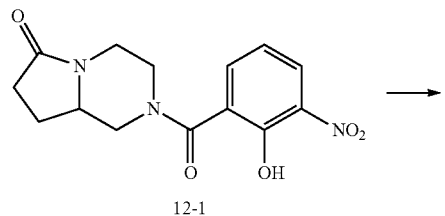

12-1

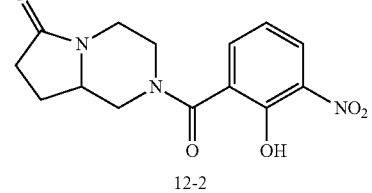

12-2

Compound 12-2 is prepared from compound 12-1 in a manner analogous to that described for compound 1-2.

Yield: 700 mg

ES mass spectrum: [M+H]⁺=275

Retention time HPLC: 0.48 min (HPLC Method 4)

The following compounds are prepared from compound 12-2 in a manner analogous to that described for the preparation of Example 1 with the appropriate isocyanate (Examples 12 and 13) or in a manner analogous to that described for the preparation of Example 9 (Example 14).

| Example | Structure | Analysis |
|---|---|---|
| 12 | 12-3 | ES mass spectrum: [M + H]⁺ = 473 Retention time: 9.72 min (HPLC Method 6) ¹H NMR (Varian Inova 500 MHz. DMSO-d6; 27° C.) 9.67 (1H, br); 9.13 (1H, s); 8.80 (1H, s); 7.94 (1H, m); 7.61 (1H, dd); 7.33 (1H, m); 6.88 (1H, m); 6.87 (1H, t); 6.83 (1H, dd); 3.85 (1H, m); 3.58 (1H, m); 2.80 (2H, m); 2.67 (1H,m); 2.27 (2H, m); 2.09 (1H, m); 1.56 (1H, m); 3 H not observed. |
| 13 | 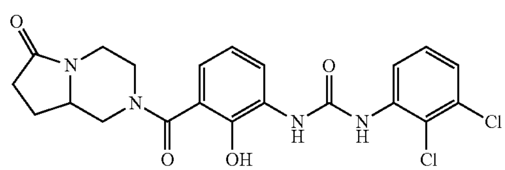 [SMILES: O=C(Nc1cccc(C(=O)N2CCN3C(=O)CCC3C2)c1O)Nc1cccc(Cl)c1Cl] | ES mass spectrum: [M + H]⁺ = 463 Retention time: 10.53 min (HPLC Method 6) ¹H NMR (Varian 400 MHz. DMSO-d6; 28° C.) 9.66 (1H, s); 9.19 (1H, s); 9.11 (1H, s); 8.11 (1H, dd); 7.96 (1H, dd); 7.35-7.26 (2H, m); 6.92-6.84 (2H, m); 3.84 (2H, m); 3.58 (2H, m); 2.81 (2H, m); 2.24 (2H, m); 2.08 (1H, m); 1.55 (1H, m); 1 H not observed. |
| 14 | 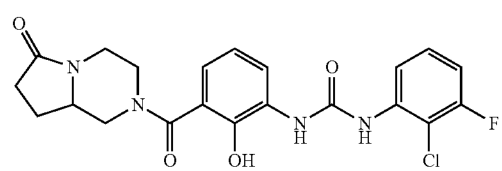 [SMILES: O=C(Nc1cccc(C(=O)N2CCN3C(=O)CCC3C2)c1O)Nc1cccc(F)c1Cl] | ES mass spectrum: [M + H]⁺ = 447 Retention time: 7.85 min (HPLC Method 5) ¹H NMR (Varian 400 MHz. DMSO-d6; 28° C.) 9.47 (1H, br); 9.29 (1H, br); 9.11 (1H, br); 7.97 (2H, m); 7.30 (1H, m); 7.05 (1H, m); 6.89 (1H, t); 6.86 (1H, dd); 3.86 (1H, m); 4.80-4.20 (2H, br); 3.57 (1H, m); 2.79 (2H, m); 2.67 (1H, m); 2.26 (2H, m); 2.09 (1H, m); 1.55 (1H, m). |

Synthesis of Example 15

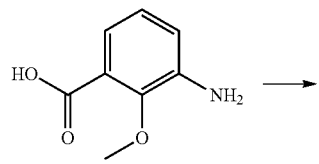

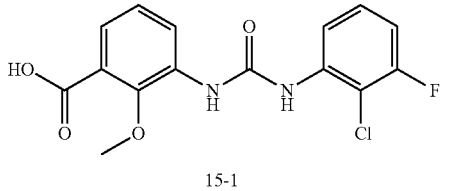

15-1

4-Nitrophenylchloroformate (663 mg, 3.29 mmol) is dissolved in dry dichloromethane (10 mL) and cooled to 0° C. A solution of 2-chloro-3-fluoroaniline (479 mg, 3.29 mmol) and pyridine (355 µL 4.48 mmol) in dry DCM (10 mL) is added dropwise and the mixture stirred for 15 minutes at 0° C. then 1 h at room temperature. 3-Amino-2-methoxybenzoic acid (500 mg, 2.99 mmol) and pyridine (710 µL, 9 mmol) in DCM (10 mL) are added and the mixture stirred for 2 hours. The solvent is removed and the residue purified by flash chromatography (Silica Gel, gradient: dichloromethane/methanol from 100:0 to 75:25) then recrystallised from DCM to give compound 15-1.

Yield: 300 mg
ES mass spectrum: [M+H]⁺=339
Retention time: 5.72 min (HPLC Method 5)

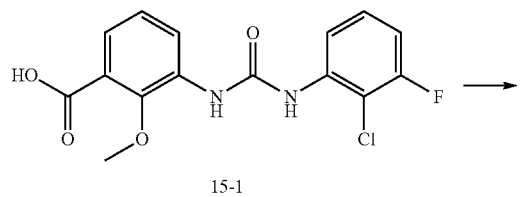

15-1

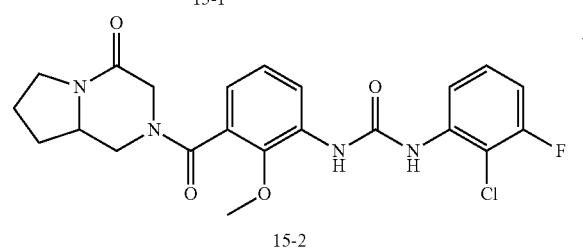

15-2

Compound 15-1 (40 mg, 0.12 mmol) is dissolved in N,N-dimethylformamide (3 mL) and triethylamine (49.38 µL, 0.35 mmol), hexahydro-pyrrolo[1,2-a]pyrazin-4-one (18.21 mg, 0.13 mmol) and HATU (42.39 mg, 0.13 mmol) are added. The reaction mixture is stirred at room for 1 h. Volatiles are removed under reduced pressure and the residue suspended in water (5 mL) and extracted twice with dichloromethane (2×5 mL). The organic layers are combined, dried over MgSO₄ and evaporated under reduced pressure to give compound 15-2.

Yield: 55 mg
ES mass spectrum: [M+H]⁺=461
Retention time: 1.03 min (HPLC method 2)

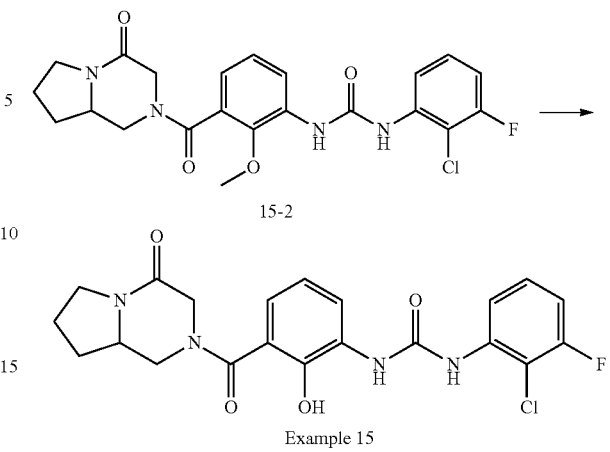

15-2

Example 15

Under nitrogen atmosphere, a solution of compound 15-2 (55 mg, 0.119 mmol) in dry dichloromethane (2 mL) is cooled to 0° C. and borontribromide (1 M in dichloromethane, 1.19 mL, 1.19 mmol) added dropwise. The reaction mixture is stirred at 0° C. for 1 h and then quenched with methanol (1 mL). The reaction mixture is partitioned between NaHCO₃ saturated aqueous solution and dichloromethane and the aqueous layer extracted three times with dichloromethane. The organic layers are combined, dried over MgSO₄, and the solvent removed under vacuum. The residue is purified via semi-preparative reversed phase HPLC to give Example 15.

Yield: 29 mg
ES mass spectrum: [M+H]⁺=447
Retention time: 7.98 min (HPLC Method 5)
¹H NMR (Varian 400 MHz. DMSO-d6; 28° C.) 9.64 (1H, br); 9.20 (1H, br); 9.11 (1H, br); 7.98 (1H, d); 7.33 (1H, dt); 7.03 (1H, dt); 6.56 (2H, s, br); 4.51 (1H, br); 3.76 (2H, br); 3.49 (1H, m); 3.00 (1H, br); 2.10-1.85 (3H, br); 1.44 (2H, m); 2 H not observed.

Synthesis of Example 16

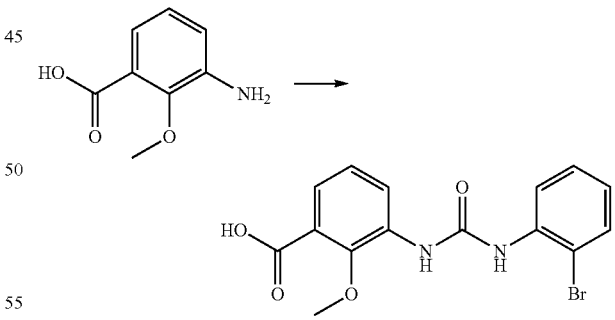

16-1

3-Amino-2-methoxybenzoic acid (1.4 g, 8.4 mmol) is suspended in DCM (50 mL) and 2-bromophenylisocyanate (1.03 mL, 8.4 mmol) added. Methanol is added dropwise until a homogeneous solution is obtained and the mixture is stirred overnight. The solid formed is collected by filtration, washed with DCM and dried to give compound 16-1.

Yield: 1.37 g
ES mass spectrum: [M+H]⁺=363
Retention time: 5.30 min (HPLC Method 5)

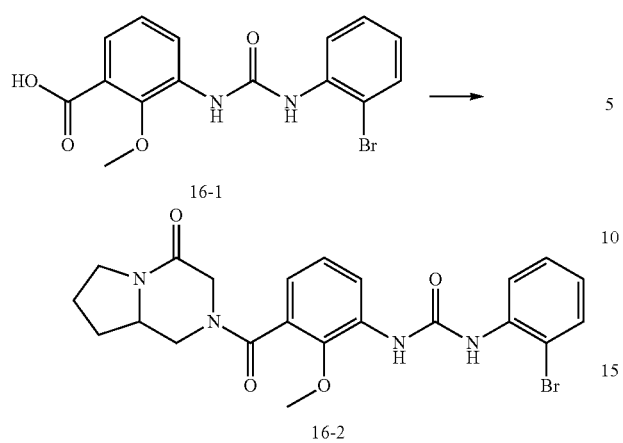

16-1

16-2

Compound 16-1 (100 mg, 0.27 mmol) is dissolved in tetrahydrofuran (4.5 mL) and hexahydro-pyrrolo[1,2-a]pyrazin-4-one (37.85 mg, 0.27 mmol) is added followed by N,N-diisopropylethylamine (46.87 µL, 0.27 mmol) and BOP (119.42 mg, 0.27 mmol). The reaction mixture is stirred at room temperature for 2 days. Two further equivalents of N,N-diisopropylethylamine are added and the mixture stirred at room temperature overnight. The solvent is removed under reduced pressure and the residue partitioned between water and ethyl acetate. The organic layer is washed with NaHCO$_3$ saturated aqueous solution followed by NaCl saturated aqueous solution, then dried over MgSO$_4$ and evaporated under vacuum. The residue is purified by flash chromatography (Silica Gel, ethyl acetate) to give compound 16-2.

Yield: 49.3 mg
ES mass spectrum: [M+H]$^+$=487, 489
Retention time: 0.99 min (HPLC method 2)

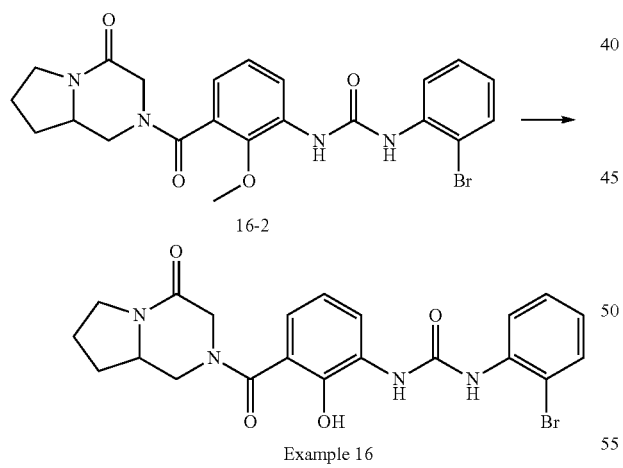

16-2

Example 16

Under nitrogen atmosphere, a solution of compound 16-2 (49 mg, 0.10 mmol) in dry dichloromethane (7 mL) is cooled to 0° C. and borontribromide (1 M in dichloromethane, 1 mL, 1 mmol) added dropwise. The reaction mixture is stirred at room temperature overnight and then methanol added dropwise until a homogeneous solution is obtained. Volatiles are evaporated under reduced pressure, the residue partitioned between water and dichloromethane and the aqueous layer extracted with dichloromethane. The organic layers are combined, dried and the solvent removed under vacuum. The residue is purified by flash chromatography (Silica Gel, ethyl acetate:methanol 95:5) to give Example 16.

Yield: 16 mg
ES mass spectrum: [M+H]$^+$=473
Retention time: 10.14 min (HPLC Method 6)
$^1$H NMR (Varian 400 MHz. DMSO-d6; 28° C.) 9.78 (1H, br); 9.13 (1H, br); 8.81 (1H, br); 7.93 (1H, dd); 7.34 (1H, d); 7.01 (1H, dt); 6.97 (1H, dt); 6.85 (2H; m); 4.80-4.30 (1H, br); 3.95-3.60 (3H, br); 3.44 (1H, m); 3.34 (1H, m); 3.01 (1H, br); 2.05-1.65 (3H, br); 1.40 (1H, m); 1 H not observed.

Synthesis of Example 17

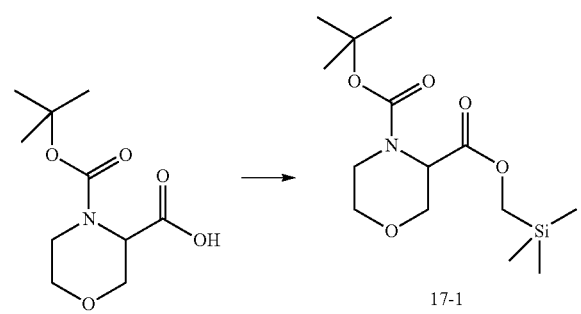 [SMILES: CC(C)(C)OC(=O)N1CCOCC1C(=O)O ; CC(C)(C)OC(=O)N1CCOCC1C(=O)OC[Si](C)(C)C]

17-1

Morpholine-3,4-dicarboxylic acid 4-tert-butyl ester (4 g, 17.3 mmol) is dissolved in dry diethyl ether (40 mL) under nitrogen and trimethylsilyldiazomethane (2 M in diethyl ether, 16 mL, 32 mmol) is added. The mixture is stirred for 2 hours then methanol (4 mL) is added and the mixture stirred overnight. The solvent is evaporated to give crude compound 17-1.

Yield: 5.49 g
EI mass spectrum: [M]$^+$=317
Retention time GC: 10.81 min (GC/MS Method 7)

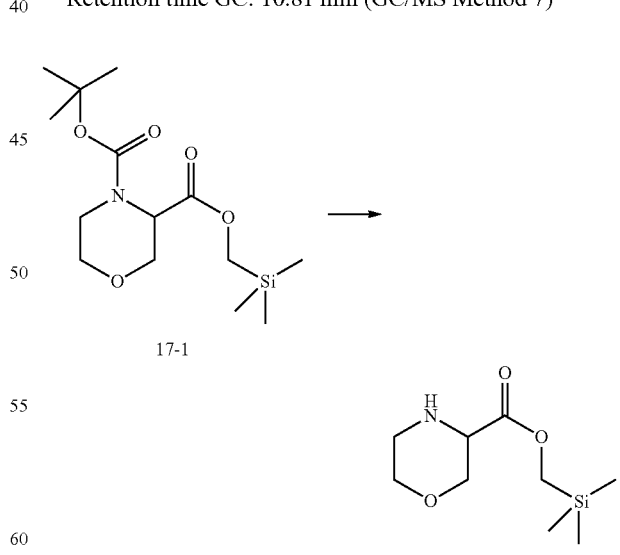

17-1

17-2

Compound 17-1 (5.49 g, 17.3 mmol) is dissolved in DCM (40 mL) and trifluoroacetic acid (10 mL) is added and the mixture stirred for 5 hours. The solution is loaded onto 2×50 g SCX cartridges, washed with methanol (200 mL) and then eluted with 1 M ammonia solution in methanol (200 mL). The solvent is removed under reduced pressure to give crude compound 17-2.

Yield: 3.3 g

EI mass spectrum: $[M]^+=217$

Retention time GC: 8.56 min (GC/MS Method 7)

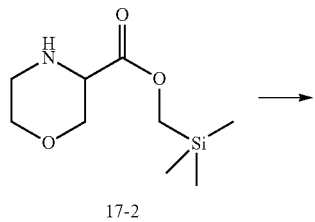

17-2

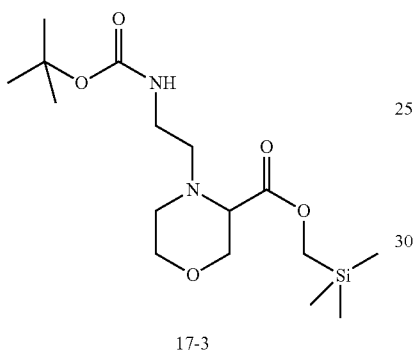

17-3

Compound 17-2 (3.3 g 15.18 mmol) is dissolved in 1,2-dichloroethane (50 mL) under nitrogen atmosphere and tert-butyl-N-(2-oxoethyl)carbamate (3.63 g, 22.78 mmol) and sodium triacetoxyborohydride (9 g, 42.5 mmol) added. The mixture is stirred for 16 hours at room temperature, then 6 hours at 60° C. then 3 days at room temperature. The solution is loaded onto 2×50 g SCX cartridges, washed with methanol (200 mL) and then eluted with 1 M ammonia solution in methanol (250 mL). The solvent is removed under reduced pressure to give crude compound 17-3.

Yield: 2.82 g

EI mass spectrum: $[M]^+=360$

Retention time GC: 13.06 min (GC/MS Method 7)

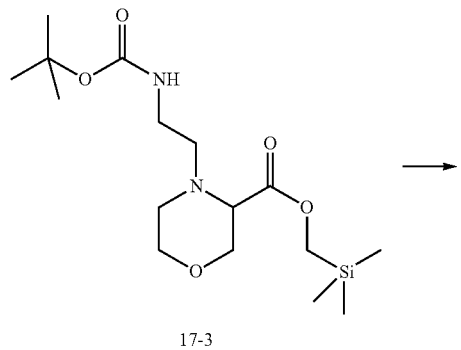

17-3

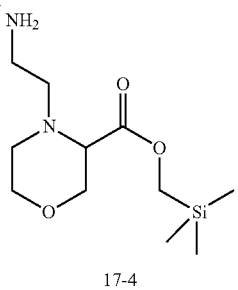

17-4

Compound 17-3 (2.82 g, 7.82 mmol) is dissolved in DCM (40 mL) and trifluoroacetic acid (20 mL) is added at 0° C. The mixture is stirred at 0° C. for 30 minutes then at room temperature for 4 hours. The solution is loaded onto 2×50 g SCX cartridges, washed with methanol (200 mL) and then eluted with 1 M ammonia solution in methanol (250 mL). The solvent is removed under reduced pressure to give crude compound 17-4.

Yield: 2.0 g

ES mass spectrum: $[M-OCH_2SiMe_3]^+=157$

Retention time: 1.24 min (HPLC Method 5)

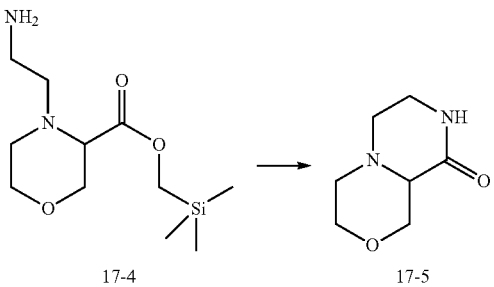 [SMILES: C[Si](C)(C)COC(=O)C1COCCN1CCN ; O=C1NCCN2CCOCC12]

17-4      17-5

Compound 17-4 (2.0 g, 7.68 mmol) is dissolved in methanol (80 mL) and heated at 40° C. for 3 hours. The solvent is removed and the residue purified by flash chromatography (Silica Gel, dichloromethane:methanol 95:5) to give compound 17-5.

Yield: 480 mg

EI mass spectrum: $[M]^+=156$

Retention time GC: 9.57 min (GC/MS Method 7)

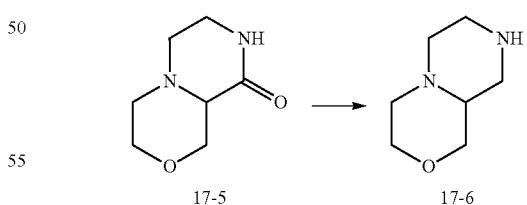

17-5      17-6

Compound 17-5 (150 mg, 0.96 mmol) is suspended in dry THF (5 mL) and borane THF complex (1 M in THF, 9.6 mL, 9.6 mmol) added. The mixture is heated at 90° C. for 28 hours. The mixture is loaded onto a 10 g SCX cartridge, washed with methanol and then eluted with 2 M ammonia solution in methanol. The solvent is removed under reduced pressure, the residue cooled in an ice bath and hydrogen chloride (6 M in dioxane, 10 mL) added. The mixture is heated at 60° C. for 4 hours and the solvent removed. The mixture is loaded onto a 10 g SCX cartridge, washed with methanol and then eluted with 1 M ammonia solution in methanol. The solvent is removed under reduced pressure to give compound 17-6.

Yield: 70 mg
EI mass spectrum: [M]$^+$=142
Retention time GC: 6.77 min (GC/MS Method 7)

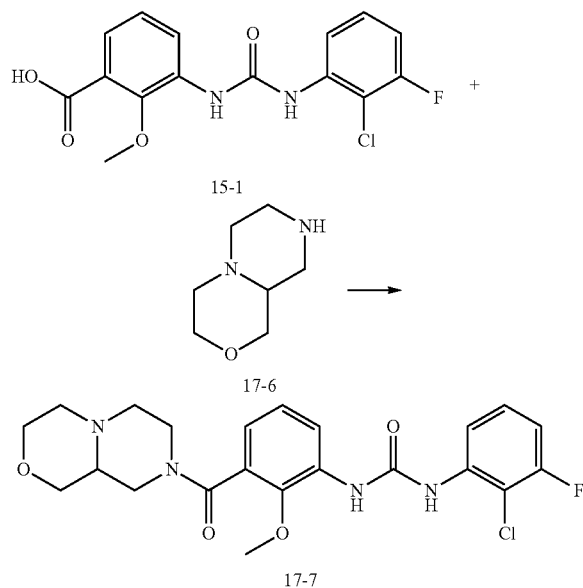

Compound 15-1 (50 mg, 0.15 mmol), compound 17-6 (23 mg, 0.16 mmol), HATU (62 mg, 0.16 mmol) and triethylamine (55 µL 0.39 mmol) are combined in DMF (3 mL) and stirred for 1 hour. The solvent is removed under vacuum, the residue suspended in water (5 mL) and extracted with DCM (2×5 mL). The combined organic extracts are dried and the solvent removed to give compound 17-7

Yield: 60 mg
ES mass spectrum: [M+H]$^+$=463
Retention time HPLC: 0.96 min (HPLC method 1)

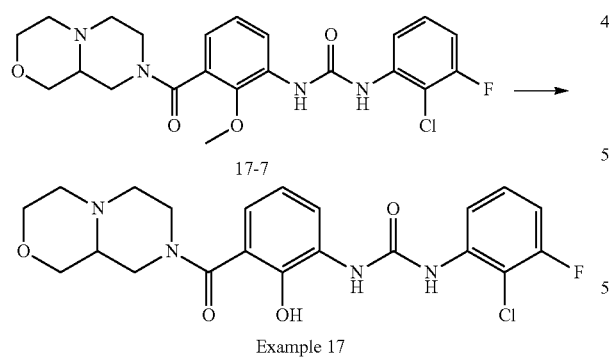

Compound 17-7 (60 mg, 0.13 mmol) is dissolved in dry DCM (3 mL) and borontribromide (1 M in DCM, 1.3 mL, 1.3 mmol) is added at 0° C. The mixture is stirred for 90 minutes, the solvent is removed and the residue purified by semi-preparative HPLC to give Example 17.

Yield: 10 mg
ES mass spectrum: [M+H]$^+$=449
Retention time HPLC: 8.13 min (HPLC Method 5).

$^1$H NMR (Varian 400 MHz. DMSO-d6; 28° C.) 10.25 (1H, br); 9.69 (1H, s); 9.19 (1H, s); 9.10 (1H, s); 7.97 (2H, m); 7.32 (1H, t); 7.06 (1H, t); 6.90 (2H, m); 4.20-2.89 (12H, br).

Synthesis of Example 18

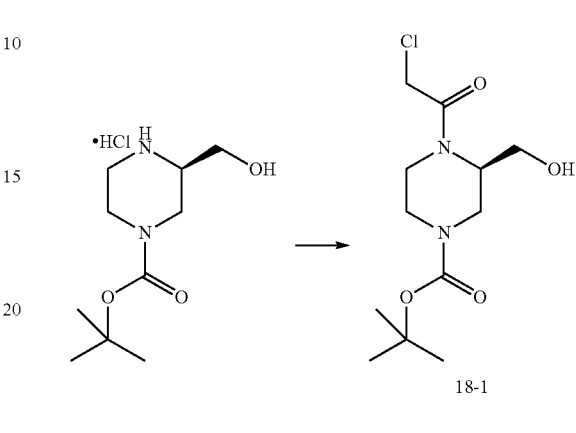

(R)-4-N-Boc-2-Hydroxymethyl-piperazine hydrochloride (1 g, 3.96 mmol) and triethylamine (1.65 mL, 11.87 mmol) are suspended in DCM (5 mL) and cooled to 0° C. Chloroacetyl chloride (0.35 mL, 4.35 mmol) is added and the mixture stirred overnight at room temperature. The solvent is evaporated under reduced pressure to give crude compound 18-1.

Yield: 1.2 g
ES mass spectrum: [M-tBu+H]$^+$=237
Retention time HPLC: 0.87 min (HPLC method 1).

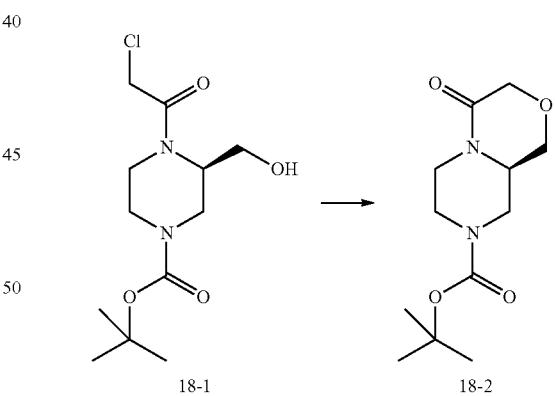

Compound 18-1 (1.2 g, 4.1 mmol) is suspended in THF (7 mL) and potassium tert-butoxide (552 mg, 4.92 mmol) is added. The mixture is stirred for 4 hours at room temperature and then the solvent is removed under reduced pressure. The residue is purified by flash chromatography (Silica Gel, gradient, cyclohexane:ethyl acetate, 100:0-0:100) to give compound 18.2.

Yield: 410 mg
EI mass spectrum: [M]$^+$=256
Retention time GC: 11.91 min (GC/MS Method 7).

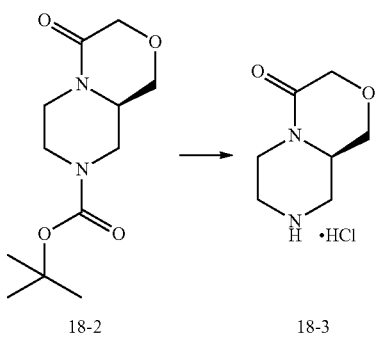 [SMILES: CC(C)(C)OC(=O)N1CCN2C(=O)COC[C@H]2C1 ; O=C1COC[C@H]2CNCCN12 ; Cl]

Compound 18-2 (410 mg, 1.6 mmol) is suspended in DCM (7 mL) and hydrogen chloride (4 M in dioxane, 20 mL) is added. The mixture is stirred for 90 minutes and then the solvent evaporated under reduced pressure to give compound 18-3.

Yield: 300 mg

ES mass spectrum: [M+H]⁺=157

Retention time HPLC: 0.25 min (HPLC method 1).

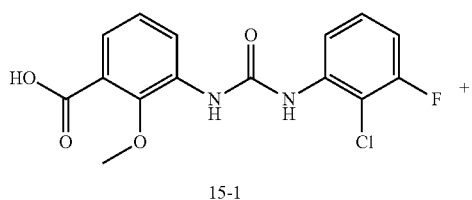

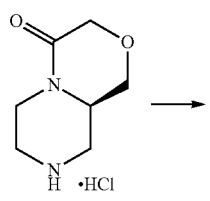

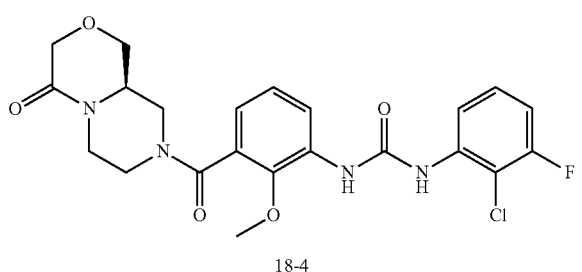

Compounds 18-3 (31 mg, 0.16 mmol) and 15-1 (50 mg, 0.15 mmol) are reacted together in a manner analogous to that described of compound 17-7 to give compound 18-4.

Yield: 50 mg

ES mass spectrum: [M+H]⁺=477

Retention time HPLC: 0.99 min (HPLC method 2)

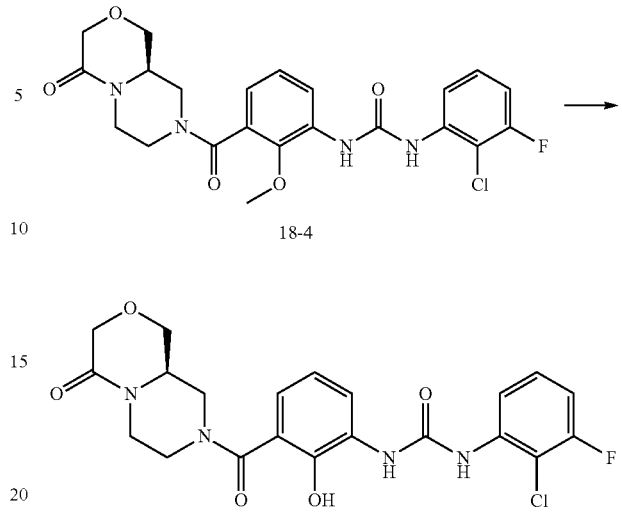

Compound 18-4 is treated in a manner analogous to that described for the preparation of example 17 to give Example 18.

Yield: 4 mg

ES mass spectrum: [M+H]⁺=463

Retention time HPLC: 9.97 min (HPLC Method 6).

¹H NMR (Varian Inova 500 MHz. DMSO-d6; 27° C.) 9.22 (1H, br); 9.12 (1H, br); 7.97 (2H, m); 7.31 (1H, dt); 7.05 (1H, dt); 6.85 (2H, m); 4.38 (1H; m); 4.05 (2H, s); 4.04 (1H, m); 3.63 (2H, m); 3.05-2.92 (3H, m); 2.76 (2H, m); 1 H not observed.

Synthesis of Example 19

(S)-4-N-Boc-2-Hydroxymethyl-piperazine hydrochloride (1 g, 3.96 mmol) is treated in a manner analogous to that described for the synthesis of compound 18-1 to give compound 19-1.

Yield: 1.2 g

ES mass spectrum: [M-tBu+H]⁺=237

Retention time HPLC: 0.87 min (HPLC method 1).

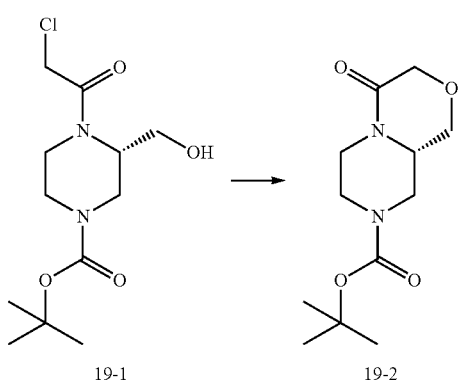 [SMILES: CC(C)(C)OC(=O)N1CCN(C(=O)CCl)[C@H](CO)C1 ; CC(C)(C)OC(=O)N1CCN2C(=O)COC[C@@H]2C1]

Compound 19-1 (1 g, 3.42 mmol) is treated in a manner analogous to that described for the synthesis of compound 18-2 to give compound 19-2.

Yield: 500 mg

EI mass spectrum: $[M]^+=256$

Retention time GC: 11.91 min (GC/MS Method 7).

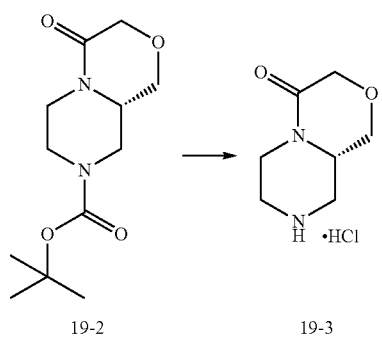 [SMILES: CC(C)(C)OC(=O)N1CCN2C(=O)COC[C@@H]2C1 ; O=C1COC[C@@H]2CNCCN12 ; Cl]

Compound 19-2 (500 mg, 1.95 mmol) is treated in a manner analogous to that described for the synthesis of compound 18-3 to give compound 19-3.

Yield: 370 mg

ES mass spectrum: $[M+H]^+=157$

Retention time HPLC: 0.25 min (HPLC method 1).

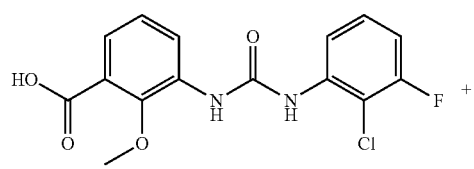

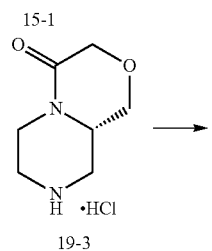

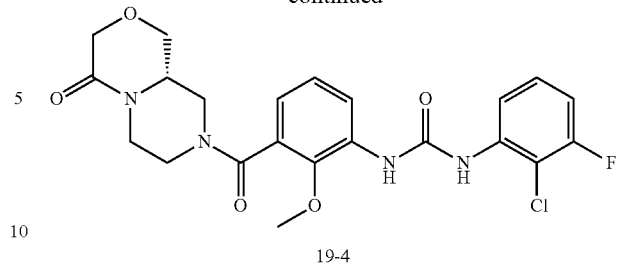

Compounds 19-3 (31 mg, 0.16 mmol) and 15-1 (50 mg, 0.15 mmol) are allowed to react together in a manner analogous to that described for the preparation of compound 17-7 to give compound 19-4.

Yield: 50 mg

ES mass spectrum: $[M+H]^+=477$

Retention time HPLC: 0.99 min (HPLC method 2)

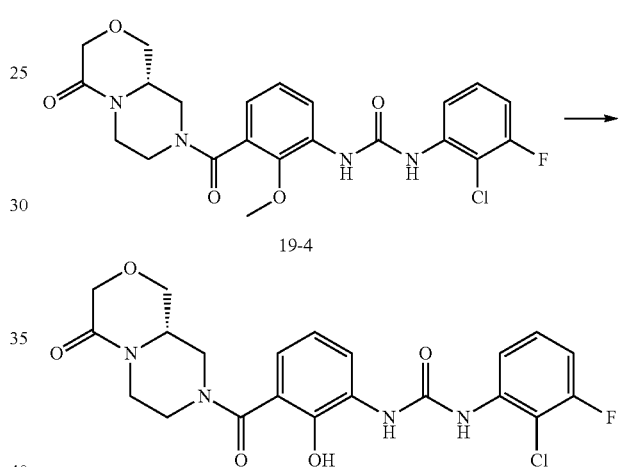

Compound 19-4 (50 mg, 0.10 mmol) is treated in a manner analogous to that described for the preparation of Example 17 to give Example 19.

Yield: 5 mg

ES mass spectrum: $[M+H]^+=463$

Retention time HPLC: 9.97 min (HPLC Method 6).

$^1$H NMR (Varian Inova 500 MHz. DMSO-d6; 27° C.) 9.45 (1H, br); 9.21 (1H, br); 9.12 (1H, br); 7.95 (2H, dd); 7.31 (1H, m); 6.88 (1H, dt); 6.85 (2H, m); 4.39 (2H; m); 4.05 (2H, s); 4.02 (1H, m); 3.64-3.51 (3H, br); 3.05-2.75 (3H, m)

Synthesis of Example 20

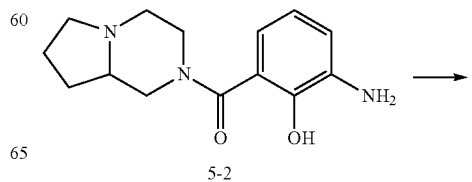

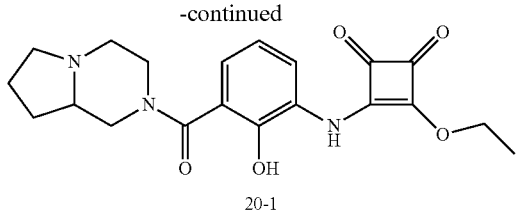
20-1

Compound 5-2 (70 mg, 0.27 mmol) and 3,4-diethoxy-cyclobut-3-ene-1,2-dione (59.45 µL, 0.40 mmol) in ethanol (10 mL) are heated under reflux for 2 h. The solvent is removed under reduced pressure and the crude residue is purified by flash chromatography (Silica Gel, gradient: cyclohexane/ethyl acetate from 100:0 to 0:100) to give compound 20-1.
Yield: 98 mg
ES mass spectrum: [M+H]$^+$=386
Retention time HPLC: 0.72 min (HPLC method 2)

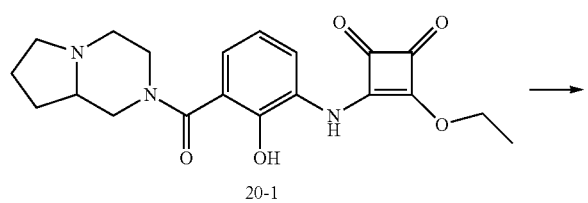
20-1

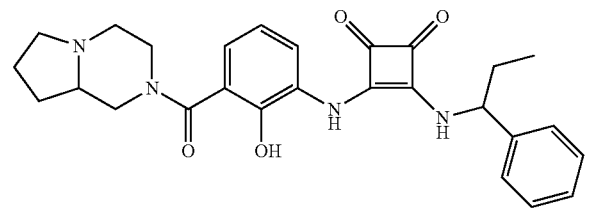
Example 20

Compound 20-1 (25 mg, 0.06 mmol) and alpha-ethylbenzylamine (11 µL, 0.08 mmol) are dissolved in ethanol (3 mL) and refluxed for 1 hour. The solvent is removed and the residue purified by semi-preparative HPLC-MS to give Example 20.
Yield: 17 mg
ES mass spectrum: [M+H]$^+$=475
Retention time HPLC: 8.18 min (HPLC Method 5)
$^1$H NMR (Varian 400 MHz. DMSO-d6; 28° C.) 8.92-9.90 (2H, br); 8.68 (1H, d); 7.75 (1H, d); 7.30-7.40 (5H, m); 6.84 (2H, m); 5.10 (1H, m); 3.58-4.22 (3H, br); 2.97 (3H, m); 2.05 (2H, m); 1.91 (3H, m); 1.67 (3H, m); 1.27 (1H, m); 0.87 (3H, t).

Synthesis of Example 21

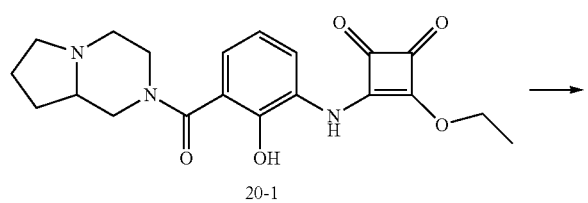
20-1

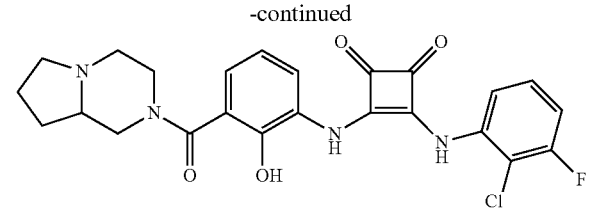
Example 21

Compound 20-1 (30 mg, 0.078 mmol), 4-dimethylaminopyridine (0.95 mg, 0.008 mmol) and 2-chloro-3-fluoro-phenylamine (113 mg, 0.78 mmol) are dissolved in ethanol (2 mL) and heated under reflux for 5 days. The solvent is removed under vacuum and the crude material purified by semi-preparative reversed phase HPLC to give Example 21.
Yield: 4 mg
ES mass spectrum: [M+H]$^+$=485
Retention time HPLC: 7.73 min (HPLC Method 5)
$^1$H NMR (Varian 400 MHz. DMSO-d6; 28° C.) 10.08 (3H, br); 7.62 (1H, dd); 7.40 (2H, m); 7.15 (1H, br); 6.89 (2H, br s); 2.98 (4H, m); 2.06 (2H, m); 1.89 (1H, m); 1.68 (4H, m); 1.28 (2H, m).

Synthesis of Example 22

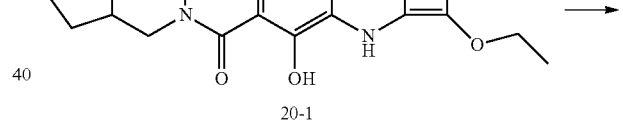
20-1

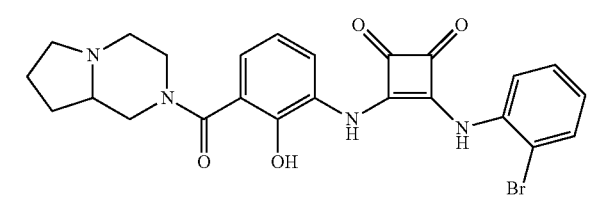
Example 22

Compound 20-1 (30 mg, 0.078 mmol), is reacted with 2-bromoaniline in a manner analogous to that used for the synthesis of example 21 to give Example 22.
Yield: 6 mg
ES mass spectrum: [M+H]$^+$=511
Retention time HPLC: 7.73 min (HPLC Method 5)
$^1$H NMR (Varian 400 MHz. DMSO-d6; 28° C.) 10.03 (3H, br); 7.64 (2H, m); 7.47 (1H, d); 7.37 (1H, t); 7.07 (1H, m);

6.88 (2H, br); 2.97 (3H, m); 2.05 (2H, m); 1.86 (1H, m); 1.69 (3H, m); 1.28 (1H, m); 3H not observed.

m); 2.66 (1H, br); 2.10-2.05 (3H, m); 1.90 (3H, m); 1.66 (3H, m); 1.23 (1H, m); 0.91 (3H, t)

Synthesis of Example 23

Synthesis of Example 24

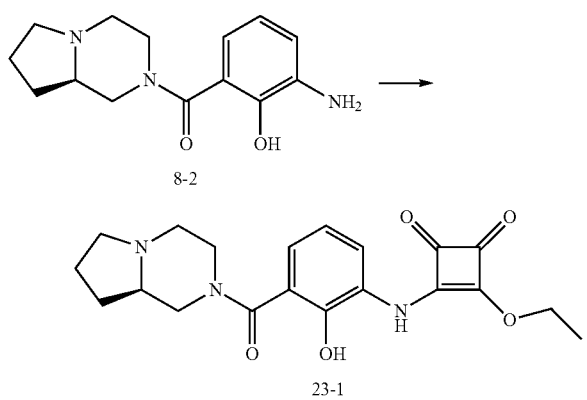 [SMILES: Nc1cccc(C(=O)N2CCN3CCC[C@@H]3C2)c1O ; CCOc1c(Nc2cccc(C(=O)N3CCN4CCC[C@@H]4C3)c2O)c(=O)c1=O]

8-2

23-1

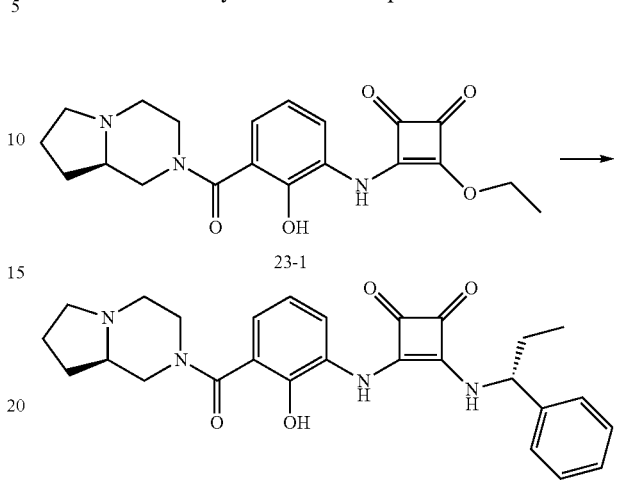

23-1

Example 24

Compound 8-2 (250 mg, 0.96 mmol) is treated in a manner analogous to that used for the synthesis of compound 20-1 to give compound 23-1.

Yield: 280 mg

ES mass spectrum: [M+H]$^+$=386

Retention time HPLC: 6.27 min (HPLC Method 5)

Compound 23-1 (50 mg, 0.13 mmol) is reacted with (R)-1-phenylpropylamine (24 µL, 0.17 mmol) in a manner analogous to that used for the synthesis of example 20 to give Example 24.

Yield: 46 mg

ES mass spectrum: [M+H]$^+$=475

Retention time HPLC: 8.00 min (HPLC Method 5)

$^1$H NMR (Varian 400 MHz. DMSO-d6; 28° C.) 9.34 (1H, br); 8.68 (1H, dd); 7.75 (1H, dd); 7.40-7.30 (5H, m); 6.87 (1H, t); 6.82 (1H, dd); 5.11 (1H, m); 4.4-3.85 (2H, br); 2.95 (3H, m); 2.66 (1H, br); 2.11-2.03 (3H, m); 1.90 (4H, m); 1.66 (3H, m); 1.25 (1H, m); 0.91 (3H, t)

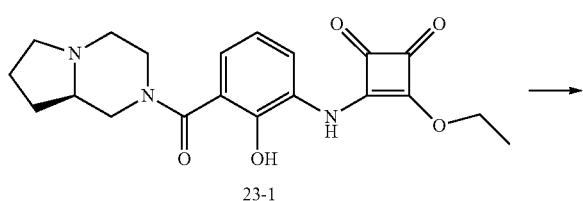

23-1

Synthesis of Example 25

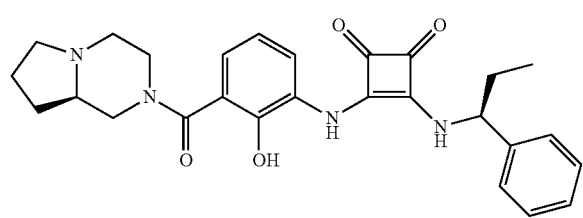

Example 23

Compound 23-1 (50 mg, 0.13 mmol) is reacted with (S)-1-phenylpropylamine (24 µL, 0.17 mmol) in a manner analogous to that used for the synthesis of example 20 to give Example 23

Yield: 49 mg

ES mass spectrum: [M+H]$^+$=475

Retention time HPLC: 8.00 min (HPLC Method 5)

$^1$H NMR (Varian 400 MHz. DMSO-d6; 28° C.) 9.33 (1H, br); 8.70 (1H, d); 7.75 (1H, d); 7.40-7.27 (5H, m); 6.87 (1H, t); 6.82 (1H, dd); 5.11 (1H, m); 4.30-3.73 (2H, br); 2.95 (3H,

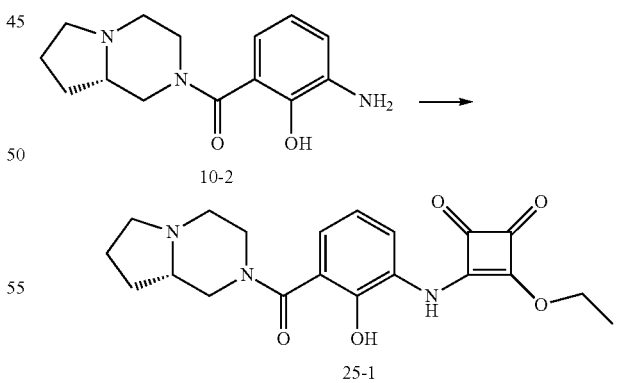

10-2

25-1

Compound 10-2 (250 mg, 0.96 mmol) is treated in a manner analogous to that used for the synthesis of compound 20-1 to give compound 25-1.

Yield: 318 mg

ES mass spectrum: [M+H]$^+$=386

Retention time HPLC: 6.15 min (HPLC Method 5)

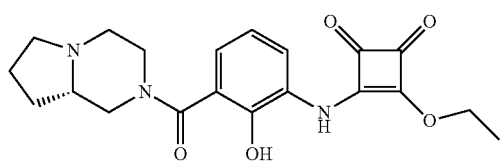

25-1

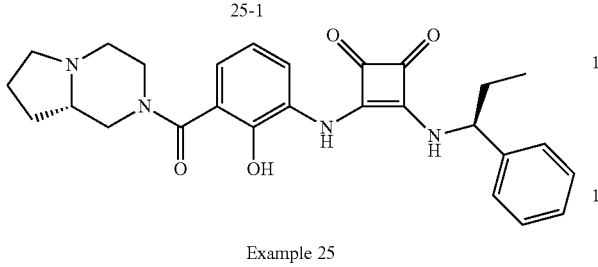

Example 25

Compound 25-1 (50 mg, 0.13 mmol) is allowed to react with (S)-1-phenylpropylamine (24 μL, 0.17 mmol) in a manner analogous to that used for the synthesis of example 20 to give Example 25.

Yield: 48 mg

ES mass spectrum: $[M+H]^+$=475

Retention time HPLC: 8.00 min (HPLC Method 5)

$^1$H NMR (Varian 400 MHz. DMSO-d6; 28° C.) 9.35 (1H, br); 8.70 (1H, d); 7.75 (1H, d); 7.40-7.27 (5H, m); 6.87 (1H, t); 6.82 (1H, dd); 5.12 (1H, m); 4.20-3.70 (2H, br); 2.98 (3H, m); 2.66 (1H, br); 2.10-2.05 (3H, m); 1.90 (3H, m); 1.66 (3H, m); 1.24 (1H, m); 0.91 (3H, t)

Synthesis of Example 26

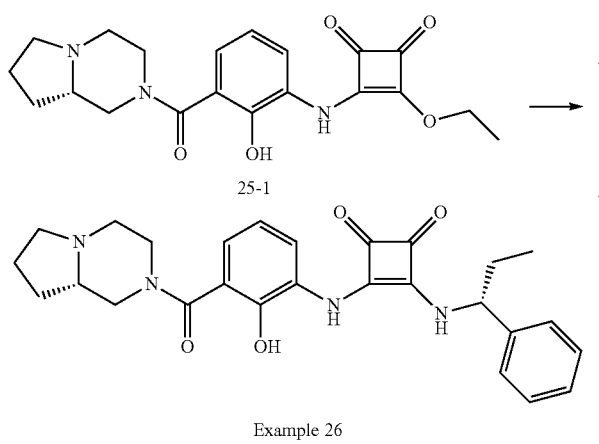

Example 26

Compound 25-1 (50 mg, 0.13 mmol) is reacted with (R)-1-phenylpropylamine (24 μL, 0.17 mmol) in a manner analogous to that used for the synthesis of example 20 to give Example 26.

Yield: 47 mg

ES mass spectrum: $[M+H]^+$=475

Retention time HPLC: 8.02 min (HPLC Method 5)

$^1$H NMR (Varian 400 MHz. DMSO-d6; 28° C.) 9.83 (1H, br); 9.34 (1H, br); 8.69 (1H, d); 7.76 (1H, d); 7.45-7.25 (5H, m); 6.87 (1H, t); 6.82 (1H, dd); 5.12 (1H, m); 4.43-3.67 (2H, br); 2.95 (3H, m); 2.66 (1H, br); 2.11-2.04 (2H, m); 1.90 (3H, m); 1.66 (3H, m); 1.24 (1H, m); 0.91 (3H, t)

Synthesis of Example 27

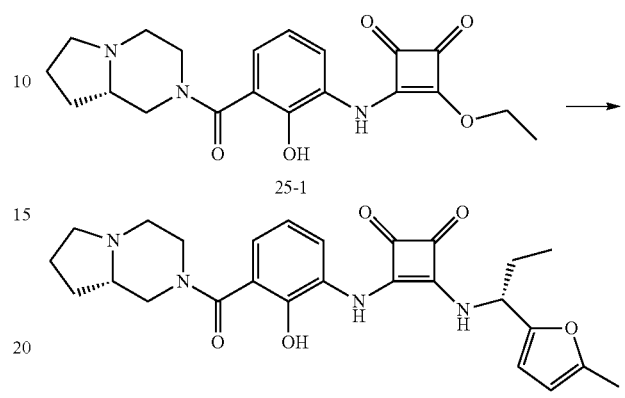

Example 27

Compound 25-1 (50 mg, 0.13 mmol) is reacted with (R)-1-(5-methyl-furan-2-yl)propylamine (22 mg, 0.16 mmol, Journal of Medicinal Chemistry, 2006, vol. 49, p. 7603-7606) in a manner analogous to that used for the synthesis of example 20 to give Example 27.

Yield: 30 mg

ES mass spectrum: $[M+H]^+$=479

Retention time HPLC: 8.23 min (HPLC Method 5)

$^1$H NMR (Varian 400 MHz. DMSO-d6; 28° C.) 9.33 (1H, br); 8.68 (1H, d); 7.77 (1H, d); 6.87 (1H, t); 6.79 (1H, dd); 6.24 (1H, d); 6.04 (1H, dt); 5.14 (1H, m); 4.70-3.80 (2H, br); 2.97 (3H, m); 2.67 (1H, m); 2.26 (3H, s); 2.10-1.80 (5H, m); 1.67 (1H, m); 1.27 (1H, m); 0.92 (3H, t).

Synthesis of Example 28

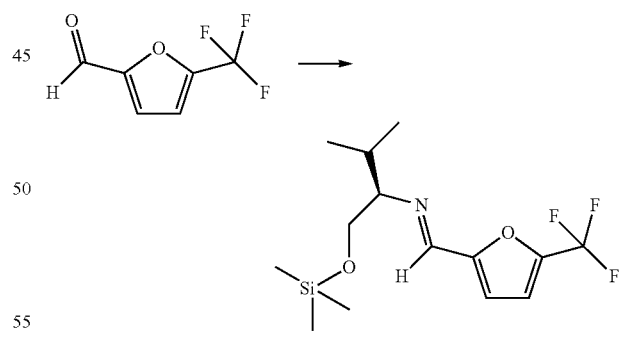

28-1

5-Trifluoromethyl-2-furaldehyde (998 mg, 6.08 mmol), (R)-2-amino-3-methyl-1-butanol (627 mg, 6.08 mmol) and magnesium sulphate (3.02 g, 25.05 mmol) are suspended in dry DCM (9 mL) at 0° C. and stirred for 2 hours at 0° C. followed by overnight at room temperature. The mixture is passed through a filter and the solvent removed under reduced pressure. The residue is dissolved in DCM (11 mL) and chlorotrimethylsilane (845 μL, 6.69 mmol) and triethylamine (932 μL, 6.69 mmol) are added. The mixture is stirred overnight, passed through a filter and the solvent removed. The residue is suspended in 1:1 diethyl ether/n-hexane (50 mL), passed through a filter and the solvent removed to give compound 28-1.

Yield: 1.88 g
ES mass spectrum: [M+H]⁺=322
Retention time HPLC: 1.63 min (HPLC method 2)

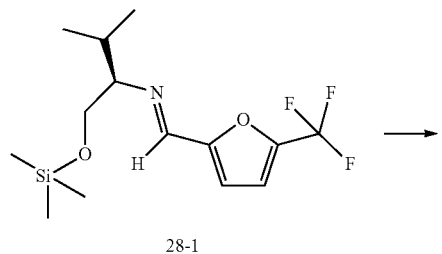

28-1

Iodoethane (568 µL, 7.03 mmol) is dissolved in dry diethyl ether (11 mL) under an argon atmosphere, cooled to −78° C. and tert-butyl lithium (1.7M in pentane, 8.27 mmol, 14.06 mmol) is added dropwise with cooling. After 10 minutes the mixture is warmed to room temperature, stirred for 1 hour and then cooled to −70° C. Compound 28-1 (1.88 g, 5.9 mmol) in dry diethyl ether (8 mL) is added dropwise, the mixture is stirred at −70° C. for 90 minutes then hydrochloric acid (1M, 15 mL) is added. The mixture is warmed to room temperature, the phases separated and the aqueous phase washed with diethyl ether. The aqueous phase is basified with 32% NaOH solution and extracted with diethyl ether. The organic extracts are dried over magnesium sulphate and the solvent removed to give compound 28-2.

Yield: 516 mg
ES mass spectrum: [M+H]⁺=280
Retention time HPLC: 0.85 min (HPLC method 1)

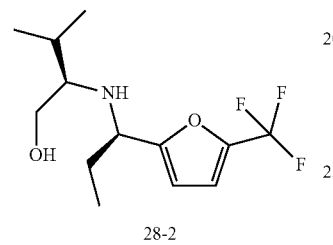

28-2

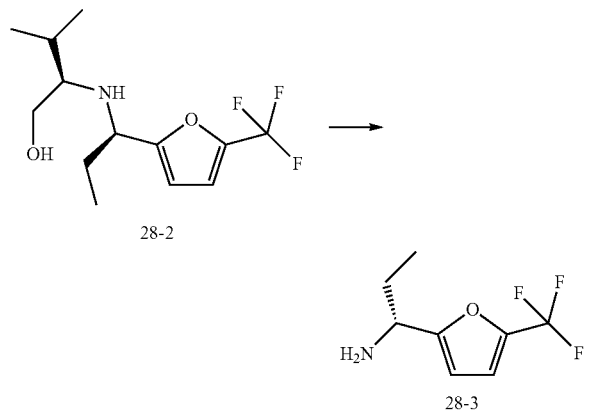

28-3

Compound 28-2 (516 mg, 1.85 mmol) is dissolved in methanol (8 mL), methylamine (40% in water, 2.46 mL), periodic acid (1.38 g, 6.04 mmol) and water (2.5 mL) are added and the mixture stirred for 3 hours. The mixture is diluted with water and extracted with diethyl ether. The organic extracts are dried over magnesium sulphate and concentrated under slightly reduced pressure to give crude compound 28-3 as a mixture with diethyl ether.

Yield: 530 mg
ES mass spectrum: [M-NH3]⁺=177
Retention time HPLC: 0.73 min (HPLC method 1)

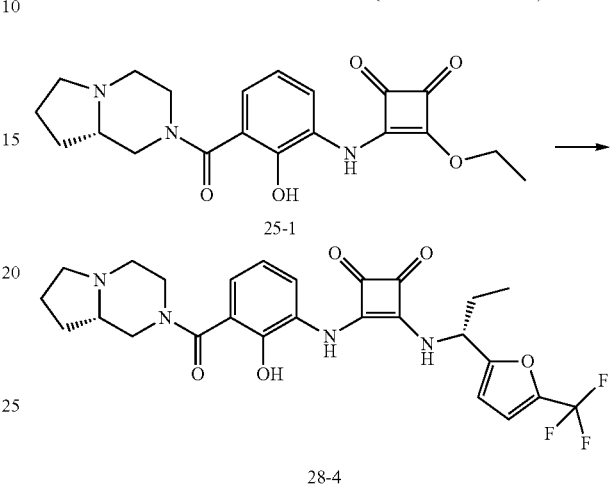

25-1

28-4

Compound 25-1 (45 mg, 0.12 mmol) is reacted with compound 28-3 (60 mg, 0.13 mmol) in a manner analogous to that used for the synthesis of example 20 to give Example 28.

Yield: 23 mg
ES mass spectrum: [M+H]⁺=533
Retention time HPLC: 7.05 min (HPLC Method 6)
¹H NMR (Varian 400 MHz. DMSO-d6; 28° C.) 9.30 (1H, br); 8.72 (1H,br); 7.77 (1H,d); 7.21 (1H,d); 6.84 (2H,m); 6.65 (1H,d); 5.28 (1H,m); 3.60-4.46 (4H,br); 2.97 (3H,m); 1.89-2.04 (5H,m); 1.68 (3H,m); 0.94 (3H,t); 1H not observed.

Synthesis of Example 29

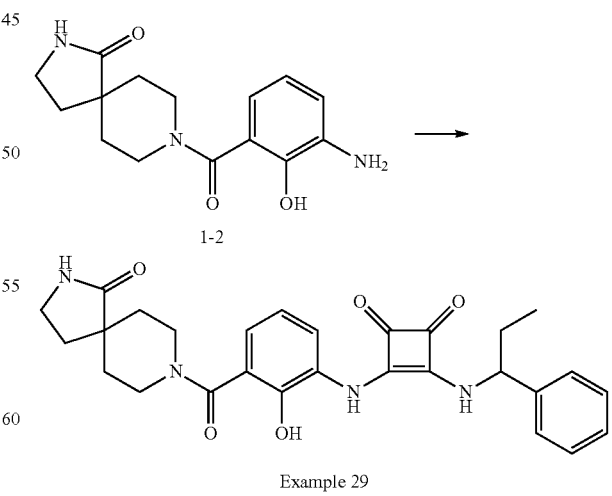

1-2

Example 29

Compound 1-2 (20 mg, 0.069 mmol) and 3,4-Diethoxy-3-cyclobutene-1,2-dione (15.34 µL, 0.104 mmol) in ethanol (2 mL) are heated under reflux. After 1 h, 1-Phenyl-propylamine (39.85 μL, 0.28 mmol) is added and the solution refluxed for further 30 min. The volatiles are removed under vacuum and the crude material is purified via semi-preparative reversed phase HPLC to give Example 29.

Yield: 7 mg
ES mass spectrum: [M+H]⁺=503
Retention time HPLC: 7.23 min (HPLC Method 5)
¹H NMR (Varian 400 MHz. DMSO-d6; 28° C.) 9.53 (1H, br); 8.68 (1H,br); 7.74 (1H,br); 7.57 (1H,s); 7.38 (4H,m); 7.28 (1H,m); 6.83 (2H,br); 5.08 (1H,br m); 3.90 (2H,br); 3.18 (2H,m); 3.08 (2H,m); 1.94 (4H,m); 1.65 (2H,m); 1.39 (2H, m); 0.92 (3H,t).

Yield: 22 mg
ES mass spectrum: [M+H]⁺=489
Retention time HPLC: 6.68 min (HPLC Method 5)
¹H NMR (Varian Inova 500 MHz. DMSO-d6; 27° C.) 9.85 (1H, s); 9.29 (1H, s); 8.67 (1H, d); 7.79 (1H, d); 7.43-7.33 (4H, m); 7.31 (1H, m); 6.91 (1H, t); 6.86 (1H, dd); 5.12 (1H,m); 4.80-4.20 (1H, br); 3.85 (1H, m); 3.57 (1H, m); 2.79 (2H,m); 2.67 (1H,m); 2.26 (2H, m); 2.07 (1H, m); 1.92 (2H, m); 1.55 (1H, m); 0.90 (3H, t).

Synthesis of Example 30

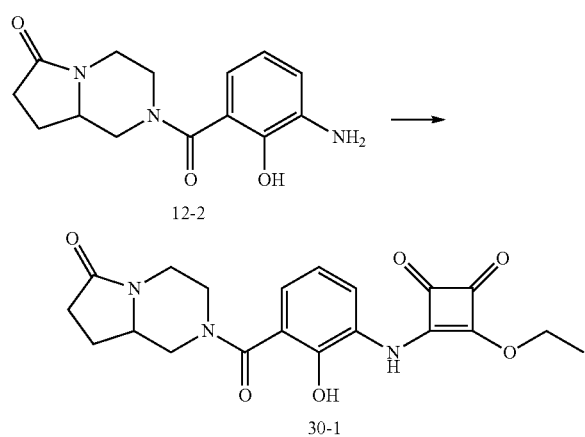

Compound 12-2 (450 mg, 1.63 mmol) is treated in a manner analogous to that used for the synthesis of compound 20-1 to give compound 30-1.
Yield: 200 mg
ES mass spectrum: [M+H]⁺=400
Retention time HPLC: 0.73 min (HPLC method 1)

Synthesis of Example 31

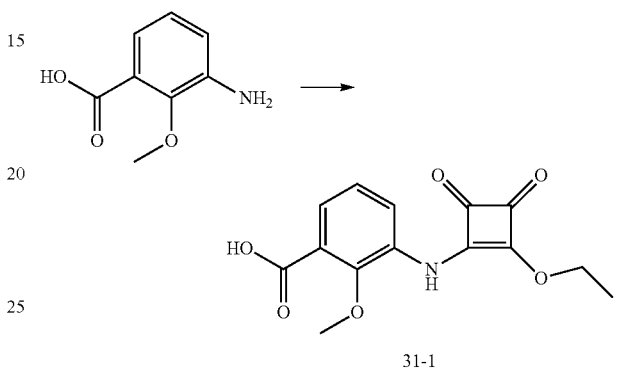

A mixture of 3-amino-2-methoxy-benzoic acid (500 mg, 2.99 mmol), 3,4-diethoxy-cyclobut-3-ene-1,2-dione (531 μL, 3.59 mmol) and triethylamine (500 μL, 3.59 mmol) in ethanol (5 mL) are heated under reflux for 1 h. Volatiles are removed under reduced pressure and the residue taken up with 1 M NaOH in water and ethyl acetate. The aqueous layer is separated, washed twice with ethyl acetate, acidified with concentrated HCl to pH=2 and then extracted three times with ethyl acetate. The organic layers are combined, dried over MgSO4, and the solvent is removed under vacuum to give compound 31-1.
Yield: 860 mg
ES mass spectrum: [M+H]+=292
Retention time HPLC: 0.56 min (HPLC method 2).

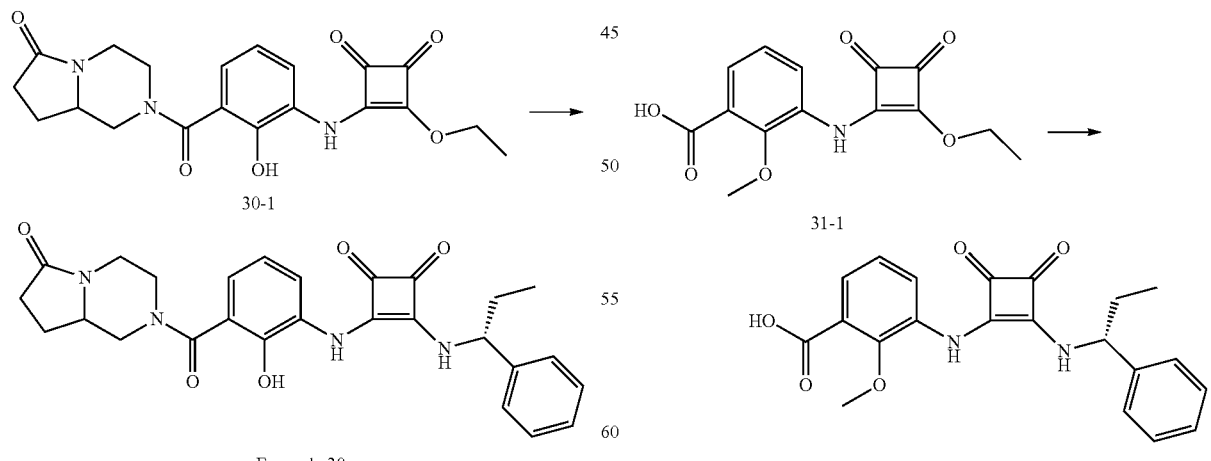

Compound 30-1 (50 mg, 0.13 mmol) is reacted with (R)-1-phenylpropylamine (23 mL, 0.16 mmol) in a manner analogous to that used for the synthesis of compound 20-2 to give Example 30.

To a solution of compound 31-1 (860 mg, 2.95 mmol) in ethanol (5 mL), triethylamine (493.86 μL, 3.54 mmol) and (R)-1-phenyl-propylamine (467 μL, 3.25 mmol) are added and the mixture is heated at reflux for 30 min. The solvent is removed under vacuum and the residue dissolved in ethyl acetate and washed twice with 0.2 M HCl in water. The organic layer is dried over MgSO₄ and evaporated under reduced pressure. The residue is purified by flash chromatography (Silica Gel, dichloromethane:methanol:acetic acid 90:9:1) and the material obtained is crystallised from dichloromethane to give compound 31-2.

Yield: 800 mg

ES mass spectrum: [M+H]⁺=381

Retention time HPLC: 5.45 min (HPLC Method 5)

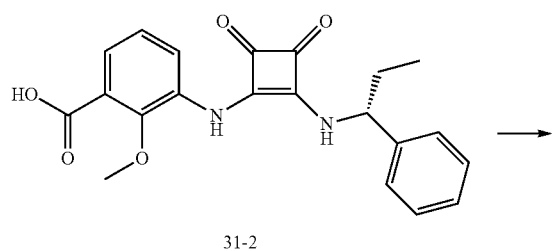

31-2

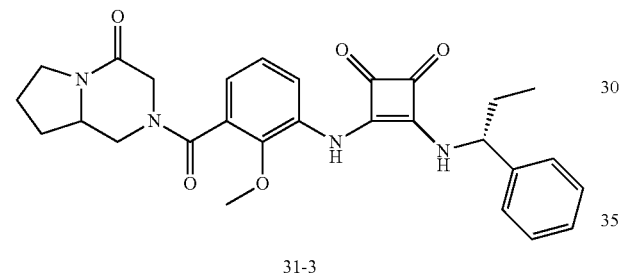

31-3

Compound 31-2 (30 mg, 0.079 mmol) is dissolved in acetonitrile (5 mL) and triethylamine (22 μL, 0.34 mmol), HATU (43 mg, 0.11 mmol) and hexahydro-pyrrolo[1,2-a]pyrazi-4-one (20 mg, 0.14 mmol) are added. The reaction mixture is stirred at room temperature overnight. Volatiles are removed under reduced pressure and the residue dissolved in dichloromethane and washed twice with 0.2 M HCl in water. The organic layer is dried over MgSO₄ and evaporated under reduced pressure and the material obtained is purified by flash chromatography (Silica Gel, gradient: dichloromethane/methanol from 100:0 to 90:10) to give compound 31-3.

Yield: 24 mg

ES mass spectrum: [M+H]+=503

Retention time HPLC: 0.93 min (HPLC method 2).

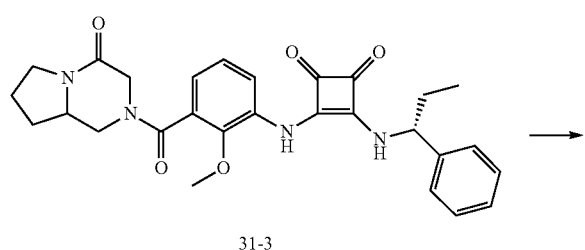

31-3

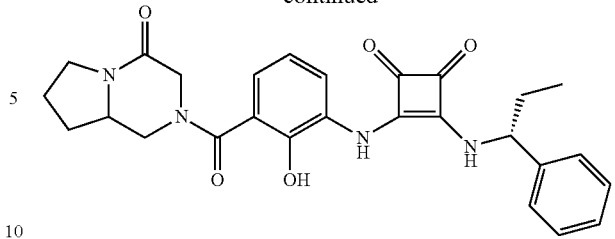

Example 31

Compound 31-3 (22 mg, 0.044 mmol) in dry dichloromethane (2 mL) is cooled to 0° C. and borontribromide (1 M in dichloromethane, 111.43 μL, 0.11 mmol) is added dropwise. The reaction mixture is stirred at room temperature. After 1 h, 0.2 M HCl in water (2 mL) and dichloromethane (2 mL) were added, the organic layer was separated, dried over MgSO₄ and concentrated under reduced pressure to give Example 31.

Yield: 20 mg

ES mass spectrum: [M+H]⁺=489

Retention time HPLC: 7.07 min (HPLC Method 5)

¹H NMR (Varian 400 MHz. DMSO-d6; 28° C.) 9.89 (1H, s); 9.28 (1H, s); 8.66 (1H, d); 7.80 (1H, d); 7.42-7.33 (4H, m); 7.31 (1H, m); 6.91 (1H, t); 6.87 (1H, dd); 5.10 (1H, m); 4.80-4.20 (2H, br); 3.73 (2H, m); 3.51 (1H, m); 3.41 (1H, m); 3.04 (1H, m); 2.01-1.85 (4H, m); 1.73 (1H, m); 1.55 (1H, m); 0.91 (3H, t).

Synthesis of Example 32

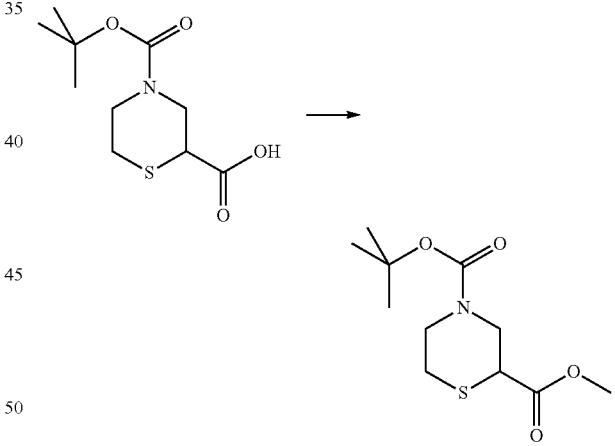

32-1

Thiomorpholine-2,4-dicarboxylic acid 4-tert-butyl ester (10 g, 40.43 mmol) is dissolved in a mixture of dichloromethane (50 mL) and methanol (40 mL) and cooled to 0° C. under N₂. A solution of trimethylsilyldiazomethane (2M in diethyl ether, 44.5 mL, 89 mmol) is added dropwise with stirring, the mixture allowed to warm to room temperature and stirred overnight. The solvent is removed under vacuum, the residue dissolved in ethyl acetate and washed with water, dried over magnesium sulphate and the solvent removed under vacuum to give compound 32-1.

Yield: 10.5 g

ES mass spectrum: [M+H-tBu]⁺=206

Retention time HPLC: 1.76 min (HPLC Method 1)

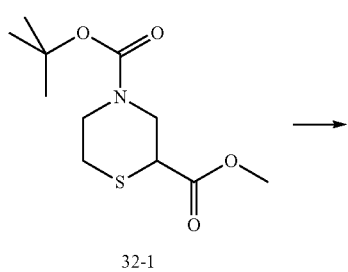

32-1

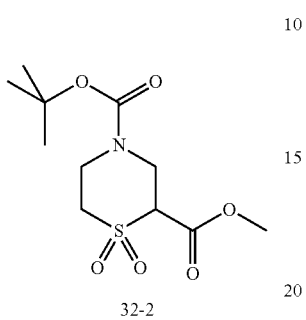

32-2

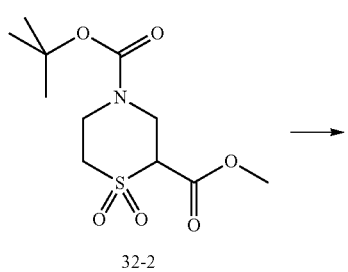

32-2

Compound 32-1 (10.5 g, 40.2 mmol) is dissolved in dichloromethane (150 mL) and cooled to 5° C. 3-chloroperoxybenzoic acid (13.9 g, 80.4 mmol) is added portionwise with cooling. The mixture is stirred overnight at room temperature. The mixture is filtered and the solution obtained is washed with saturated $NaHCO_3$ solution and water, dried over magnesium sulphate and the solvent removed. The residue is recrystallised from isopropanol to give to give compound 32-2.

Yield: 11.8 g

ES mass spectrum: $[M+H-tBu]^+=238$

Retention time HPLC: 1.14 min (HPLC Method 1)

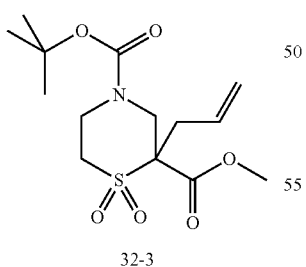

32-3

Compound 32-2 (9.9 g, 33.8 mmol) is dissolved in DMF (100 mL) and caesium carbonate (13.2 g, 40.5 mmol) is added. The mixture is stirred for 30 minutes then allyl bromide (8.76 mL, 101.3 mmol) in DMF (10 mL) is added dropwise. The mixture is stirred overnight at 45° C. The mixture is poured into 1 L of water and extracted several times with diethyl ether. The combined organic extracts are washed with water and brine, dried over magnesium sulphate and the solvent removed under vacuum. The residue is triturated with hexane to give compound 32-3.

Yield: 10.13 g

ES mass spectrum: $[M+H]^+=334$

Retention time HPLC: 1.25 min (HPLC Method 2)

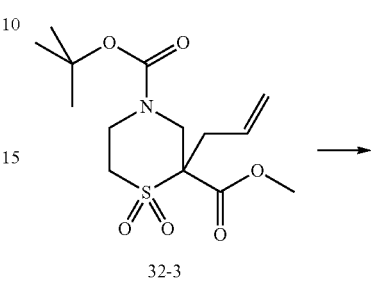

32-3

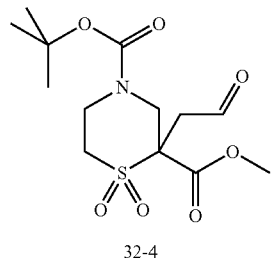

32-4

Compound 32-3 (7 g, 21 mmol) is dissolved in a mixture of dioxane (180 mL) and water (60 mL) and 2,6-lutidine (4.9 mL, 42 mmol), osmium tetroxide (2.5% in tert-butanol, 2.6 mL, 0.21 mmol) and sodium metaperiodate (18 g, 84 mmol) are added. The mixture is stirred at room temperature overnight then diluted with acetone (200 mL) filtered and the solvent removed. The residue is partitioned between DCM and water and extracted several times with DCM. The combined organic extracts are washed with water, dried over magnesium sulphate and the solvent removed under vacuum. The residue is recrystallised with 55 mL of isopropanol to give compound 32-4.

Yield: 3.93 g

ES mass spectrum: $[M+H]^+=336$

Retention time HPLC: 1.35 min (HPLC Method 2)

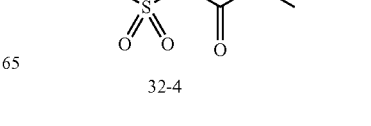

32-4

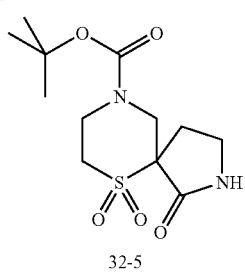

32-5

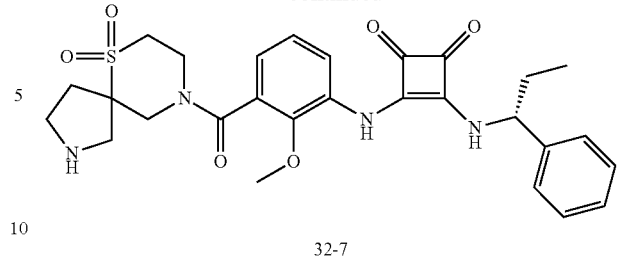

32-7

Compound 31-2 (40 mg, 0.11 mmol) is reacted with compound 32-6 (28 mg, 0.12 mmol) in a manner analogous to that used for the synthesis of compound 31-3 to give compound 32-7.

Yield: 59 mg
ES mass spectrum: [M+H]+=567
Retention time HPLC: 0.93 min (HPLC method 2).

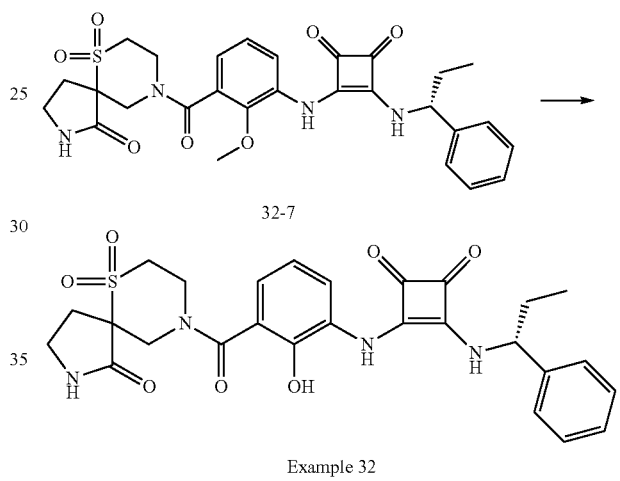

32-7

Example 32

Compound 32-4 (500 mg, 1.49 mmol) is dissolved in a mixture of methanol (15 mL) acetic acid (15 mL) and THF (10 mL), ammonium acetate (5.75 g, 75 mmol) and sodium cyanoborohydride (140 mg, 2.24 mmol) are added and the mixture stirred overnight. The mixture is then heated at reflux for 7 hours, concentrated under vacuum and diluted with water (50 mL). The mixture is basified with 10% NaOH solution and extracted several times with DCM. The combined organic extracts are dried over magnesium sulphate and the solvent removed under vacuum. The residue is purified by flash chromatography (Silica Gel, gradient: cyclohexane/ ethyl acetate from 8:2 to 0:1) give compound 32-5.

Yield: 126 mg
ES mass spectrum: [M+H]+=305
Retention time HPLC: 6.16 min (HPLC Method 3)

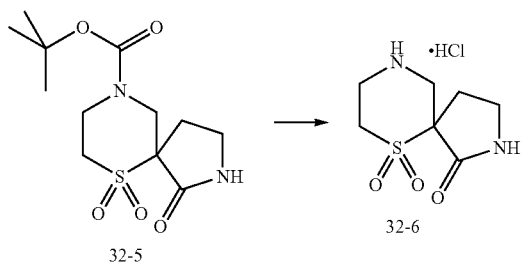 [SMILES: CC(C)(C)OC(=O)N1CCS(=O)(=O)C2(CCNC2=O)C1 ; O=C1NCCC12CNCCS2(=O)=O ; Cl]

32-5    32-6

Compound 32-5 (126 mg, 0-41 mmol) is dissolved dioxane (3 mL) and hydrogen chloride (4 M in dioxane, 4 mL, 16 mmol) is added. The mixture is stirred overnight then the solvent removed under vacuum. The residue is triturated with diethyl ether and hot isopropanol to give compound 32-6.

Yield: 96 mg
ES mass spectrum: [M+H]+=205
Retention time HPLC: 0.28 min (HPLC Method 1)

Compound 32-7 (59 mg, 0.10 mmol) is treated in a manner analogous to that used for the synthesis of example 31 to give Example 32.

Yield: 37 mg
ES mass spectrum: [M+H]+=553
Retention time HPLC: 7.27 min (HPLC Method 3)
$^1$H NMR (Varian 400 MHz. DMSO-d6; 28° C.) 9.57 (1H, br); 9.28 (1H, br); 8.67 (1H, d); 8.60 (1H, br); 7.81 (1H, d); 7.42-7.35 (4H, m) 7.30 (1H, m); 6.89 (2H, s, br); 5.10 (1H,m); 4.94 (1H, br); 3.88 (2H, br); 3.58 (4H, m); 2.67 (1H,m); 2.12 (1H, br); 1.91 (2H, m); 0.91 (3H, t).

Synthesis of Example 33

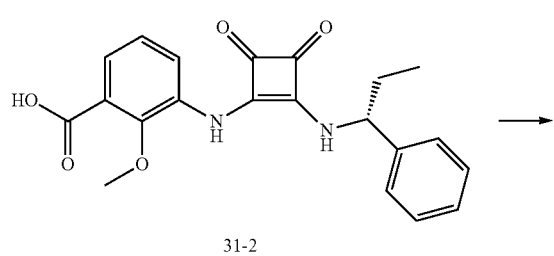

31-2

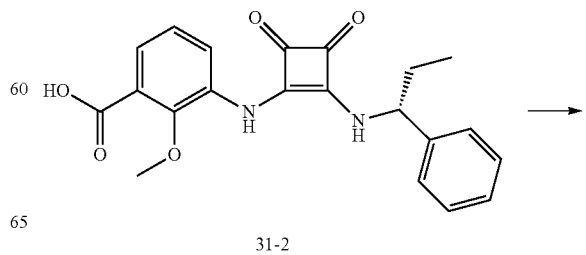

31-2

-continued

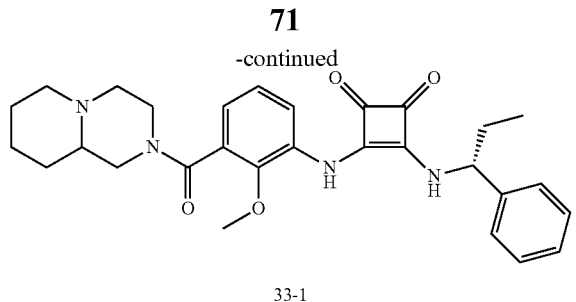

33-1

Compound 31-2 (40 mg, 0.11 mmol) is reacted with octahydro-pyrido[1,2-a]pyrazine (22 mg, 0.16 mmol) in a manner analogous to that used for the synthesis of compound 31-3 to give compound 33-1.

Yield: 53 mg
ES mass spectrum: [M+H]+=503
Retention time HPLC: 0.99 min (HPLC method 2).

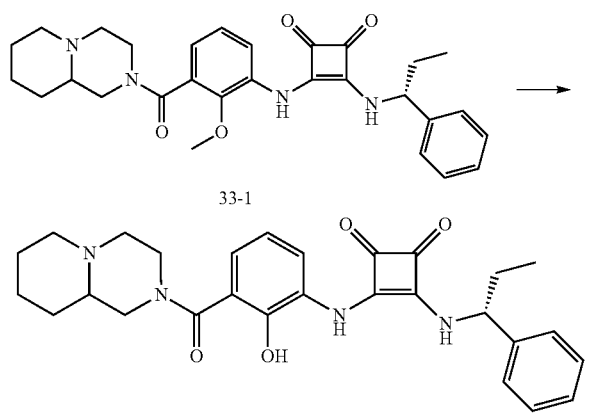

33-1

Example 33

Compound 33-1 (53 mg, 0.11 mmol) is treated in a manner analogous to that used for the synthesis of example 31 to give Example 33.

Yield: 24 mg
ES mass spectrum: [M+H]+=489
Retention time HPLC: 8.07 min (HPLC Method 5)
$^1$H NMR (Varian 400 MHz. DMSO-d6; 28° C.) 9.31 (2H, br); 8.71 (1H, d); 7.74 (1H, d); 7.30-7.40 (5H, m); 6.84 (2H, m); 5.11 (1H, m); 3.93 (1H, br); 3.00 (1H, m br); 2.69 (3H, m); 2.05 (1H, m); 1.92 (3H, m); 1.81 (1H, m); 1.68 (1H, m); 1.56 (1H, m), 1.46 (2H, m); 1.16 (2H, m); 0.91 (3H, t).

Synthesis of Example 34

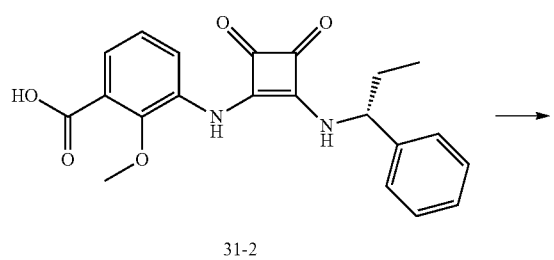

31-2

-continued

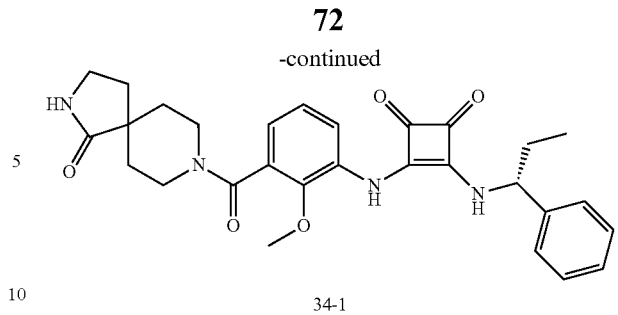

34-1

Compound 31-2 (30 mg, 0.08 mmol) is reacted with 2,8-diaza-spiro[4.5]decan-1-one hydrochloride (16 mg, 0.09 mmol) in a manner analogous to that used for the synthesis of compound 31-3 to give compound 34-1.

Yield: 41 mg
ES mass spectrum: [M+H]+=517
Retention time HPLC: 0.91 min (HPLC method 2).

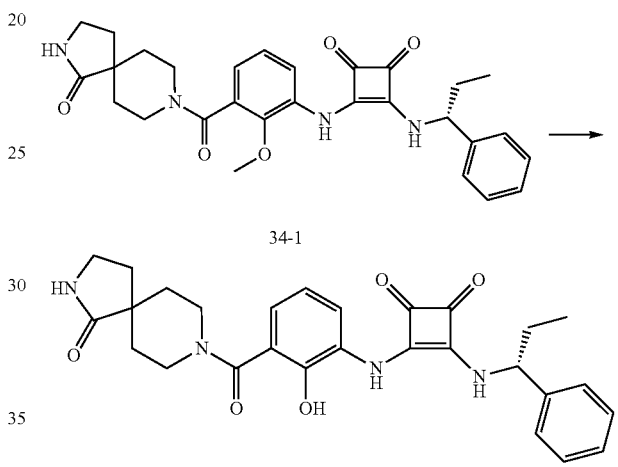

34-1

Example 34

Compound 34-1 (41 mg, 0.08 mmol) is treated in a manner analogous to that used for the synthesis of example 31 to give Example 34.

Yield: 33 mg
ES mass spectrum: [M+H]+=503
Retention time HPLC: 8.07 min (HPLC Method 5)
$^1$H NMR (Varian 400 MHz. DMSO-d6; 28° C.) 9.44 (2H, br); 8.66 (1H, d); 7.74 (1H, d); 7.57 (1H, s); 7.30-7.40 (5H, m); 6.84 (2H, m); 5.09 (1H, m); 3.91 (2H, br); 3.12-3.17 (4H, m); 1.90-1.98 (4H, m); 1.65 (2H, m); 1.39 (2H, m); 0.91 (3H, t).

Synthesis of Example 35

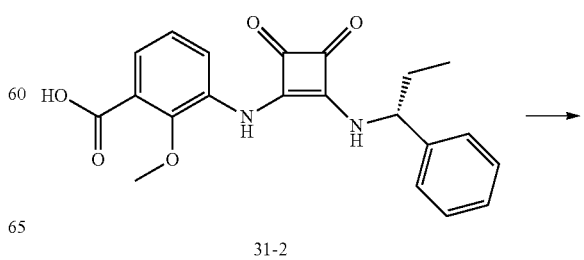

31-2

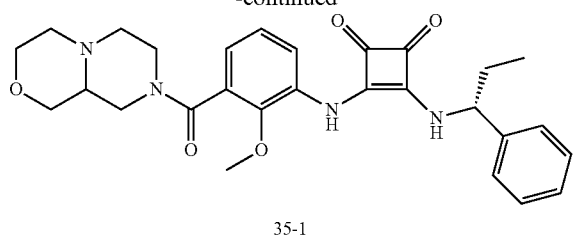

35-1

Compound 31-2 (50 mg, 0.13 mmol) is allowed to react with compound 17-6 (20 mg, 0.14 mmol) in a manner analogous to that used for the synthesis of compound 31-3 to give compound 35-1.

Yield: 40 mg

ES mass spectrum: [M+H]+=505

Retention time HPLC: 0.91 min (HPLC method 1).

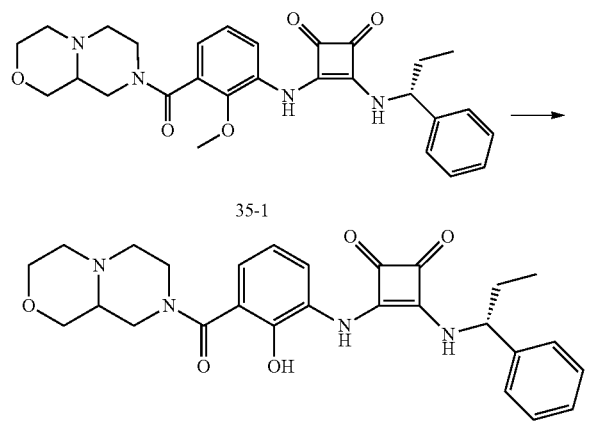

Example 35

Compound 35-1 (41 mg, 0.08 mmol) is treated in a manner analogous to that used for the synthesis of example 31 to give Example 35.

Yield: 7 mg

ES mass spectrum: [M+H]+=491

Retention time HPLC: 7.22 min (HPLC Method 5)

$^1$H NMR (Varian 400 MHz. DMSO-d6; 28° C.) 9.83 (1H, br); 9.29 (1H, br); 8.73 (1H, d); 7.77 (1H, d); 7.45-7.38 (4H, m) 7.36 (1H, m); 6.92 (2H, m); 5.17 (1H,m); 3.79 (1H, d); 3.59 (1H, m); 3.56 (1H, m); 3.13 (2H, m); 2.78-2.67 (2H, m); 2.27-2.15 (3H, m); 1.81 (2H, m); 1.34 (3H, m); 0.97 (3H, t)

Synthesis of Example 36

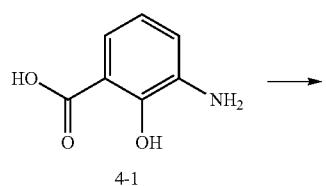

4-1

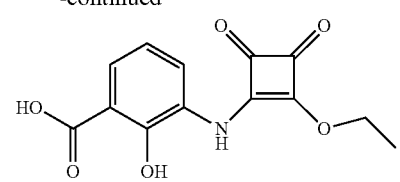

36-1

Compound 4-1 (480 mg, 3.13 mmol), 3,4-diethoxy-3-cyclobutene-1,2-dione (557 μL, 3.76 mmol) and triethylamine (1 mL) are dissolved in ethanol (5 mL) and the mixture refluxed for 1 hour. The solvent is removed, and the residue partitioned between 1 M aqueous NaOH solution and ethyl acetate. The aqueous phase is washed three times with ethyl acetate, acidified to pH 2 with concentrated HCl solution and extracted three times with DCM. The combined DCM extracts were dried and the solvent removed under reduced pressure to give compound 36-1.

Yield: 570 mg

ES mass spectrum: [M+H]+=270

Retention time HPLC: 0.65 min (HPLC method 2)

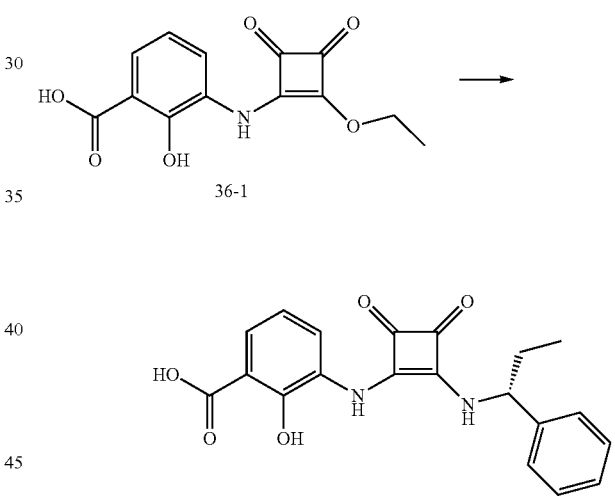

36-1

36-2

Compound 36-1 (300 mg, 1.08 mmol), (R)-1-phenylpropylamine (187 μL, 1.3 mmol) and triethylamine (377 μL, 2.71 mmol) are suspended in ethanol (5 mL) and heated at reflux for 30 minutes. The solvent is removed, and the residue partitioned between 1 M aqueous NaOH solution and ethyl acetate. The aqueous phase is washed three times with ethyl acetate, acidified to pH 2 with concentrated HCl solution and extracted three times with ethyl acetate. The combined organic extracts are dried and the solvent removed under reduced pressure to give compound 36-2.

Yield: 370 mg

ES mass spectrum: [M+H]+=367

Retention time HPLC: 0.81 min (HPLC method 2)

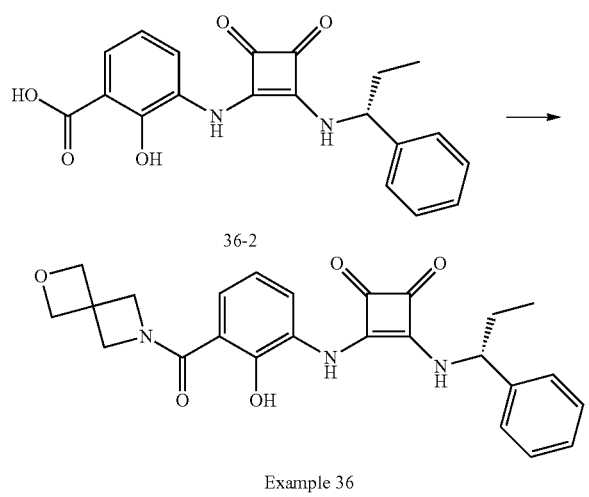

36-2

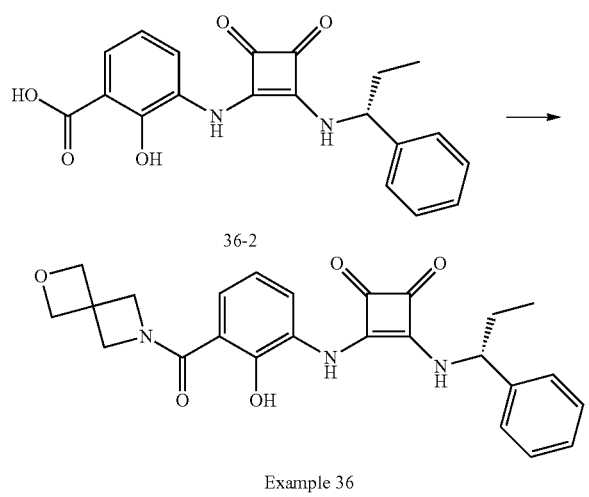

Example 36

Compound 36-2 (30 mg, 0.08 mmol), 2-oxa-6-aza-spiro[3.3]heptane hemi-oxalate (24 mg, 0.08 mmol, Angewandte Chemie, International Edition, 2008, vol. 47, p. 4512-4515.), HATU (74 mg, 0.2 mmol) and triethylamine (46 µL, 0.33 mmol) are suspended in DMF (1.5 mL) and stirred overnight. The solvent is removed under reduced pressure and the residue purified by semi-preparative reverse phase HPLC to give Example 36.

Yield: 4 mg
ES mass spectrum: [M+H]+=448
Retention time HPLC: 10.66 min (HPLC Method 6)
$^1$H NMR (Varian Inova 500 MHz. CD$_3$COCD$_3$; 27° C.) 13.4 (1H, br); 8.39 (1H, br); 8.15 (1H, d); 7.99 (1H, d); 7.46 (2H, m); 7.40 (2H, m); 7.31 (1H, m); 7.21 (1H, m); 6.85 (1H, t), 5.20 (1H, m); 4.97 (2H, br); 4.79 (4H, s); 4.45 (2H, br); 2.03 (2H, m); 0.97 (3H, t).

Synthesis of Example 37

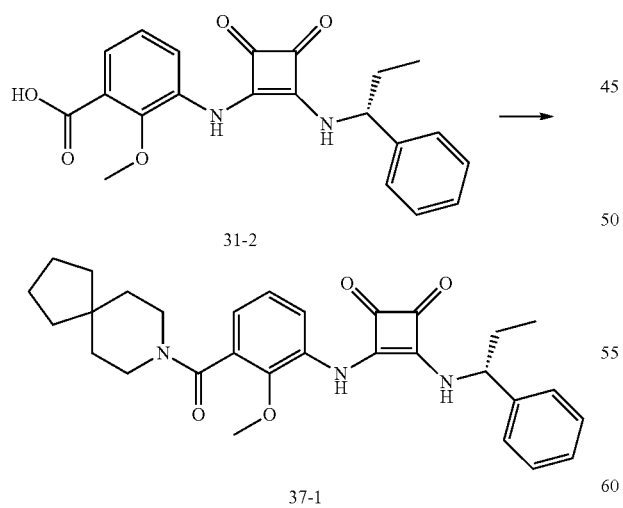

31-2

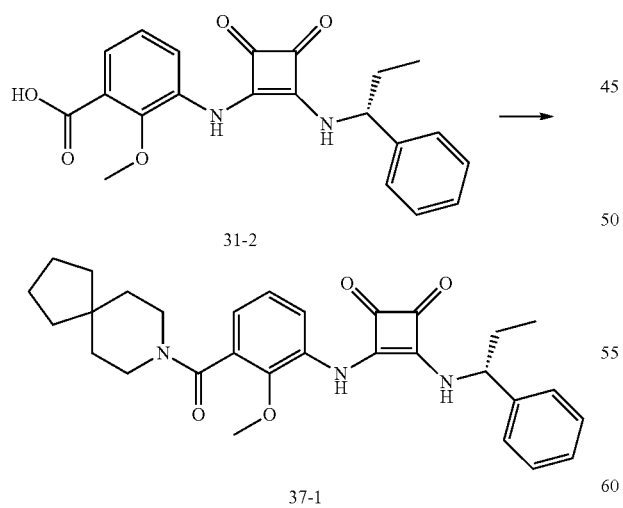

37-1

Compound 31-2 (80 mg, 0.21 mmol) is allowed to react with 8-aza-spiro[4.5]decane hydrochloride (56 mg, 0.32 mmol, J. Am. Chem. Soc., 2009, vol. 131, p. 8066-8076) in a manner analogous to that used for the synthesis of compound 31-3 to give compound 37-1.

Yield: 90 mg
ES mass spectrum: [M+H]+=502
Retention time HPLC: 3.11 min (HPLC method 4).

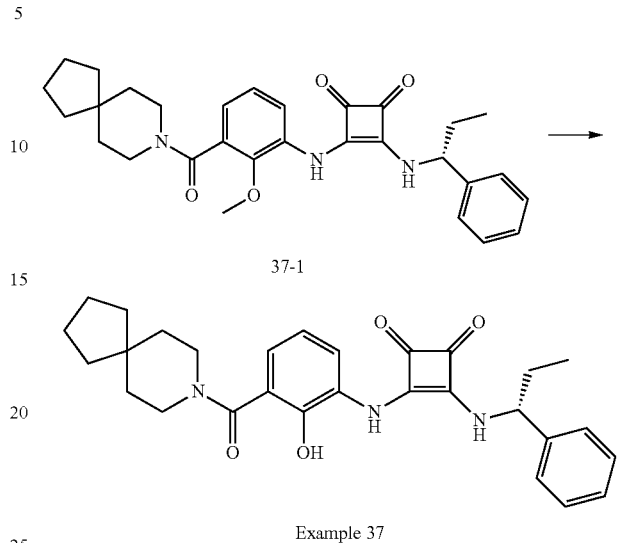

37-1

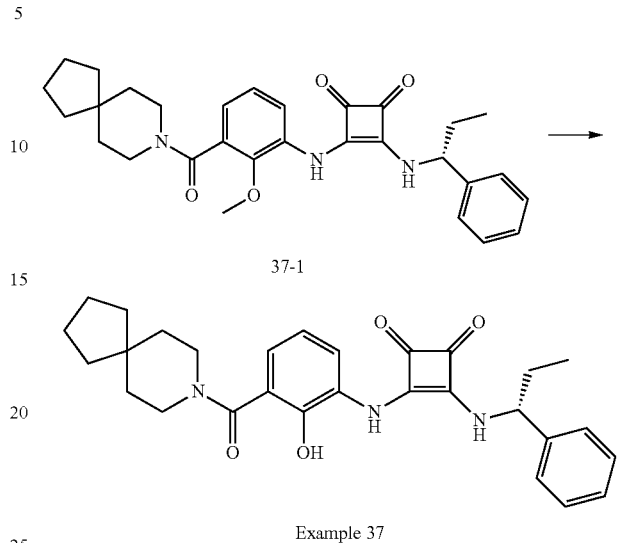

Example 37

Compound 37-1 (90 mg, 0.17 mmol) is treated in a manner analogous to that used for the synthesis of example 31 to give Example 37.

Yield: 31 mg
ES mass spectrum: [M+H]+=488
Retention time HPLC: 3.11 min (HPLC Method 5). $^1$H NMR (Varian 400 MHz. DMSO-d6; 28° C.) 9.75 (1H, br); 9.25 (1H, br); 8.67 (1H, d); 7.71 (1H, d); 7.42-7.35 (4H, m) 7.30 (1H, m); 6.87 (1H, t); 6.81 (1H, dd); 5.10 (1H, m); 3.41 (4H, s, br); 1.91 (2H, m); 1.58 (4H, m); 1.43 (8H, m); 0.91 (3H, t).

Synthesis of Example 38

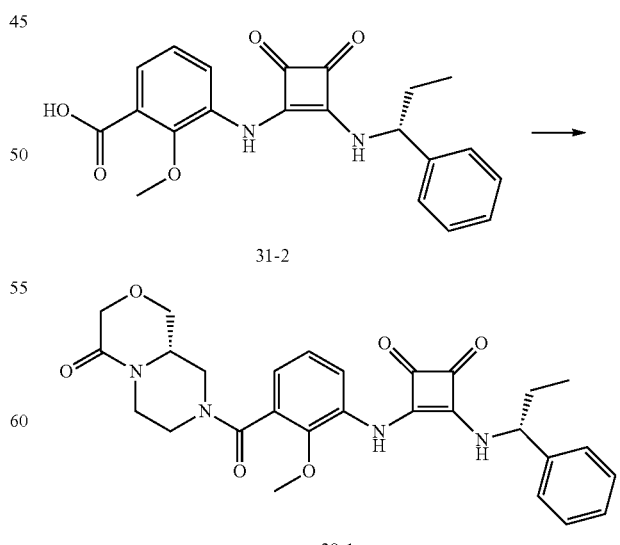

31-2

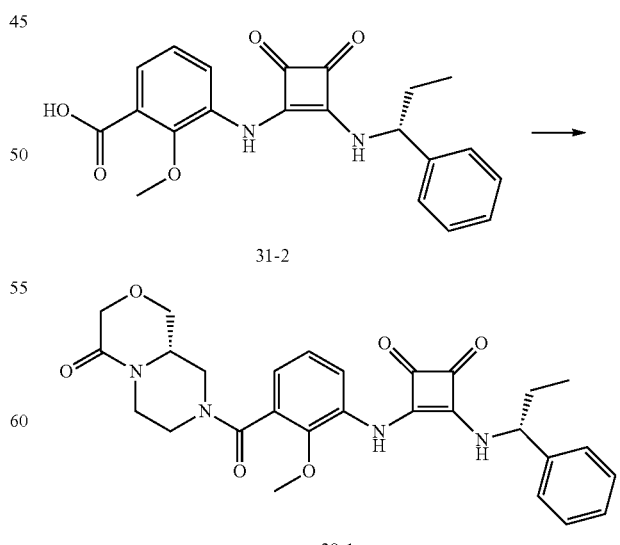

38-1

Compound 31-2 (50 mg, 0.13 mmol) is allowed to react with compound 19-3 (28 mg, 0.14 mmol) in a manner analogous to that used for the synthesis of compound 31-3 to give compound 38-1.
Yield: 52 mg
ES mass spectrum: [M+H]+=519
Retention time HPLC: 0.93 min (HPLC method 1).

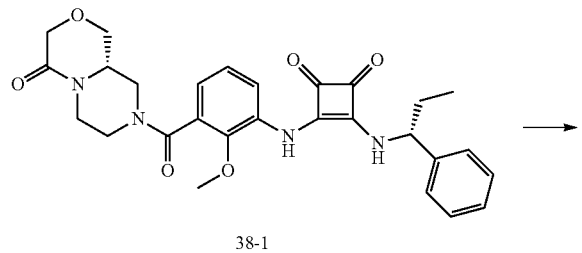

38-1

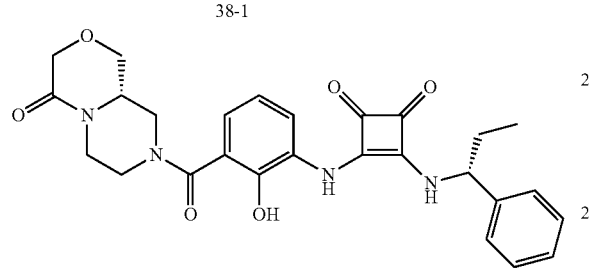

Example 38

Compound 38-1 (52 mg, 0.10 mmol) is treated in a manner analogous to that used for the synthesis of example 31 to give Example 38.
Yield: 10 mg
ES mass spectrum: [M+H]+=505
Retention time HPLC: 3.11 min (HPLC Method 5).
$^1$H NMR (Varian 400 MHz. DMSO-d6; 28° C.) 9.30 (1H, br); 8.67 (1H, d); 8.75 (1H, d); 7.78 (1H, d); 7.42-7.35 (4H, m) 7.30 (1H, m); 6.87 (2H, m); 5.12 (1H,m); 4.38 (1H, m); 4.05 (1H, s); 4.04 (1H, m); 3.57 (3H, m); 2.94 (1H, m); 2.66 (1H, m); 1.92 (2H, m); 0.97 (3H, t). 3 H not observed Synthesis of Example 39

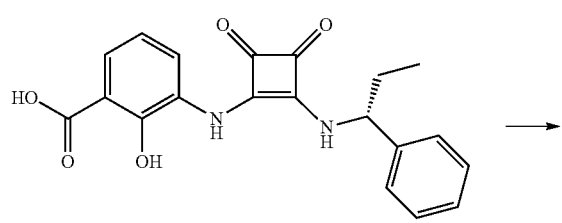

36-2

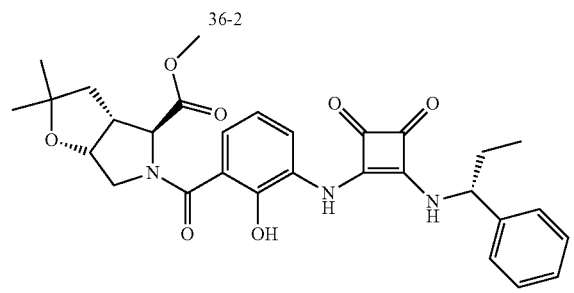

Example 39

Compound 36-2 (50 mg, 0.15 mmol) is allowed to react with (3aR,4S,6aR)-2,2-dimethyl-hexahydro-furo[2,3-c]pyrrole-4-carboxylic acid methyl ester (41 mg, 0.21 mmol, *Tetrahedron Letters*, 2004, vol. 45, 6097-6100.) in a manner analogous to that used for the synthesis of example 36 to give Example 39.
Yield: 8 mg
ES mass spectrum: [M+H]+=548
Retention time HPLC: 11.79 min (HPLC Method 6).
$^1$H NMR (Varian Inova 500 MHz. DMSO-d6; 27° C.) 10.40 (1H, br); 9.39 (1H, br); 8.70 (1H, br); 7.48 (1H, m); 7.40-7.25 (5H, m); 7.03-6.68 (2H, m, br); 5.10 (1H; m); 4.61 (1H, m); 4.55 (1H, m); 3.93-3.42 (4H, m); 3.74 (2H, s); 3.07 (2H, br); 2.18 (1H, m); 1.92 (1H, m); 1.82 (2H, m); 1.25 (3H, s, br); 1.15 (3H, s); 0.91 (3H, t)

Synthesis of Example 40

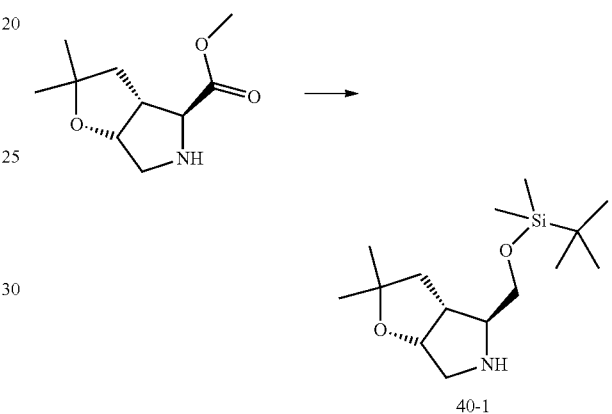

40-1

(3aR,4S,6aR)-2,2-Dimethyl-hexahydro-furo[2,3-c]pyrrole-4-carboxylic acid methyl ester (250 mg, 1.25 mmol, Tetrahedron Letters, 2004, vol. 45, 6097-6100.) is dissolved in dry THF (10 mL) and lithium borohydride (2 M solution in THF, 1.25 mL, 2.5 mmol) is added. The mixture is stirred for 3 hours then cooled to 0° C. and methanol (4 mL) is added. The mixture is acidified with a 1.25 molar solution of hydrogen chloride in methanol until acidic and then basified with triethylamine and the solvent removed. Dichloromethane is added and the suspension filtered. The solution is cooled to 0° C. and imidazole (89 mg, 1.31 mmol) and tert-butyldimethylchlorosilane (181 mg, 1.2 mmol) are added. The mixture is stirred overnight at room temperature then diluted with DCM and 10% aqueous NH$_4$Cl. The aqueous phase is extracted with DCM, the organic phases are combined and the solvent removed under vacuum to give compound 40-1.
Yield: 60 mg
ES mass spectrum: [M+H]$^+$=286
Retention time HPLC: 1.60 min (HPLC Method 4).

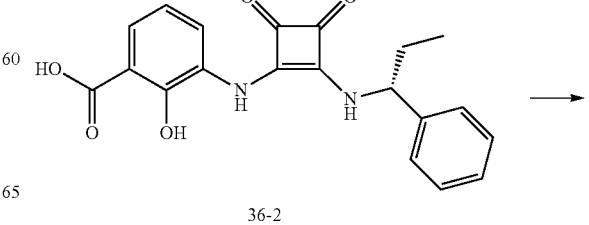

36-2

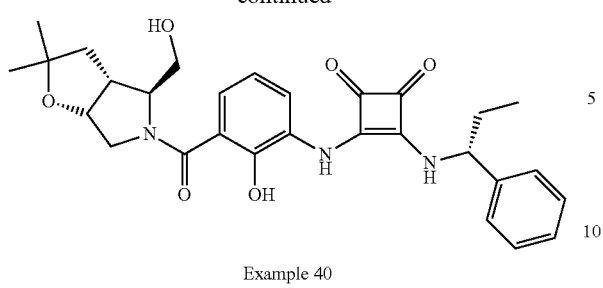

Example 40

Compound 36-2 (50 mg, 0.15 mmol) is allowed to react with compound 40-1 (60 mg, 0.21 mmol) in a manner analogous to that used for the synthesis of example 36 to give Example 40.

Yield: 7 mg

ES mass spectrum: [M+H]+=520

Retention time HPLC: 10.56 min (HPLC Method 6).

$^1$H NMR (Varian 400 MHz. DMSO-d6; 28° C.) 8.76 (1H, br); 7.78 (1H, br); 7.30-7.42 (5H, m); 6.99 (1H, br); 6.81 (2H, br); 5.35 (1H, br); 5.06 (1H, m); 4.51 (1H, d br); 4.29 (1H, br); 3.5-4.89 (2H, m); 2.90 (1H, m br); 2.09 (1H, m); 1.90 (2H, m); 1.54-1.7 (2H, m); 1.26 (1H, m); 1.18 (3H, s); 1.06 (3H, s); 0.94 (3H, t). 2H not observed Synthesis of Example 41

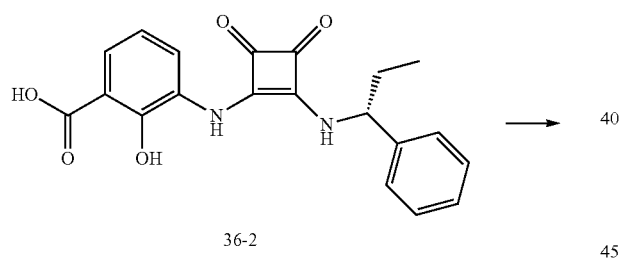

36-2

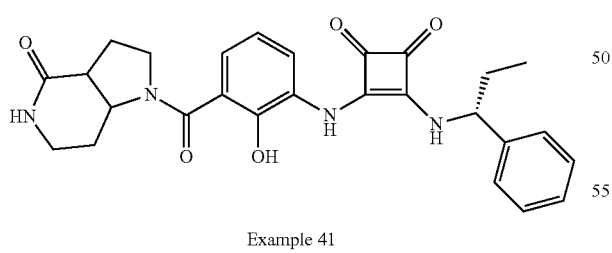

Example 41

Compound 36-2 (50 mg, 0.15 mmol) is allowed to react with octahydro-pyrrolo[3,2-c]pyridine-4-one hydrochloride (37 mg, 0.21 mmol) in a manner analogous to that used for the synthesis of example 36 to give Example 41.

Yield: 9 mg

ES mass spectrum: [M+H]+=489

Retention time HPLC: 7.18 min (HPLC Method 5).

$^1$H NMR (Varian 400 MHz. DMSO-d6; 28° C.) 7.97 (1H, br); 7.41 (4H, m); 7.29 (1H, m), 7.17 (1H, br); 6.92 (1H, m); 5.19 (1H, m); 4.60 (1H, m br); 3.68 (2H, m); 3.15 (2H, m); 3.05 (1H, m); 2.29 (3H, m); 2.11 (1H, m); 1.29 (2H, m); 0.98 (3H, t). 3H not observed Synthesis of Example 42

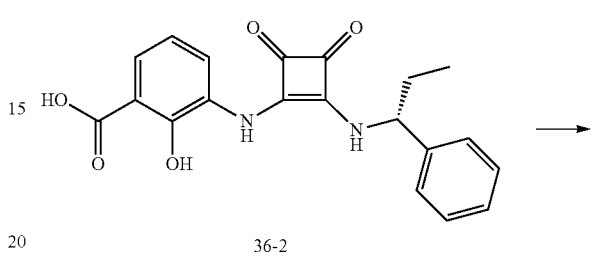

36-2

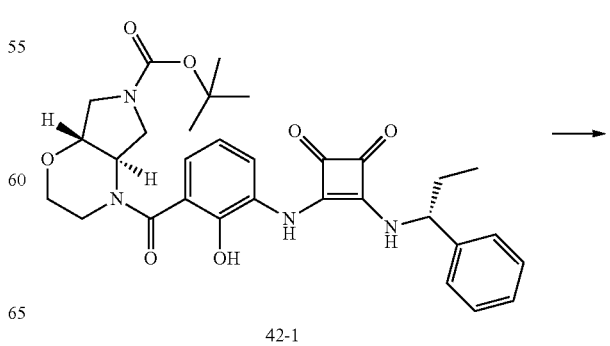

42-1

Compound 36-2 (130 mg, 0.33 mmol) is allowed to react with trans-hexahydro-pyrrolo[3,4-B][1.4]oxazine-6-carbolic acid tert-butyl ester (114 mg, 0.5 mmol) in a manner analogous to that used for the synthesis of compound 36-3 to give compound 42-1.

Yield: 145 mg

ES mass spectrum: [M+H]+=577

Retention time HPLC: 2.68 min (HPLC Method 4).

42-1

-continued

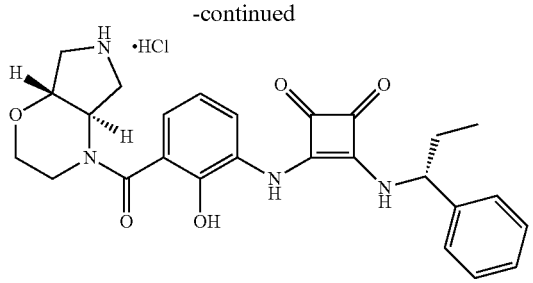

Example 42

To a solution of compound 42-1 (145 mg, 0.21 mmol) in 1,4-dioxane dry (2 mL) is added hydrochloric acid (0.63 mL, 2.54 mmol) and the mixture is stirred at room temperature overnight. The solvent is evaporated under vacuum and the residue taken up with petroleum ether and filtered. The material obtained is suspended in ethyl ether, filtered and the solid washed with ethyl ether:acetone 4:1 to give Example 42.

Yield: 93 mg
ES mass spectrum: [M+H]+=477
Retention time HPLC: 7.42 min (HPLC Method 5)
$^1$H NMR (Varian 400 MHz. DMSO-d6; 28° C.) 10.00 (1H, s); 9.50 (1H, s); 9.29 (2H, br); 8.85 (1H, d); 7.82 (1H, m); 7.43-7.28 (5H, m); 6.92 (2H, m); 5.10 (1H, m); 3.67-3.93 (4H, m); 3.50 (4H, m); 3.16 (2H, m); 2.97 (1H, m); 1.91 (1H, m); 0.91 (3H, t)

Synthesis of Example 43

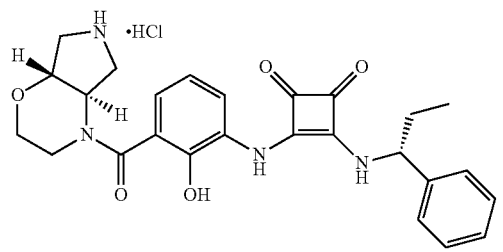

42-2

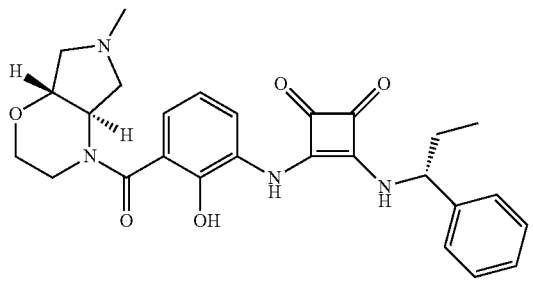

Example 43

To a solution of compound 42-2 (65 mg, 0.13 mmol) and triethylamine (26.49 μL, 0.19 mmol) in tetrahydrofuran dry (4 mL) is added formaldehyde (47.81 μL, 0.63 mmol) and the mixture is stirred at room temperature. After 30 min, sodium triacetoxyborohydride (93.99 mg, 0.44 mmol) is added and the mixture stirred at room temperature overnight. The solution is diluted with water (8 mL), the solvent evaporated under reduced pressure and the residue extracted with dichloromethane. The organic layer is separated, dried over Na2SO4 and evaporated under vacuum. The crude material is purified via semi-preparative reversed phase HPLC to give Example 43.

Yield: 14 mg
ES mass spectrum: [M+H]+=491
Retention time HPLC: 7.98 min (HPLC Method 5)
$^1$H NMR (Varian 400 MHz. DMSO-d6; 28° C.) 10.07 (1H, br); 9.37 (1H, br); 8.76 (1H, d); 7.81 (1H, d); 7.43-7.28 (5H, m); 6.89 (2H, m); 5.10 (1H, m); 3.93 (2H, m); 3.66 (2H, m); 3.45 (3H, m); 3.14 (3H, m); 2.86 (3H, s); 1.92 (2H, m); 0.91 (3H, t).

Synthesis of Example 44

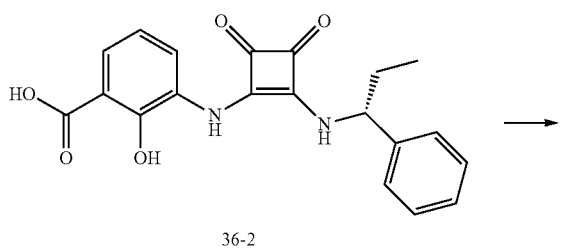

36-2

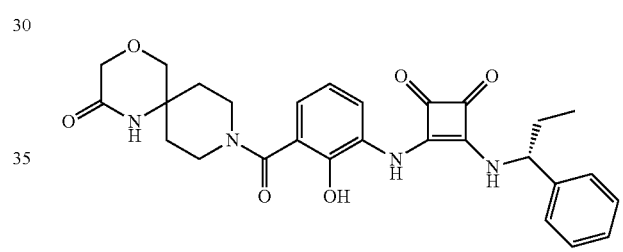

Example 44

Compound 36-2 (50 mg, 0.15 mmol) is reacted with 4-oxa-1,9-diaza-spiro[5.5]undecan-2-one hydrochloride (46 mg, 0.22 mmol) in a manner analogous to that used for the synthesis of example 36 to give Example 44.

Yield: 7 mg
ES mass spectrum: [M+H]+=519
Retention time HPLC: 9.14 min (HPLC Method 6)
$^1$H NMR (Varian 400 MHz. DMSO-d6; 28° C.) 8.69 (1H, d); 8.33 (1H, s); 7.76 (1H, d); 7.35 (5H, m); 6.84 (2H, m); 5.11 (1H, m); 3.97 (2H, s); 3.65 (2H, s), 3.56 (1H, m), 3.01 (2H, m); 1.90 (2H, m); 1.66 (5H, m); 0.89 (3H, t). 1 H not observed.

Synthesis of Example 45

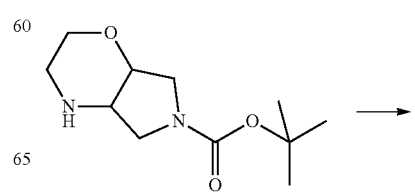

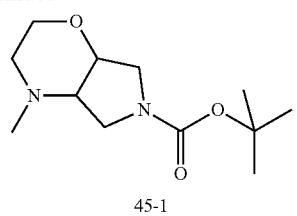

45-1

Trans-hexahydro-pyrrolo[3,4-B][1.4]oxazine-6-carbolic acid tert-butyl ester (120 mg, 0.53 mmol) is dissolved in THF (4 mL) and formaldehyde (36% in water, 198 μL, 2.63 mmol) is added. After 30 minutes sodium triacetoxyborohydride (390 mg, 1.84 mmol) is added and the mixture stirred overnight. Water (8 mL) is added and the mixture extracted with DCM. The combined extracts are dried and the solvent removed to give compound 45-1.

Yield: 135 mg

EI mass spectrum: [M+H]$^+$=242

Retention time GC-MS: 10.28 min (GC/MS Method 7)

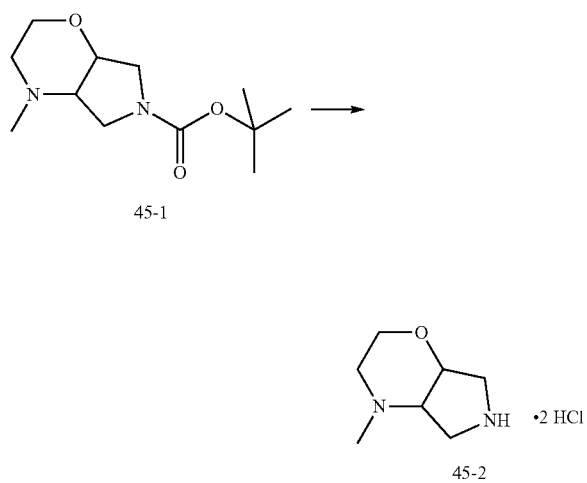

45-1

45-2

Compound 45-1 (135 mg, 0.48 mmol) is dissolved in 1,4-dioxane (2 mL) and hydrogen chloride (4 M in dioxane, 1.4 mL, 5.57 mmol) is added. The mixture is stirred for 3 hours then the solvent remover under vacuum to give compound 45-2.

Yield: 83 mg

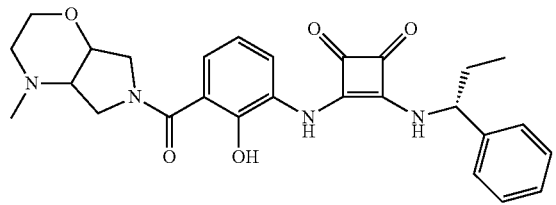

Example 45

Compound 36-2 (50 mg, 0.15 mmol) is reacted with compound 45-2 (48 mg, 0.22 mmol) in a manner analogous to that used for the synthesis of example 36 to give Example 45.

Yield: 31 mg

ES mass spectrum: [M+H]+=491

Retention time HPLC: 8.05 min (HPLC Method 5)

$^1$H NMR (Varian 400 MHz. DMSO-d6; 28° C.) 10.65 (1H, d br); 9.30 (1H, s); 8.65 (1H, t br); 7.83 (1H, d); 7.39 (4H, m); 7.31 (1H, m); 7.04 (1H, m); 6.92 (1H, m); 5.11 (1H, m); 3.74-4.12 (5H, m); 3.47 (4H, m); 2.91 (4H, m br); 1.92 (2H, m); 0.91 (3H, t).

Synthesis of Example 46

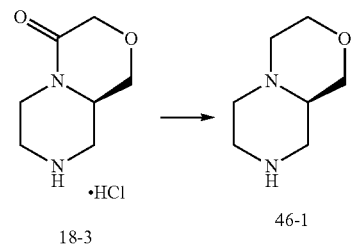 [SMILES: O=C1COC[C@H]2CNCCN12 ; C1CN2CCOC[C@H]2CN1 ; Cl]

18-3

46-1

Compound 18-3 (70 mg, 0.36 mmol) is dissolved in THF and borane-THF complex (1 M in THF, 3.6 mL, 3.6 mmol) added. The mixture is heated at 90° C. for 14 hours then cooled to 0° C. and hydrochloric acid (6 M, 10 mL) is added. The mixture is stirred at 60° C. for 4 hours and then concentrated under vacuum. The residue is loaded onto a SCX cartridge, washed with methanol and eluted with 1 M NH$_3$ in methanol. The solvent is removed to give compound 46-1

Yield: 40 mg

EI mass spectrum: [M+H]$^+$=142

Retention time HPLC: 6.74 min (GC/MS Method 7)

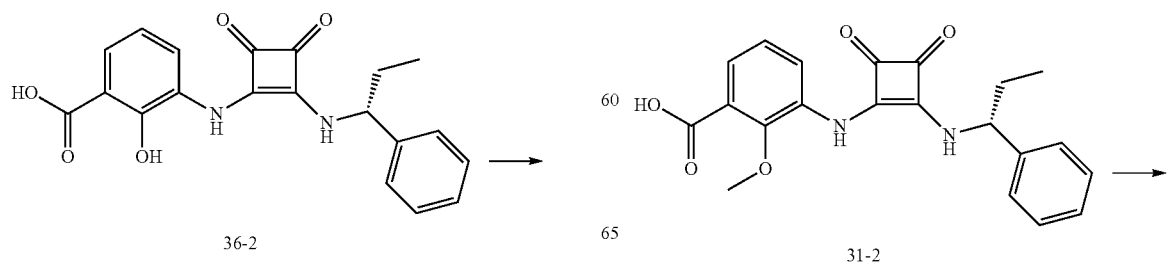

36-2

31-2

-continued

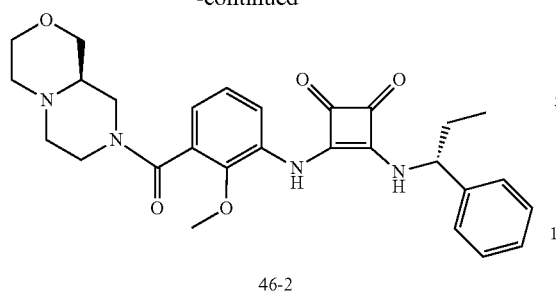

46-2

Compound 31-2 (96 mg, 0.25 mmol) is reacted with compound 46-1 (40 mg, 0.28 mmol) in a manner analogous to that used for the synthesis of compound 31-3 to give compound 46-2.

Yield: 40 mg

ES mass spectrum: [M+H]+=505

Retention time HPLC: 0.92 min (HPLC method 2)

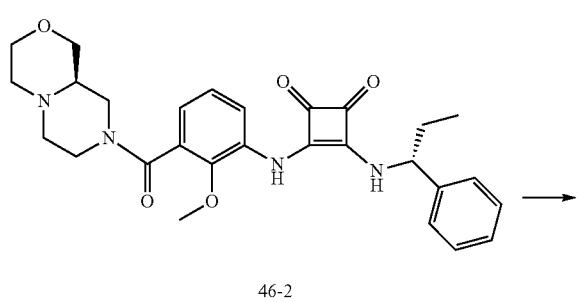

46-2

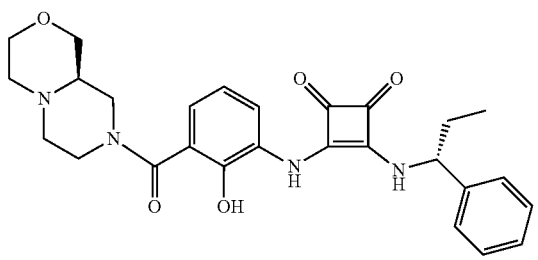

Example 46

Compound 46-2 (40 mg, 0.08 mmol) is treated in a manner analogous to that used for the synthesis of example 31 to give Example 46.

Yield: 20 mg

ES mass spectrum: [M+H]+=491

Retention time HPLC: 6.86 min (HPLC Method 6)

$^1$H NMR (Varian Inova 500 MHz. DMSO-d6; 27° C.) 9.81 (1H, s); 9.25 (1H, s); 8.65 (1H, d); 7.78 (1H, d); 7.29-7.39 (4H, m); 6.85 (2H, m); 5.11 (1H, m); 3.66 (4H, m); 3.02 (3H, m br); 2.72 (1H, m br); 2.15 (3H, m br); 1.91 (2H, m); 0.91 (3H, t). 2 H not observed.

Synthesis of Example 47

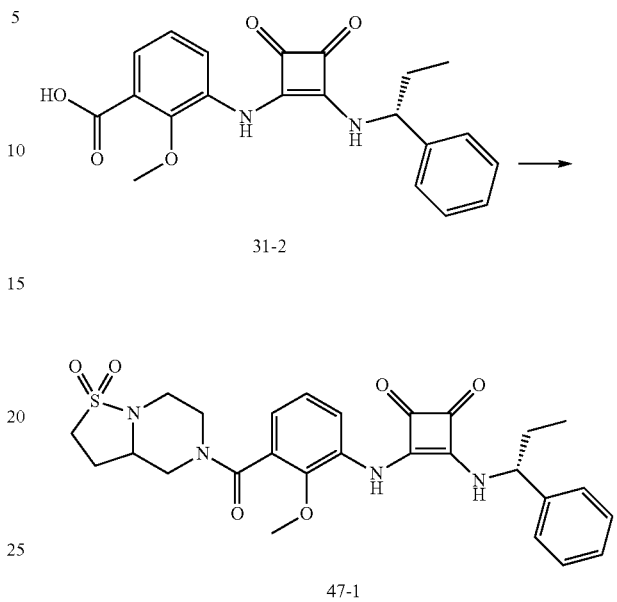

31-2

47-1

Compound 31-2 (100 mg, 0.26 mmol) is reacted with hexahydro-1-thia-5,7a-diaza-indene-1,1-dioxide hydrochloride (67 mg, 0.32 mmol, WO2007/28654) in a manner analogous to that used for the synthesis of compound 31-3 to give compound 47-1.

Yield: 100 mg

ES mass spectrum: [M+H]+=539

Retention time HPLC: 0.94 min (HPLC method 2)

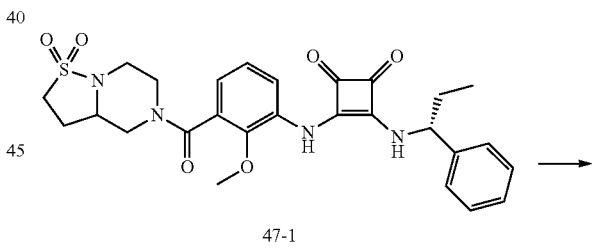

47-1

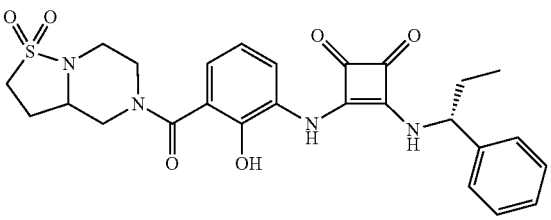

Example 47

Compound 47-1 (100 mg, 0.19 mmol) is treated in a manner analogous to that used for the synthesis of example 31 to give Example 47.

Yield: 3 mg

ES mass spectrum: [M+H]+=525

Retention time HPLC: 9.99 min (HPLC Method 6)

$^1$H NMR (Varian 400 MHz. DMSO-d6; 28° C.) 9.56 (2H, br); 8.65 (1H,br); 7.78 (1H,d); 7.30 (5H,m); 6.82 (2H,d); 5.08 (1H,m); 4.23 (4H,br); 2.95 (6H,m br); 2.70 (3H,m); 1.90 (2H,m); 0.88 (3H,t).

Synthesis of Example 48

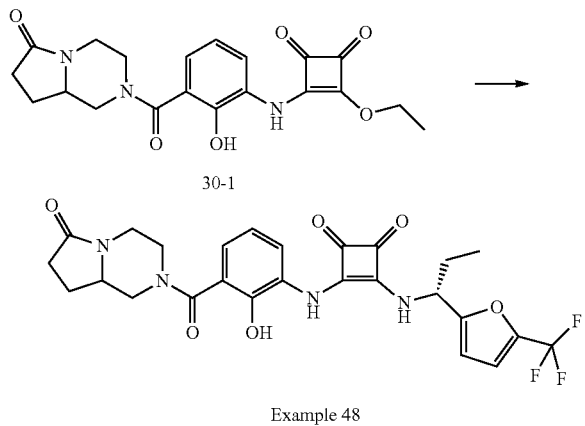

Example 48

Compound 30-1 (45 mg, 0.11 mmol) is reacted with compound 28-3 (75 mg, 0.15 mmol) in a manner analogous to that used for the synthesis of example 20 to give Example 48

Yield: 36 mg
ES mass spectrum: [M+H]$^+$=547
Retention time HPLC: 10.01 min (HPLC Method 6)
$^1$H NMR (Varian Inova 500 MHz. DMSO-d6; 27° C.) 9.57 (2H, br); 8.73 (1H, br); 7.81 (1H, d); 7.21 (1H, d); 6.85 (2H, br); 6.64 (1H, d); 5.28 (1H, m); 4.14-4.90 (2H, br); 3.83 (1H, m), 3.57 (2H, m); 2.80 (2H, m); 2.24 (2H, m); 1.97 (3H, m); 1.55 (1H, m); 0.95 (3H, t).

Synthesis of Example 49

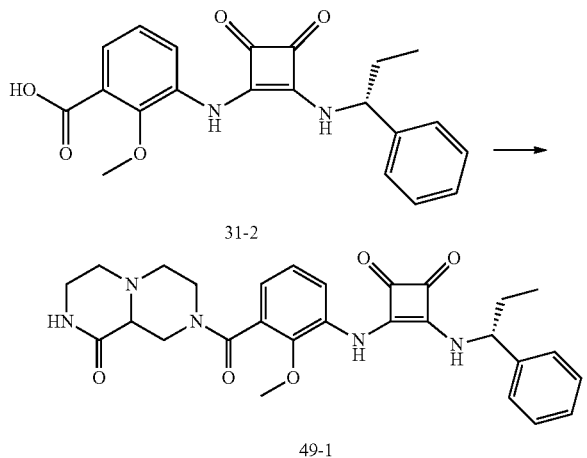

Compound 31-2 (100 mg, 0.26 mmol) is reacted with hexahydro-pyrazino[1,2-a]pyrazin-1-one hydrochloride (60 mg, 0.32 mmol, WO2007/28654) in a manner analogous to that used for the synthesis of compound 31-3 to give compound 49-1.

Yield: 130 mg
ES mass spectrum: [M+H]+=518
Retention time HPLC: 0.85 min (HPLC method 2)

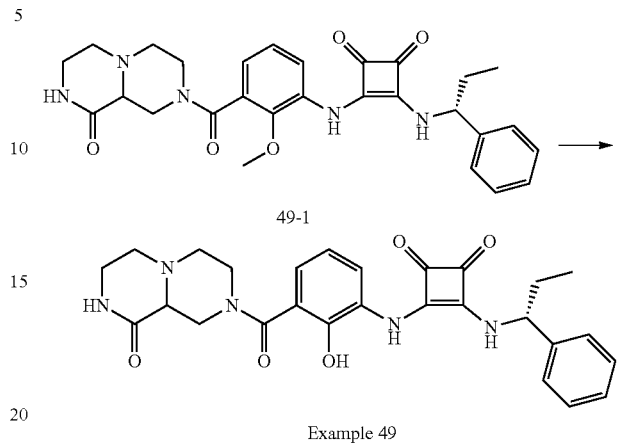

Example 49

Compound 49-1 (100 mg, 0.19 mmol) is treated in a manner analogous to that used for the synthesis of example 31 to give Example 49.

Yield: 11 mg
ES mass spectrum: [M+H]+=504
Retention time HPLC: 8.56 min (HPLC Method 6)
$^1$H NMR (Varian 400 MHz. DMSO-d6; 28° C.) 9.78 (1H, br); 9.24 (1H, br); 8.69 (1H, br); 7.79 (2H, d); 7.31-7.39 (5H, m); 6.83 (2H, m br); 5.1 (1H, m); 4.37-3.64 (2H, br); 3.07 (2H, m); 2.86 (4H, m); 2.32 (2H, m); 2.18 (1H, m); 1.85 (2H, m); 0.87 (3H, t).

Synthesis of Example 50

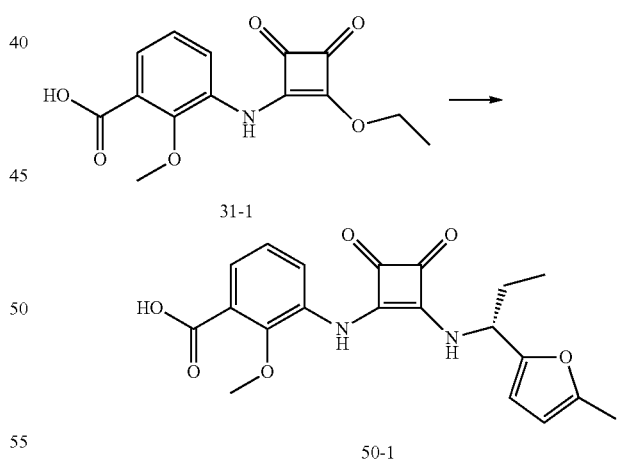

Compound 31-1 (390 mg, 1.34 mmol), (R)-1-(5-methyl-furan-2-yl)propylamine (186 mg, 1.34 mmol, Journal of Medicinal Chemistry, 2006, vol. 49, p. 7603-7606) and triethylamine (224 μL, 1.61 mmol) are dissolved in ethanol (3 mL) and heated at reflux for 30 minutes. The solvent is removed under vacuum, the residue redissolved in DCM and passed through an SCX cartridge eluting with 1:1 DCM:methanol. The solvent is removed and the residue suspended in 1 M aqueous NaOH solution, washed with ethyl acetate, acidified to approx pH 2 with concentrated hydrochloric acid and extracted three times with ethyl acetate. The combined organic extracts were dried and the solvent removed to give compound 50-1.
Yield: 210 mg
ES mass spectrum: [M+H]+=385
Retention time HPLC: 0.76 min (HPLC method 2)

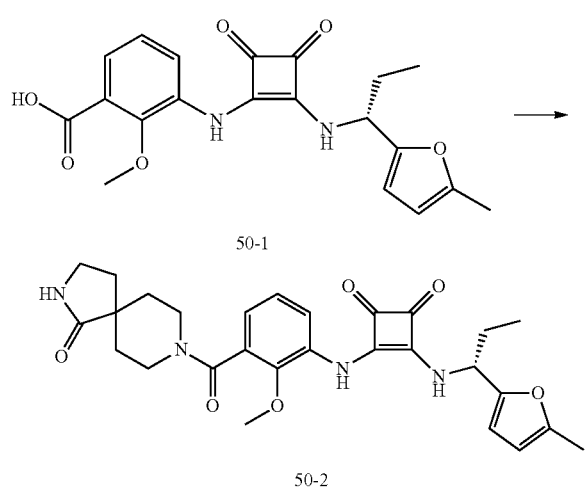 [SMILES: CC[C@@H](Nc1c(Nc2cccc(C(=O)O)c2OC)c(=O)c1=O)c1ccc(C)o1 ; CC[C@@H](Nc1c(Nc2cccc(C(=O)N3CCC4(CCNC4=O)CC3)c2OC)c(=O)c1=O)c1ccc(C)o1]

50-1

50-2

Compound 50-1 (55 mg, 0.14 mmol) is reacted with 2,8-diaza-spiro[4.5]decan-1-one hydrochloride (31 mg, 0.16 mmol) in a manner analogous to that used for the synthesis of compound 31-3 to give compound 50-2.
Yield: 60 mg
ES mass spectrum: [M+H]+=521
Retention time HPLC: 1.36 min (HPLC Method 4)

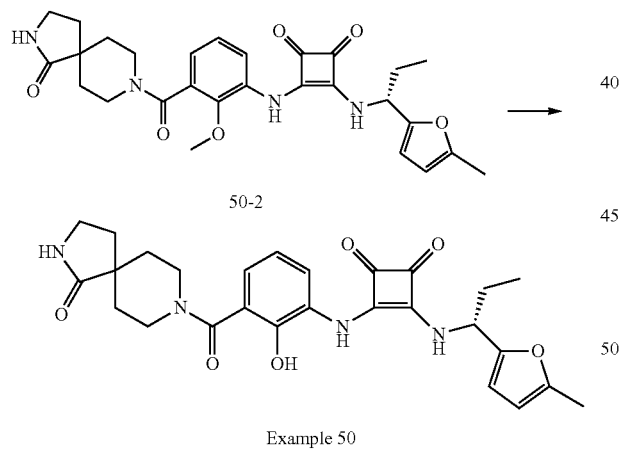

50-2

Example 50

Compound 50-2 (60 mg, 0.11 mmol) is dissolved in 2,4,6-collidine and lithium iodide (77 mg, 0.57 mmol) is added. The mixture is heated in a sealed tube at 120° C. for 12 hours. The mixture is filtered and the solvent removed under vacuum. The residue is purified by semi-preparative HPLC to give Example 50.
Yield: 8 mg
ES mass spectrum: [M+H]+=529
Retention time HPLC: 9.40 min (HPLC Method 6)
$^1$H NMR (Varian Inova 500 MHz. DMSO-d6; 27° C.) 9.50 (3H, br); 8.65 (1H, d); 7.78 (1H, d); 7.58 (1H, s); 6.84 (1H, m); 6.24 (1H, m); 6.03 (1H, d); 5.14 (1H, d); 3.9 (2H, br); 3.09-3.19 (3H, m); 2.26 (3H, s); 1.99 (4H, m); 1.86 (1H, m); 1.67 (2H, m); 1.39 (2H, m); 0.92 (3H, t).

Synthesis of Example 51

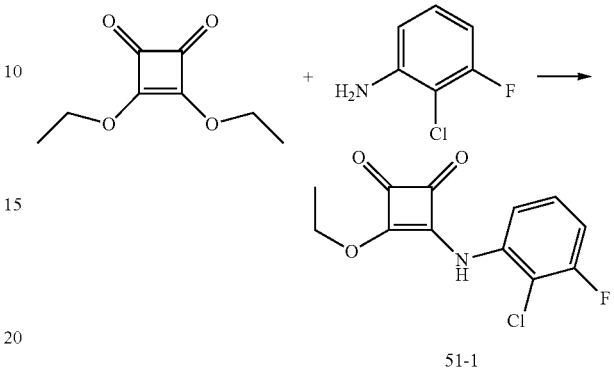

51-1

3,4-Diethoxy-3-cyclobutene-1,2-dione (1.5 g, 8.82 mmol), 2-chloro-3-fluoroaniline (1.28 g, 8.82 mmol) and hydrochloric acid (37%, 0.5 mL, 6 mmol) are dissolved in absolute ethanol (40 mL) and heated at reflux for 4 hours. The solvent is removed under vacuum, the residue suspended in 1:1 DCM/diethyl ether and filtered. The solute is washed with 10% aqueous sodium bicarbonate, dried and the solvent removed. The residue is purified by flash chromatography (silica gel, ethyl acetate/cyclohexane 3:7) to give compound 51-1
Yield: 550 mg
ES mass spectrum: [M+H]+=270
Retention time HPLC: 1.02 min (HPLC method 1)

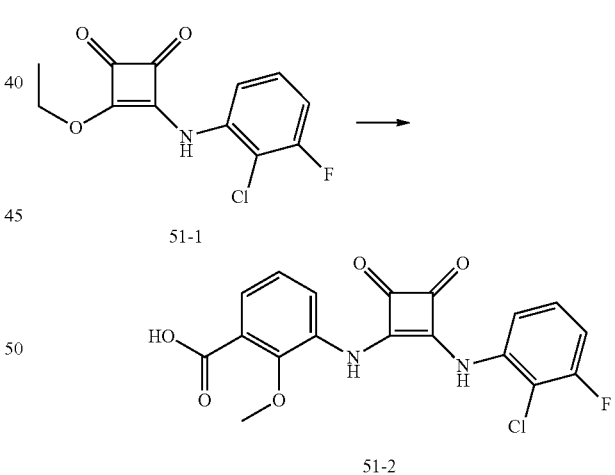

51-1

51-2

Compound 51-1 (550 mg, 2.14 mmol), 3-amino-2-methoxy benzoic acid (341 mg, 2.04 mmol) and triethylamine (340 μL, 2.45 mmol) are suspended in ethanol (25 mL) and refluxed for 10 hours. The solution is concentrated to 15 mL, diluted with water (30 mL), cooled to 0° C. and acidified with 6 M hydrochloric acid to approximately pH 2. The formed precipitate is filtered off, washed with water and dried under vacuum to give compound 51-2.
Yield: 650 mg
ES mass spectrum: [M+H]+=390
Retention time HPLC: 1.63 min (HPLC Method 4)

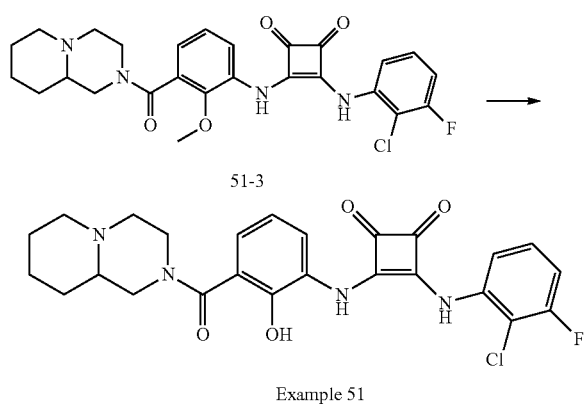

51-3

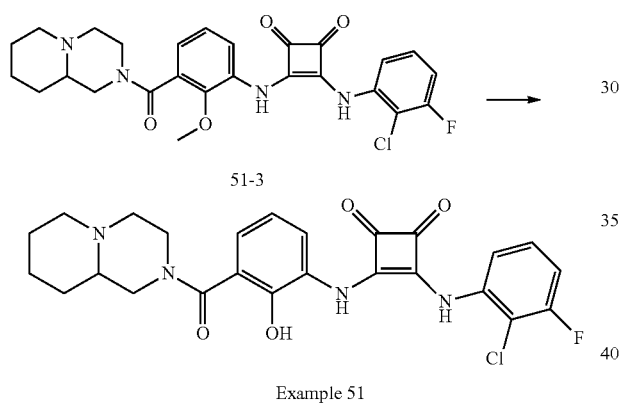

Example 51

Compound 51-2 (35 mg, 0.09 mmol) is reacted with octahydro-pyrido[1,2-a]pyrazine (14 mg, 0.10 mmol) in a manner analogous to that used for the synthesis of compound 31-3 to give compound 51-3.
Yield: 40 mg
ES mass spectrum: [M+H]+=513
Retention time HPLC: 0.76 min (HPLC Method 4)

51-3

Example 51

Compound 51-3 (40 mg, 0.08 mmol) is treated in a manner analogous to that used for the synthesis of example 31 to give Example 51.
Yield: 6 mg
ES mass spectrum: [M+H]+=499
Retention time HPLC: 8.03 min (HPLC Method 5)
$^1$H NMR (Varian 400 MHz. DMSO-d6; 28° C.) 10.05 (2H, s+s); 10.02 (1H, s); 9.50 (1H, s); 7.63 (1H, d); 7.45-7.35 (2H, m); 7.19 (1H, m) 7.00 (2H, m); 4.55 (2H, br); 3.45 (2H, m); 3.15-2.90 (5H, m); 1.95-1.30 (6H, m)

Synthesis of Example 52

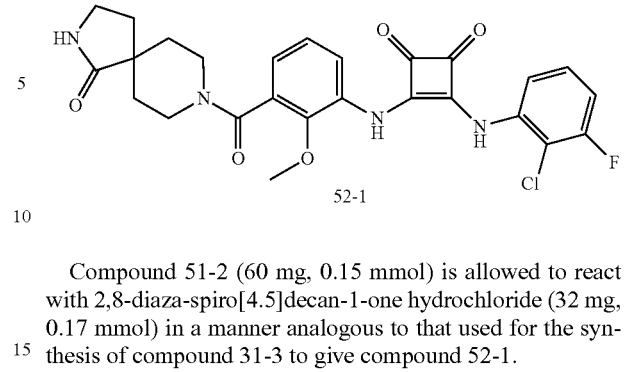

52-1

Compound 51-2 (60 mg, 0.15 mmol) is allowed to react with 2,8-diaza-spiro[4.5]decan-1-one hydrochloride (32 mg, 0.17 mmol) in a manner analogous to that used for the synthesis of compound 31-3 to give compound 52-1.
Yield: 35 mg
ES mass spectrum: [M+H]+=527
Retention time HPLC: 1.25 min (HPLC Method 4)

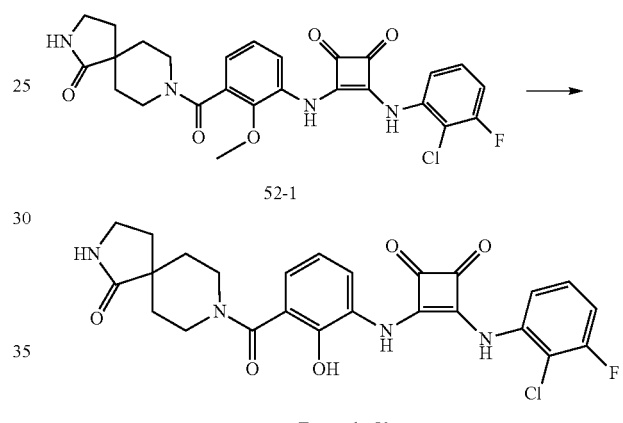

52-1

Example 52

Compound 52-1 (35 mg, 0.06 mmol) is treated in a manner analogous to that used for the synthesis of example 31 to give Example 52.
Yield: 8 mg
ES mass spectrum: [M+H]+=513
Retention time HPLC: 6.98 min (HPLC Method 5)
$^1$H NMR (Varian 400 MHz. DMSO-d6; 28° C.) 10.10 (1H, br); 10.03 (1H, s); 9.87 (1H, s); 7.58 (2H, m); 7.40 (2H, m); 7.17 (1H, t); 6.92 (2H, d); 3.86 (2H, m br); 3.15 (4H, m); 1.99 (2H, m); 1.68 (2H, m); 1.41 (2H, m).

Synthesis of Example 53

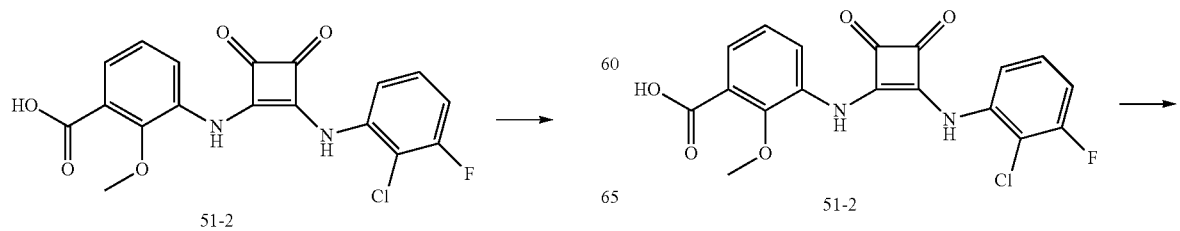

51-2

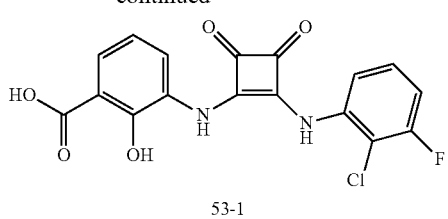

53-1

Compound 51-2 (240 mg, 0.61 mmol) is suspended in dry DCM (20 mL) and cooled to 0° C. Boron tribromide (1 M in DCM, 3.07 mL, 3.07 mmol) is added and the mixture stirred for 12 hours at room temperature. Methanol (1.8 mL) and water (0.2 mL) are added and the solvent is removed, the residue is triturated with water:acetonitrile 8:2 (10 mL) and diethyl ether:acetone (1:1) and dried under vacuum to give compound 53-1.

Yield: 170 mg

ES mass spectrum: [M+H]+=377

Retention time HPLC: 1.88 min (HPLC Method 4)

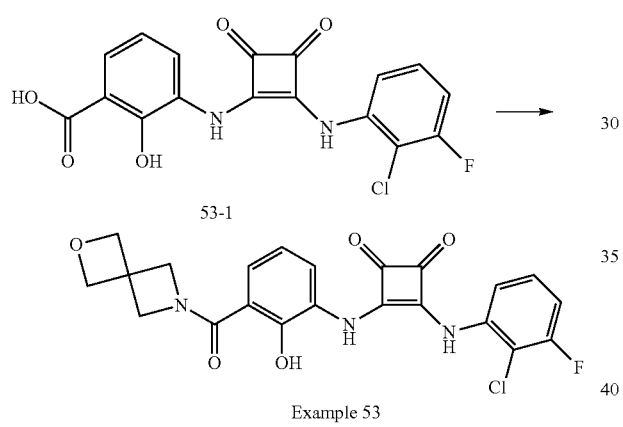

53-1

Example 53

Compound 53-1 is treated in a manner analogous to that used for the synthesis of example 36 to give Example 53.

Yield: 14 mg

ES mass spectrum: [M+H]+=458

Retention time HPLC: 10.64 min (HPLC Method 5)

$^1$H NMR (Varian 400 MHz. DMSO-d6; 28° C.) 10.1 (3H, br); 7.82 (1H, d); 7.39 (2H, m); 7.22 (1H, m); 7.17 (1H, m); 6.92 (1H, t); 4.78 (2H, br); 4.71 (4H, s); 4.33 (2H, br).

Synthesis of Example 54

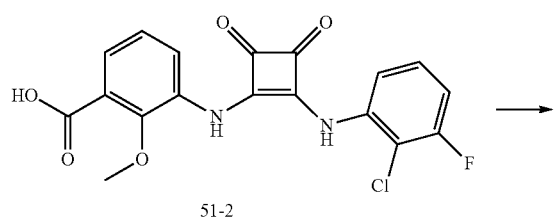

51-2

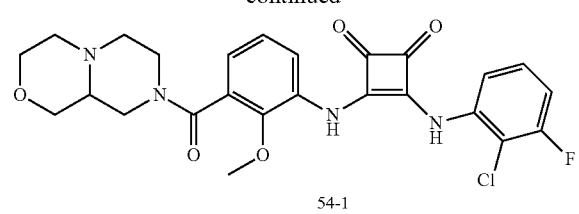

54-1

Compound 51-2 (80 mg, 0.20 mmol) is allowed to react with compound 17-6 (32 mg, 0.23 mmol) in a manner analogous to that used for the synthesis of compound 31-3 to give compound 54-1.

Yield: 20 mg

ES mass spectrum: [M+H]+=515

Retention time HPLC: 3.04 min (HPLC Method 4)

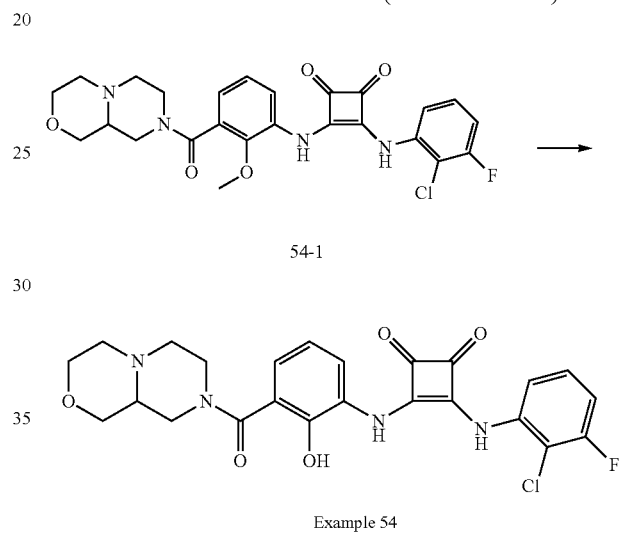

54-1

Example 54

Compound 54-1 (35 mg, 0.06 mmol) is treated in a manner analogous to that used for the synthesis of example 31 to give Example 54.

Yield: 8 mg

ES mass spectrum: [M+H]+=501

Retention time HPLC: 7.02 min (HPLC Method 5)

$^1$H NMR (Varian 400 MHz. DMSO-d6; 28° C.) 8.22 (1H, s); 7.63 (1H, m); 7.43 (1H, m); 7.32 (1H, m); 7.10 (1H, t); 6.89 (2H; m); 3.72 (2H, m); 3.65 (2H, m); 3.50 (2H, m); 3.07 (2H, m); 2.67 (2H, m); 2.20-2.10 (3H, m). 2H not observed.

Synthesis of Example 55

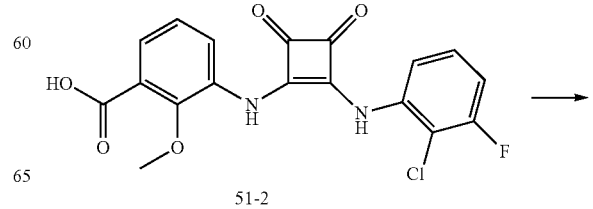

51-2

95
-continued

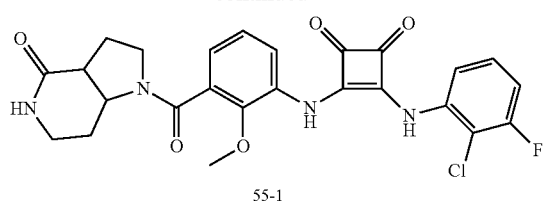

55-1

Compound 51-2 (70 mg, 0.18 mmol) is reacted with octahydro-pyrrolo[3,2-c]pyridine-4-one hydrochloride (35 mg, 0.20 mmol) in a manner analogous to that used for the synthesis of compound 31-3 to give compound 55-1.

Yield: 45 mg

ES mass spectrum: [M+H]+=513

Retention time HPLC: 1.00 min (HPLC Method 4)

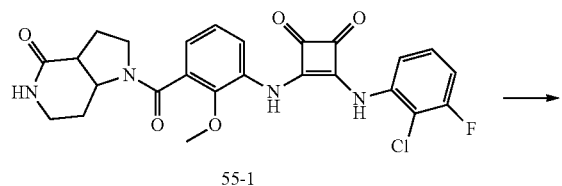

55-1

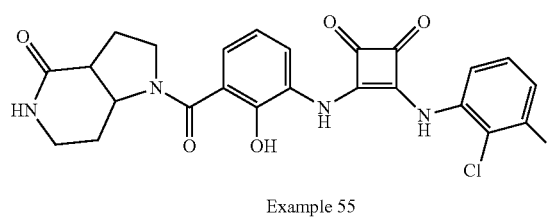

Example 55

Compound 55-1 (45 mg, 0.09 mmol) is treated in a manner analogous to that used for the synthesis of example 31 to give Example 55.

Yield: 8 mg

ES mass spectrum: [M+H]+=499

Retention time HPLC: 6.85 min (HPLC Method 5)

$^1$H NMR (Varian 400 MHz. DMSO-d6; 28° C.) 10.97 (1H, br); 10.11 (2H, br); 7.70 (2H, br m); 7.41 (2H, m); 7.19 (2H, m); 6.91 (1H, m); 4.44 (1H, br m); 3.48 (1H, br m); 3.10 (2H, m br); 2.87 (1H, m); 2.12 (3H, m); 1.85 (1H, br m); 1.57 (1H, br m).

Synthesis of Example 56

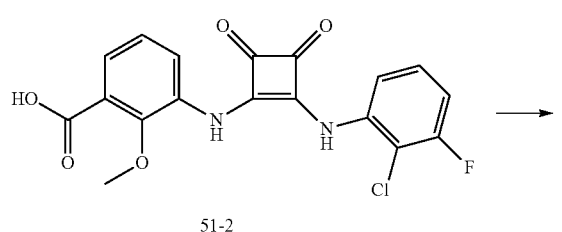

51-2

96
-continued

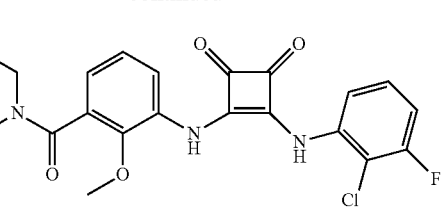

56-1

Compound 51-2 (70 mg, 0.18 mmol) is reacted with hexahydro-pyrrolo[1,2-a]pyrazi-4-one (39 mg, 0.28 mmol) in a manner analogous to that used for the synthesis of compound 31-3 to give compound 56-1.

Yield: 35 mg

ES mass spectrum: [M+H]+=513

Retention time HPLC: 1.45 min (HPLC Method 4)

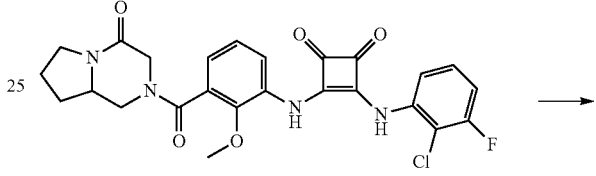

56-1

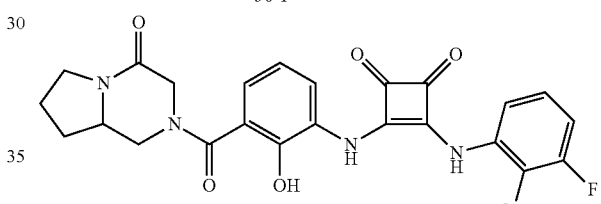

Example 56

Compound 56-1 (35 mg, 0.07 mmol) is treated in a manner analogous to that used for the synthesis of example 31 to give Example 56.

Yield: 8 mg

ES mass spectrum: [M+H]+=499

Retention time HPLC: 9.45 min (HPLC Method 6)

$^1$H NMR (Varian 400 MHz. DMSO-d6; 28° C.) 10.09 (1H, s); 10.04 (1H, s); 9.98 (1H, s); 7.63 (1H, dd); 7.44-7.38 (2H, m); 7.17 (1H, t); 6.98 (2H, m); 4.54 (1H, br); 3.95-3.60 (3H, br); 3.44 (1H, m); 3.09 (1H, m); 2.99 (1H, br); 2.05-1.65 (3H, br); 1.41 (1H, m).

EXAMPLES

Other features and advantages of the present invention will become apparent from the following more detailed examples which illustrate, by way of example, the principles of the invention.

Chemotaxis assay 1, transfected cell line: This assay measures the inhibition of CXCL1 induced chemotaxis of BAF/3 cells expressing human CXCR2. For each assay point, 100 μL of a 3×10$^6$/mL cell suspension are incubated with 1 μL of test compound diluted in DMSO. The bottom wells of a chemotaxis plate (5 μm pore size, Neuroprobe) is filled with 305 μL of chemotaxis buffer (RPMI 1640 medium (phenol red free), containing 2% fetal calf serum) and 3 nM CXCL1. The 5 μm pore membrane is applied onto the chemotaxis plate and 80

µL of the cell suspension is cautiously pipetted onto the membrane. The lid is put on the chemotaxis plate and the plate is incubated for 4 hours in an incubator (37° C., 5% CO2). For quantification of migrated cells, the cell suspension and the lid are removed and 100 µL from the bottom chamber are transferred to an Opti plate 96 (Perkin Elmer). 100 µL of substrate solution (provided by Cell Titer Glo kit, Promega) are added. This method uses the measurement of ATP present in metabolically active cells. After 10 min incubation at room temperature the plate is measured at Luminoscan for quantification of ATP-dependent generation of oxyluciferin. IC50s of the tested compound are calculated by non-linear regression and using a sigmoidal dose-response curve as fitting algorithm (provided by GraphPadPrism). Determination of a bottom value is performed by quantification of migration of buffer treated cells, migrating towards buffer only. Determination of a top value is performed by quantification of migration of buffer treated cells, migrating towards CXCL1.

Chemotaxis assay 2, primary human PMN (polymorph nuclear cells) from healthy donors: This assay measures the inhibition of CXCL1 induced chemotaxis of primary human PMN cells isolated from healthy donors. Neutrophils, the major type of human PMN cells express both CXCR1 and CXCR2. CXCL1 specifically binds to CXCR2, not CXCR1 and therefore, upon stimulation with CXCL1 measurements are focused on CXCR2. For the isolation of PMN cells, human whole blood is mixed with DPBS and ACD buffer (38 mM citric acid, 75 mM tri-sodium citrate, 121 mM glucose) to prevent coagulation. Blood, DPBS and ACD buffer are mixed at a ratio of 4:1:1. For separation of PMN cells from mononuclear cells, the anti-coagulated blood is layered over 18-20 mL Ficoll (Ficoll-Paqu™ Plus) and centrifuged for 30 mM at 300×g, without brake. Supernatant containing mononuclear cells is discarded. Pellet contains PMN cells and erythrocytes. For lysis of erythrocytes, the pellet is suspended with 30 mL of ammonium hydroxide buffer (155 mM $NH_4Cl$, 10 mM $KHCO_3$, 0.1 mM EDTA, pH 5.0) and incubated for 8 minutes on ice. After centrifugation (5 minutes at 300×g), supernatant is discarded and the pellet is treated a second time with ammonium hydroxide buffer, incubated for 8 minutes on ice. After centrifugation (5 minutes at 300×g) supernatant is discarded and the pellet containing the PMN in suspended in HBSS containing 0.1% BSA. Cell number is adjusted to $2.5 \times 10^6$/ml. 100 µL cell suspension is incubated with 1 µL compound dissolved in DMSO for 20 minutes at room temperature. The bottom wells of a 5 µm pore chemotaxis plate (Neuro-Probe) are filled with either 305 µL HBSS buffer (negative control) of HBSS buffer containing 10 nM CXCL1. The membrane is applied onto the chemotaxis plate and 80 µl of the cell suspension is cautiously pipetted onto the membrane. The lid is put on the chemotaxis plate and the plate is incubated for 1 hour in an incubator (37° C., 5% CO2). For quantification of migrated cells, the cell suspension and the lid are removed and 100 µl from the bottom chamber are transferred to an Opti plate 96 (Perkin Elmer). 100 µl of substrate solution (provided by Cell Titer Glo kit, Promega) are added. After 10 min incubation at room temperature the plate is measured at Luminoscan. IC50s of the tested compound are calculated by non-linear regression and using a sigmoidal dose-response curve as fitting algorithm (provided by GraphPadPrism). Determination of a bottom value was performed by quantification of migration of buffer treated cells, migrating towards buffer only. Determination of a top value was performed by quantification of migration of buffer treated cells, migrating towards CXCL1.

The above mentioned pharmacokinetic properties are measured using methods similar to those described in E. H. Kerns, D. Li: Drug-like Properties: Concepts, Structure, Design and Methods: from ADME to Toxicity Optimization. Academic Press 2008, Burlington, Mass., USA. Chapter 19: Pharmacokinetics, pp 228-241.

All of the referenced examples have been found to have an activity in the above described chemotaxis assay 1 as reported below.

| Example | $IC_{50}$ (nM) |
| --- | --- |
| 1 | 597 |
| 3 | 634 |
| 4 | 34 |
| 5 | 377 |
| 7 | 2570 |
| 8 | 651 |
| 9 | 22 |
| 10 | 260 |
| 11 | 41 |
| 12 | 119 |
| 13 | 47 |
| 14 | 11 |
| 15 | 86 |
| 16 | 85 |
| 17 | 1.2 |
| 18 | 11 |
| 19 | 50 |
| 20 | 16 |
| 21 | 8 |
| 22 | 1.5 |
| 23 | 2740 |
| 24 | 3.2 |
| 25 | 1350 |
| 26 | 3.9 |
| 27 | 0.1 |
| 28 | 40 |
| 29 | 4.1 |
| 30 | 267 |
| 31 | 662 |
| 32 | 401 |
| 34 | 126 |
| 35 | 16 |
| 36 | 25 |
| 37 | 26 |
| 38 | 3.4 |
| 39 | 23 |
| 40 | 34 |
| 41 | 66 |
| 42 | 45 |
| 43 | 11 |
| 44 | 2130 |
| 45 | 3.3 |
| 46 | 51 |
| 47 | 818 |
| 48 | 859 |
| 49 | 926 |
| 50 | 1852 |
| 51 | 247 |
| 52 | 6.2 |
| 53 | 360 |
| 54 | 67 |
| 55 | 617 |
| 56 | 865 |

Combinations

The compounds of formula 1 may be used on their own or in conjunction with other active substances of formula 1 according to the invention. If desired the compounds of formula 1 may also be used in combination with other pharmacologically active substances. It is preferable to use for this purpose active substances selected for example from among β2-adrenoceptor-agonists (short and lon-acting betamimetics), anti-cholinergics (short and lon-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, statins, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK (spleen tyrosine kinase-inhibitors), ZAP-70, FYN, BTK or ITK, inhibitors of MAP kinases as for example p38, ERK1, ERK2, INK1, JNK2, JNK3 or SAP, inhibitors of the NF-kappaB signalling pathway as for example IKK2 kinase inhibitors, iNOS inhibitors (inducible nitric oxide synthase-inhibitors), MRP4 inhibitors, leukotriene antagonists, leukotriene biosynthese inhibitors as for example 5-Lipoxygenase (5-LO) inhibitors, cPLA2 inhibitors, Leukotriene A4 Hydrolase inhibitors or FLAP inhibitors, non-steroidal antiinflammatory drugs (NSAIDs) including COX-2 inhibitors, CRTH2 antagonists, DP1-receptor modulators, Thromboxane receptor antagonists, CCR1 antagonists, CCR2 antagonists, CCR4 antagonists, CCR5 antagonists, CCR6 antagonists, CCR7 antagonists, CCR8 antagonists, CCR9 antagonists, CCR10 antagonists, CCR11 antagonists, CXCR3 antagonists, CXCR4 antagonists, CXCR5 antagonists, CXCR6 antagonists, CX3CR1 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic receptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, Somatostatin receptor agonists, TNFalpha antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, antiviral drugs, opiate receptor agonists, cannabinoid agonists, sodium channel blockers, N-type calcium channel blockers, serotonergic and noradrenergic modulators, proton pump inhibitors, local anaesthetics, VR1 agonists and antagonists, Nicotinic acetylcholine receptor agonists, P2X3 receptor antagonists, NGF agonists and antagonists, NMDA antagonist, potassium channel modulators, GABA modulators, serotonergic and noradrenergic modulators, anti-migraine drugs. The invention also encompasses combinations of three active substances, each selected from one of the above-mentioned categories of compounds. Said list is not considered to have a limiting character.

The compounds of formula 1 may be used on their own or in conjunction with other active substances of formula I according to the invention. If desired the compounds of formula I may also be used in combination with other pharmacologically active substances. It is preferable to use for this purpose active substances selected for example from among β2-adrenoceptor-agonists (short and lon-acting betamimetics), anti-cholinergics (short and lon-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, statins, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK (spleen tyrosine kinase-inhibitors), ZAP-70, FYN, BTK or ITK, inhibitors of MAP kinases as for example p38, ERK1, ERK2, INK1, JNK2, JNK3 or SAP, inhibitors of the NF-kappaB signalling pathway as for example IKK2 kinase inhibitors, iNOS inhibitors (inducible nitric oxide synthase-inhibitors), MRP4 inhibitors, leukotriene antagonists, leukotriene biosynthese inhibitors as for example 5-Lipoxygenase (5-LO) inhibitors, cPLA2 inhibitors, Leukotriene A4 Hydrolase inhibitors or FLAP inhibitors, non-steroidal antiinflammatory drugs (NSAIDs) including COX-2 inhibitors, CRTH2 antagonists, DP1-receptor modulators, Thromboxane receptor antagonists, CCR1 antagonists, CCR4 antagonists, CCR5 antagonists, CCR6 antagonists, CCR7 antagonists, CCR8 antagonists, CCR9 antagonists, CCR10 antagonists, CCR11 antagonists, CXCR1 antagonists, CXCR2 antagonists, CXCR3 antagonists, CXCR4 antagonists, CXCR5 antagonists, CXCR6 antagonists, CX3CR1 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic rezeptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, TNFalpha antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds agianst swelling of the airways, compounds against cough, antiviral drugs, opiate receptor agonists, cannabionoid agonists, sodium channel blockers, N-type calcium channel blockers, serotonergic and noradrenergic modulators, proton pump inhibitors, local anesthetics, VR1 agonists and antagonists, Nicotinic acetylcholine receptor agonists, P2X3 receptor antagonists, NGF agonists and antagonists, NMDA antagonist, potassium channel modulators, GABA modulators, serotonergic and noradrenergic modulators, anti-migraine drugs. The invention also encompasses combinations of three active substances, each selected from one of the above-mentioned categories of compounds. Said list is not considered to have a limiting character.

Examples of preferred betamimetics which may be mentioned include Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Milveterol, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, Nolomirole, and
1-(2-chloro-4-hydroxyphenyl)-t-butylaminoethanole,
(−)-2-[7(S)-[2(R)-Hydroxy-2-(4-hydroxyphenyl)-ethylamino]-5,6,7,8-tetrahydro-2-naphthyloxy]-N,N-dimethylacetamide hydrochloride monohydrate, 3-(4-{6-[2-Hydroxy-2-(4-hydroxy-3-hydroxymethyl-phenyl)-ethylamino]-hexyloxy}-butyl)-benzyl-sulfonamide 5-[2-(5,6-Diethyl-indan-2-ylamino)-1-hydroxy-ethyl]-8-hydroxy-1H-quinoline-2-one 4-Hydroxy-7-[2-{[2-{[3-(2-phenylethoxy)propyl]sulphonyl}ethyl]-amino}ethyl]-2(3H)-benzothiazolone 1-(2-Fluoro-4-hydroxyphenyl)-2-[4-(1-benzimidazolyl)-2-methyl-2-butylamino]ethanole 1-[3-(4-Methoxybenzyl-amino)-4-hydroxyphenyl]-2-[4-(1-benzimidazolyl)-2-methyl-2-butylamino]ethanole 1-[2H-5-hydroxy-3-oxo-4H-1,4-benzoxazin-8-yl]-2-[3-(4-N,N-dimethylaminophenyl)-2-methyl-2-propylamino]ethanole 1-[2H-5-hydroxy-3-oxo-4H-1,4-benzoxazin-8-yl]-2-[3-(4-methoxyphenyl)-2-methyl-2-propylamino]ethanole 1-[2H-5-hydroxy-3-oxo-4H-1,4-benzoxazin-8-yl]-2-[3-(4-n-butyloxyphenyl)-2-methyl-2-propylamino]ethanole 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanole 5-Hydroxy-8-(1-hydroxy-2-isopropylaminobutyl)-2H-1,4-benzoxazin-3-(4H)-one 1-(4-Amino-3-chloro-5-trifluormethylphenyl)-2-tert.-butylamino)ethanole 6-Hydroxy-8-{1-hydroxy-2-[2-(4-methoxy-phenyl)-1,1-dimethyl-ethylamino]-ethyl}-4H-benzo[1,4]oxazin-3-one 6-Hydroxy-8-{1-hydroxy-2-[2-(4-phenoxy-acetic acid ethylester)-1,1-dimethyl-ethylamino]-ethyl}-4H-benzo[1,4]oxazin-3-one 6-Hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-Dimethyl-2-(2,4,6-trimethylphenyl)-ethylamino]-1-hydroxy-ethyl}-6-hydroxy-4H-benzo[1,4]oxazin-3-one 6-Hydroxy-8-{1-hydroxy-2-[2-(4-hydroxy-phenyl)-1,1-dimethyl-ethylamino]-ethyl}-4H-benzo[1,4]oxazin-3-one 6-Hydroxy-8-{1-hydroxy-2-[2-(4-isopropyl-phenyl)-1,1-dimethyl-ethylamino]-ethyl}-4H-benzo[1,4]oxazin-3-one 8-{2-[2-(4-Ethyl-phenyl)-1,1-dimethyl-ethylamino]-1-hydroxy-ethyl}-6-hydroxy-4H-benzo[1,4]oxazin-3-one 8-{2-[2-(4-Ethoxy-phenyl)-1,1-dimethyl-ethylamino]-1-hydroxy-ethyl}-6-hydroxy-4H-benzo[1,4]oxazin-3-one 4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-Difluor-phenyl)-1,1-dimethyl-ethylamino]-1-hydroxy-ethyl}-6-hydroxy-4H-benzo[1,4]oxazin-3-one 1-(4-Ethoxy-carbonylamino-3-cyano-5-fluorophenyl)-2-(tert.-butylamino)ethanole N-[2-Hydroxy-5-(1-hydroxy-2-{2-[4-(2-hydroxy-2-phenyl-ethylamino)-phenyl]-ethylamino}-ethyl)-phenyl]-formamide 8-Hydroxy-5-(1-hydroxy-2-{2-[4-(6-methoxy-biphenyl-3-ylamino)-phenyl]-ethylamino}-ethyl)-1H-quinolin-2-one 8-Hydroxy-5-[1-hydroxy-2-(6-phenethylamino-hexylamino)-ethyl]-1H-quinolin-2-one 5-[2-(2-{4-[4-(2-Amino-2-methyl-propoxy)-phenylamino]-phenyl}-ethylamino)-1-hydroxy-ethyl]-8-hydroxy-1H-quinolin-2-one

[3-(4-{6-[2-Hydroxy-2-(4-hydroxy-3-hydroxymethyl-phenyl)-ethylamino]-hexyloxy}-butyl)-5-methyl-phenyl]-urea 4-(2-{6-[2-(2,6-Dichloro-benzyloxy)-ethoxy]-hexylamino}-1-hydroxy-ethyl)-2-hydroxymethyl-phenole 3-(4-{6-[2-Hydroxy-2-(4-hydroxy-3-hydroxymethyl-phenyl)-ethylamino]-hexyloxy}-butyl)-benzenesulfonamide 3-(3-{7-[2-Hydroxy-2-(4-hydroxy-3-hydroxymethyl-phenyl)-ethylamino]-heptyloxy}-propyl)-benzenesulfonamide 4-(2-{6-[4-(3-Cyclopentanesulfonyl-phenyl)-butoxy]-hexylamino}-1-hydroxy-ethyl)-2-hydroxymethyl-phenole N-Adamantan-2-yl-2-(3-{2-[2-hydroxy-2-(4-hydroxy-3-hydroxymethyl-phenyl)-ethylamino]-propyl}-phenyl)-acetamide (R,S)-4-(2-{[6-(2,2-Difluoro-4-phenylbutoxy)hexyl]amino}-1-hydroxy-ethyl)-2-(hydroxymethyl)phenole (R,S)-4-(2-{[6-(2,2-Difluoro-2-phenylethoxy)hexyl]amino}-1-hydroxy-ethyl)-2-(hydroxymethyl)phenole (R,S)-4-(2-{[4,4-Difluoro-6-(4-phenylbutoxy)hexyl]amino}-1-hydroxy-ethyl)-2-(hydroxymethyl)phenole (R,S)-4-(2-{[6-(4,4-Difluoro-4-phenylbutoxy)hexyl]amino}-1-hydroxy-ethyl)-2-(hydroxymethyl)phenole (R,S)-5-(2-{[6-(2,2-Difluoro-2-phenylethoxy)hexyl]amino}-1-hydroxy-ethyl)-8-hydroxyquinolin-2(1H)-one (R,S)-[2-({6-[2,2-Difluoro-2-(3-methylphenyl)ethoxy]hexyl}amino)-1-hydroxyethyl]-2-(hydroxymethyl)phenole 4-(1R)-2-{[6-(2,2-Difluoro-2-phenylethoxy)hexyl]amino}-1-hydroxyethyl)-2-(hydroxymethyl)phenol (R,S)-2-(Hydroxymethyl)-4-(1-hydroxy-2-{[4,4,5I5-tetrafluoro-6-(3-phenylpropoxy)-hexyl]amino}ethyl)phenole (R,S)-[5-(2-{[6-(2,2-Difluoro-2-phenylethoxy)hexyl]amino}-1-hydroxy-ethyl)-2-hydroxyphenyl]formamide (R,S)-4-(2-({6-[2-(3-Bromophenyl)-2,2-difluoroethoxy]hexyl}amino)-1-hydroxyethyl]-2-(hydroxymethyl)phenole (R,S)—N-[3-(1,1-Difluoro-2-{[6-({2-hydroxy-2-[4-hydroxy-3-(hydroxymethyl)phenyl]-ethyl}amino)hexyl]oxy}ethyl)phenyl]urea 3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione (R,S)-4-[2-({6-[2,2-difluoro-2-(3-methoxyphenyl)ethoxy]hexyl}amino)-1-hydroxyethyl]-2-(hydroxymethyl)phenole 5-((1R)-2-{[6-(2,2-difluoro-2-phenylethoxy)hexyl]amino}-1-hydroxyethyl)-8-hydroxyquinolin-2(1H)-one 4-((1R)-2-{[4,4-Difluoro-6-(4-phenylbutoxy)hexyl]amino}-1-hydroxy-ethyl)-2-(hydroxymethyl)phenole (R,S)-4-(2-{[6-(3,3-Difluoro-3-phenylpropoxy)hexyl]amino}-1-hydroxy-ethyl)-2-(hydroxymethyl)phenole (R,S)-4-(2-{[6-(2,2-Difluoro-2-phenylethoxy)-4,4-difluorohexyl]amino}-1-hydroxyethyl)-2-(hydroxymethyl)phenole (R,S)-4-(2-{[6-(2,2-difluoro-3-phenylpropoxy)hexyl]amino}-1-hydroxy ethyl)-2-(hydroxymethyl)phenole 3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide 7-[2-(2-{3-[2-(2-Chloro-phenyl)-ethylamino]-propylsulfanyl}-ethylamino)-1-hydroxy-ethyl]-4-hydroxy-3H-benzothiazol-2-one and 7-[(1R)-2-(2-{3-[2-(2-Chloro-phenyl)-ethylamino]-propylsulfanyl}-ethylamino)-1-hydroxy-ethyl]-4-hydroxy-3H-benzothiazol-2-one optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred anticholinergics which may be mentioned include Tiotropium salts, preferred the bromide salt, Oxitropium salts, preferred the bromide salt, Flutropium salts, preferred the bromide salt, Ipratropium salts, preferred the bromide salt, Aclidinium salts, preferred the bromide salt, Glycopyrronium salts, preferred the bromide salt, Trospium salts, preferred the chloride salt, Tolterodin. From the above mentioned salts the pharmacologically active part is the cation, possible anions are chloride, bromide, iodide, sulfate, phosphate, methansulfonate, nitrate, maleate, acetate, citrate, fumarate, tartrate, oxalate, succinate, benzoate or p-toluenesulfonate. Further examples of preferred anticholinergics are selected from among 2,2-Diphenylpropionic acid tropenole ester-methobromide
2,2-Diphenylpropionic acid scopine ester-methobromide
2-Fluor-2,2-Diphenylacetic acid scopine ester-methobromide
2-Fluor-2,2-Diphenylacetic acid tropenole ester-methobromide
3,3',4,4'-Tetrafluorbenzil acid tropenole ester-methobromide
3,3',4,4'-Tetrafluorbenzil acid scopine ester-methobromide
4,4'-Difluorbenzil acid tropenole ester-methobromide
4,4'-Difluorbenzil acid scopine ester-methobromide
3,3'-Difluorbenzil acid tropenole ester-methobromide
3,3'-Difluorbenzil acid scopine ester-methobromide
9-Hydroxy-fluorene-9-carbon acid tropenole ester-methobromide
9-Fluor-fluorene-9-carbon acid tropenole ester-methobromide
9-Hydroxy-fluorene-9-carbon acid scopine ester-methobromide
9-Fluor-fluorene-9-carbon acid scopine ester methobromide
9-Methyl-fluorene-9-carbon acid tropenole estermethobromide
9-Methyl-fluorene-9-carbon acid scopine estermethobromide
Benzil acid cyclopropyl tropine ester-methobromide
2,2-Diphenylpropionic acid cyclopropyl tropine ester-methobromide
9-Hydroxy-xanthene-9-carbon acid cyclopropyl tropine ester-methobromide
9-Methyl-fluorene-9-carbon acid cyclopropyl tropine ester-methobromide
9-Methyl-xanthene-9-carbon acid cyclopropyl tropine ester-methobromide
9-Hydroxy-fluorene-9-carbon acid cyclopropyl tropine ester-methobromide
4,4'-Difluorbenzil acid methylester cyclopropyl tropine ester-methobromide
9-Hydroxy-xanthene-9-carbon acid tropenole ester-methobromide
9-Hydroxy-xanthene-9-carbon acid scopine ester methobromide
9-Methyl-xanthene-9-carbon acid tropenole ester-methobromide
9-Methyl-xanthene-9-carbon acid scopine estermethobromide
9-Ethyl-xanthene-9-carbon acid tropenole ester methobromide
9-Difluormethyl-xanthene-9-carbon acid tropenole ester-methobromide
9-Hydroxymethyl-xanthene-9-carbon acid scopine ester-methobromide.

Examples of preferred corticosteroids which may be mentioned include Beclomethasone, Betamethasone, Budesonide, Butixocorte, Ciclesonide, Deflazacorte, Dexamethasone, Etiprednole,
Flunisolide, Fluticasone, Loteprednole, Mometasone, Prednisolone, Prednisone, Rofleponide, Triamcinolone, Tepredane, and
{20R-16α,17α-[butylidenebis(oxy)]-6α,9α-difluoro-11β-hydroxy-17β-(methylthio)androsta-4-en-3-one},
9-fluoro-11beta,17,21-trihydroxy-16alpha-methylpregna-1,4-diene-3,20-dione 21-cyclohexanecarboxylate 17-cyclopropanecarboxylate,
16,17-butylidene dioxy-6,9-difluoro-11-hydroxy-17-(methylthio)androst-4-en-3-one
Flunisolide-21-[4'-(nitrooxymethyl)benzoate]
6,9-Difluoro-17-[(2-furanylcarbonyl)oxy]-11-hydroxy-16-methyl-3-oxo-androsta-1,4-dien-17-carbothion acid (S)-fluoromethylester,
6,9-Difluoro-11-hydroxy-16-methyl-3-oxo-17-propionyloxy-androsta-1,4-dien-17-carbothion acid (S)-(2-oxo-tetrahydro-furan-3S-yl)ester, and
6α,9α-difluoro-11β-hydroxy-16α-methyl-3-oxo-17α-(2,2,3,3-tertamethylcyclopropylcarbonyl)oxy-androsta-1,4-diene-17β-carboxylic acid cyanomethyl ester
optionally in racemic form, as enantiomers, diastereomeres or as pharmacologically acceptable salts, solvates or hydrates. Examples for preferred salts and derivatives are alkali salts, i.e. sodium or potassium salts, sulfobenzoates, phosphates, isonicotinates, acetates, dichloroacetates, propionates, dihydrogenphosphates, palmitates, pivalates or furoates.

Examples of preferred PDE4-inhibtors which may be mentioned include Enprofylline, Theophylline, Roflumilaste, Ariflo (Cilomilaste), Tofimilaste, Pumafentrine, Lirimilaste, Apremilaste, Arofylline, Atizorame, Oglemilastum, Tetomilaste and
5-[(N-(2,5-dichloro-3-pyridinyl)-carboxamide]-8-methoxyquinoline
5-[N-(3,5-dichloro-1-oxido-4-pyridinyl)-carboxamide]-8-methoxy-2-(trifluoromethyl)-quinoline
N-(3,5-dichloropyrid-4-yl)-[1-(4-fluorobenzyl)-5-hydroxyindole-3-yl]glyoxyl acid amide), 9-[(2-fluorophenyl)methyl]-N-methyl-2-(trifluoromethyl)-9H-purine-6-amine
4-[(2R)-2-[3-(cyclopentyloxy)-4-methoxyphenyl]-2-phenylethyl]-pyridine,
N-[(3R)-3,4,6,7-tetrahydro-9-methyl-4-oxo-1-phenylpyrrolo[3,2,1-jk][1,4]benzodiazepin-3-yl]-4-Pyridinecarboxamide,
4-[6,7-diethoxy-2,3-bis(hydroxymethyl)-1-naphthalenyl]-1-(2-methoxyethyl)-2(1H)-pyridinone
2-[4-[6,7-d]ethoxy-2,3-bis(hydroxymethyl)-1-naphthalenyl]-2-pyridinyl]-4-(3-pyridinyl)-1(2H)-Phthalazinone,
(3-(3-cyclopenyloxy-4-methoxybenzyl)-6-ethylamino-8-isopropyl-3H-purine,
beta-[3-(cyclopentyloxy)-4-methoxyphenyl]-1,3-dihydro-1,3-dioxo-2H-isoindole-2-propanamide,
9-ethyl-2-methoxy-7-methyl-5-propyl-imidazo[1,5-a]pyrido[3,2-e]pyrazin-6(5H)-one
5-[3-(cyclopentyloxy)-4-methoxyphenyl]-3-[(3-methylphenyl)methyl](3S,5S)-2-piperidinone,
4-[1-[3,4-bis(difluoromethoxy)phenyl]-2-(3-methyl-1-oxido-4-pyridinyl)ethyl]-alpha,alpha-bis(trifluoromethyl)-Benzenemethanol
N-(3,5-Dichloro-1-oxo-pyridine-4-yl)-4-difluoromethoxy-3-cyclopropylmethoxybenzamide (−)p-[(4aR*,10bS*)-9-Ethoxy-1,2,3,4,4a,10b-hexahydro-8-methoxy-2-methylbenzo[s][1,6]naphthyridin-6-yl]-N,N-diisopropylbenzamide (R)-(+)-1-(4-Bromobenzyl)-4-[(3-cyclopentyloxy)-4-methoxyphenyl]-2-pyrrolidone 3-(Cyclopentyloxy-4-methoxyphenyl)-1-(4-N'-[N-2-cyano-5-methyl-isothioureido]benzyl)-2-pyrrolidone cis[4-Cyano-4-(3-cyclopentyloxy-4-methoxyphenyl)cyclohexan-1-carbon acid]

2-carbomethoxy-4-cyano-4-(3-cyclopropylmethoxy-4-difluoromethoxyphenyl)cyclohexan-1-one cis[4-Cyano-4-(3-cyclopropylmethoxy-4-difluoromethoxyphenyl)cyclohexan-1-ol]

(R)-(+)-Ethyl[4-(3-cyclopentyloxy-4-methoxyphenyl)pyrrolidine-2-yliden]acetate (S)-(−)-Ethyl[4-(3-cyclopentyloxy-4-methoxyphenyl)pyrrolidine-2-yliden]acetate 9-Cyclopentyl-5,6-dihydro-7-ethyl-3-(2-thienyl)-9H-pyrazolo[3,4-c]-1,2,4-triazolo[4,3-a]pyridine 9-Cyclopentyl-5,6-dihydro-7-ethyl-3-(tert-butyl)-9H-pyrazolo[3,4-c]-1,2,4-triazolo[4,3-a]pyridine optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred EGFR-inhibitors which may be mentioned include Cetuximab, Trastuzumab, Panitumumab Gefitinib, Canertinib, Erlotinib, Mab ICR-62 and 4-[(3-Chlor-4-fluorphenyl)amino]-6-{[4-(morpholine-4-yl)-1-oxo-2-butene-1-yl]amino}-7-cyclopropylmethoxy-quinazoline 4-[(3-Chlor-4-fluorphenyl)amino]-6-{[4-(N,N-diethylamino)-1-oxo-2-butene-1-yl]amino}-7-cyclopropylmethoxy-quinazoline 4-[(3-Chlor-4-fluorphenyl)amino]-6-{[4-(N,N-dimethylamino)-1-oxo-2-butene-1-yl]amino}-7-cyclopropylmethoxy-quinazoline 4-[(R)-(1-Phenyl-ethyl)amino]-6-{[4-(morpholine-4-yl)-1-oxo-2-butene-1-yl]amino}-7-cyclopentyloxy-quinazoline 4-[(3-Chlor-4-fluor-phenyl)amino]-6-{[4-((R)-6-methyl-2-oxo-morpholine-4-yl)-1-oxo-2-butene-1-yl]amino}-7-cyclopropylmethoxy-quinazoline 4-[(3-Chlor-4-fluor-phenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline 4-[(3-Chlor-4-fluor-phenyl)amino]-6-{[4-((R)-2-methoxymethyl-6-oxo-morpholine-4-yl)-1-oxo-2-butene-1-yl]amino}-7-cyclopropylmethoxy-quinazoline 4-[(3-Chlor-4-fluor-phenyl)amino]-6-[2-((S)-6-methyl-2-oxo-morpholine-4-yl)-ethoxy]-7-methoxy-quinazoline 4-[(3-Chlor-4-fluorphenyl)amino]-6-({4-[N-(2-methoxy-ethyl)-N-methyl-amino]-1-oxo-2-butene-1-yl]amino}-7-cyclopropylmethoxy-quinazoline 4-[(3-Chlor-4-fluorphenyl)amino]-6-{[4-(N,N-dimethylamino)-1-oxo-2-butene-1-yl]amino}-7-cyclopentyloxy-quinazoline 4-[(R)-(1-Phenyl-ethyl)amino]-6-{[4-(N,N-bis-(2-methoxyethyl)-amino)-1-oxo-2-butene-1-yl]amino}-7-cyclopropylmethoxy-quinazoline 4-[(R)-(1-Phenyl-ethyl)amino]-6-({4-[N-(2-methoxyethyl)-N-ethyl-amino]-1-oxo-2-butene-1-yl]amino}-7-cyclopropylmethoxy-quinazoline 4-[(R)-(1-Phenyl-ethyl)amino]-6-({4-[N-(2-methoxyethyl)-N-methyl-amino]-1-oxo-2-butene-1-yl}amino)-7-cyclopropylmethoxy-quinazoline 4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline 4-[(3-Chlor-4-fluorphenyl)amino]-6-{[4-(N,N-dimethylamino)-1-oxo-2-butene-1-yl]amino}-7-((R)-tetrahydrofuran-3-yloxy)-quinazoline 4-[(3-Chlor-4-fluorphenyl)amino]-6-{[4-(N,N-dimethylamino)-1-oxo-2-butene-1-yl]amino}-7-((S)-tetrahydrofuran-3-yloxy)-quinazoline 4-[(3-Chlor-4-fluorphenyl)amino]-6-({4-[N-(2-methoxyethyl)-N-methyl-amino]-1-oxo-2-butene-1-yl}amino)-7-cyclopentyloxy-quinazoline 4-[(3-Chlor-4-fluorphenyl)amino]-6-{[4-(N-cyclopropyl-N-methyl-amino)-1-oxo-2-butene-1-yl]amino}-7-cyclopentyloxy-quinazoline 4-[(3-Chlor-4-fluorphenyl)amino]-6-{[4-(N,N-dimethylamino)-1-oxo-2-butene-1-yl]amino}-7-[(R)-(tetrahydrofuran-2-yl)methoxy]-quinazoline 4-[(3-Chlor-4-fluorphenyl)amino]-6-{[4-(N,N-dimethylamino)-1-oxo-2-butene-1-yl]amino}-7-[(S)-(tetrahydrofuran-2-yl)methoxy]-quinazoline 4-[(3-Ethinyl-phenyl)amino]-6,7-bis-(2-methoxy-ethoxy)-quinazoline 4-[(3-Chlor-4-fluorphenyl)amino]-7-[3-(morpholine-4-yl)-propyloxy]-6-[(vinylcarbonyl)amino]-quinazoline 4-[(R)-(1-Phenyl-ethyl)amino]-6-(4-hydroxy-phenyl)-7H-pyrrolo[2,3-d]pyrimidine 3-Cyano-4-[(3-chlor-4-fluorphenyl)amino]-6-{[4-(N,N-dimethylamino)-1-oxo-2-butene-1-yl]amino}-7-ethoxy-quinoline 4-{[3-Chlor-4-(3-fluor-benzyloxy)-phenyl]amino}-6-(5-{[(2-methansulfonyl-ethyl)amino]methyl}-furan-2-yl)quinazoline 4-[(R)-(1-Phenyl-ethyl)amino]-6-{[4-((R)-6-methyl-2-oxo-morpholine-4-yl)-1-oxo-2-butene-1-yl]amino}-7-methoxy-quinazoline 4-[(3-Chlor-4-fluorphenyl)amino]-6-{[4-(morpholine-4-yl)-1-oxo-2-butene-1-yl]amino}-7-[(tetrahydrofuran-2-yl)methoxy]-quinazoline 4-[(3-Chlor-4-fluorphenyl)amino]-6-({4-[N,N-bis-(2-methoxy-ethyl)-amino]-1-oxo-2-butene-1-yl}amino)-7-[(tetrahydrofuran-2-yl)methoxy]-quinazoline 4-[(3-Ethinyl-phenyl)amino]-6-{[4-(5,5-dimethyl-2-oxo-morpholine-4-yl)-1-oxo-2-butene-1-yl]amino}-quinazoline 4-[(3-Chlor-4-fluor-phenyl)amino]-6-[2-(2,2-dimethyl-6-oxo-morpholine-4-yl)-ethoxy]-7-methoxy-quinazoline 4-[(3-Chlor-4-fluor-phenyl)amino]-6-[2-(2,2-dimethyl-6-oxo-morpholine-4-yl)-ethoxy]-7-[(R)-(tetrahydrofuran-2-yl)methoxy]-quinazoline 4-[(3-Chlor-4-fluor-phenyl)amino]-7-[2-(2,2-dimethyl-6-oxo-morpholine-4-yl)-ethoxy]-6-[(S)-(tetrahydrofuran-2-yl)methoxy]-quinazoline 4-[(3-Chlor-4-fluor-phenyl)amino]-6-{2-[4-(2-oxo-morpholine-4-yl)-piperidin-1-yl]-ethoxy}-7-methoxy-quinazoline 4-[(3-Chlor-4-fluor-phenyl)amino]-6-[1-(tert.-butyloxycarbonyl)-piperidine-4-yloxy]-7-methoxy-quinazoline 4-[(3-Chlor-4-fluor-phenyl)amino]-6-(trans-4-amino-cyclohexane-1-yloxy)-7-methoxy-quinazoline 4-[(3-Chlor-4-fluor-phenyl)amino]-6-(trans-4-methanesulfonylamino-cyclohexane-1-yloxy)-7-methoxy-quinazoline 4-[(3-Chlor-4-fluor-phenyl)amino]-6-(tetrahydropyran-3-yloxy)-7-methoxy-quinazoline 4-[(3-Chlor-4-fluor-phenyl)amino]-6-(1-methyl-piperidine-4-yloxy)-7-methoxy-quinazoline 4-[(3-Chlor-4-fluor-phenyl)amino]-6-{1-[(morpholine-4-yl)carbonyl]-piperidine-4-yloxy}-7-methoxy-quinazoline 4-[(3-Chlor-4-fluor-phenyl)amino]-6-{1-[(methoxymethyl)carbonyl]-piperidine-4-yloxy}-7-methoxy-quinazoline 4-[(3-Chlor-4-fluor-phenyl)amino]-6-(piperidine-3-yloxy)-7-methoxy-quinazoline 4-[(3-Chlor-4-fluor-phenyl)amino]-6-[1-(2-acetylamino-ethyl)-piperidine-4-yloxy]-7-methoxy-quinazoline 4-[(3-Chlor-4-fluor-phenyl)amino]-6-(tetrahydropyran-4-yloxy)-7-ethoxy-quinazoline 4-[(3-Chlor-4-fluor-phenyl)amino]-6-((S)-tetrahydrofuran-3-yloxy)-7-hydroxy-quinazoline 4-[(3-Chlor-4-fluor-phenyl)amino]-6-(tetrahydropyran-4-yloxy)-7-(2-methoxy-ethoxy)-quinazoline 4-[(3-Chlor-4-fluor-phenyl)amino]-6-{trans-4-[(dimethylamino)sulfonylamino]-cyclohexane-1-yloxy}-7-methoxy-quinazoline 4-[(3-Chlor-4-fluor-phenyl)amino]-6-{trans-4-[(morpholine-4-yl)carbonylamino]-cyclohexane-1-yloxy}-7-methoxy-quinazoline 4-[(3-Chlor-4-fluor-phenyl)amino]-6-{trans-4-[(morpholine-4-yl)sulfonylamino]-cyclohexane-1-yloxy}-7-methoxy-quinazoline 4-[(3-Chlor-4-fluor-phenyl)amino]-6-(tetrahydropyran-4-yloxy)-7-(2-acetylamino-ethoxy)-quinazoline 4-[(3-Chlor-4-fluor-phenyl)amino]-6-(tetrahydropyran-4-yloxy)-7-(2-methansulfonylamino-ethoxy)-quinazoline 4-[(3-Chlor-4-fluor-phenyl)amino]-6-{1-[(piperidine-1-yl)carbonyl]-piperidine-4-yloxy}-7-methoxy-quinazoline 4-[(3-Chlor-4-fluor-phenyl)amino]-6-(1-aminocarbonylmethyl-piperidine-4-yloxy)-7-methoxy-quinazoline 4-[(3-Chlor-4-fluor-phenyl)amino]-6-(cis-4-{N-[(tetrahydropyran-4-yl)carbonyl]-N-methyl-amino}-cyclohexane-1-yloxy)-7-methoxy quinazoline 4-[(3-Chlor-4-fluor-phenyl)amino]-6-(cis-4-{N-[(morpholine-4-yl)carbonyl]-N-methyl-amino}-cyclohexane-1-yloxy)-7-methoxy-quinazoline 4-[(3-Chlor-4-fluor-phenyl)amino]-6-(cis-4-{N-[(morpholine-4-yl)sulfonyl]-N-methyl-amino}-cyclohexane-1-yloxy)-7-methoxy-quinazoline 4-[(3-Chlor-4-fluor-phenyl)amino]-6-(trans-4-ethansulfonylamino-cyclohexane-1-yloxy)-7-methoxy-quinazoline 4-[(3-Chlor-4-fluor-phenyl)amino]-6-(1-methansulfonyl-piperidine-4-yloxy)-7-ethoxy-quinazoline 4-[(3-Chlor-4-fluor-phenyl)amino]-6-(1-methansulfonyl-piperidine-4-yloxy)-7-(2-methoxy-ethoxy)-quinazoline 4-[(3-Chlor-4-fluor-phenyl)amino]-6-[1-(2-methoxy-acetyl)-piperidine-4-yloxy]-7-(2-methoxy-ethoxy)-quinazoline 4-[(3-Chlor-4-fluor-phenyl)amino]-6-(cis-4-acetylamino-cyclohexane-1-yloxy)-7-methoxy-quinazoline 4-[(3-Ethinyl-phenyl)amino]-6-[1-(tert-butyloxycarbonyl)-piperidine-4-yloxy]-7-methoxy-quinazoline 4-[(3-Ethinyl-phenyl)amino]-6-(tetrahydropyran-4-yloxy]-7-methoxy-quinazoline 4-[(3-Chlor-4-fluor-phenyl)amino]-6-(cis-4-{N-[(piperidine-1-yl)carbonyl]-N-methyl-amino}-cyclohexane-1-yloxy)-7-methoxy-quinazoline 4-[(3-Chlor-4-fluor-phenyl)amino]-6-(cis-4-{N-[(4-methyl-piperazine-1-yl)carbonyl]-N-methyl-amino}-cyclohexane-1-yloxy)-7-methoxy-quinazoline 4-[(3-Chlor-4-fluor-phenyl)amino]-6-{cis-4-[(morpholine-4-yl)carbonylamino]-cyclohexane-1-yloxy}-7-methoxy-quinazoline 4-[(3-Chlor-4-fluor-phenyl)amino]-6-{1-[2-(2-oxopyrrolidine-1-yl)ethyl]-piperidine-4-yloxy}-7-methoxy-quinazoline 4-[(3-Chlor-4-fluor-phenyl)amino]-6-{1-[(morpholine-4-yl)carbonyl]-piperidine-4-yloxy}-7-(2-methoxy-ethoxy)-quinazoline 4-[(3-Ethinyl-phenyl)amino]-6-(1-acetyl-piperidine-4-yloxy)-7-methoxy-quinazoline 4-[(3-Ethinyl-phenyl)amino]-6-(1-methyl-piperidine-4-yloxy)-7-methoxy-quinazoline 4-[(3-Ethinyl-phenyl)amino]-6-(1-methansulfonyl-piperidine-4-yloxy)-7-methoxy-quinazoline 4-[(3-Chlor-4-fluor-phenyl)amino]-6-(1-methyl-piperidine-4-yloxy)-7(2-methoxy-ethoxy)-quinazoline 4-[(3-Chlor-4-fluor-phenyl)amino]-6-(1-isopropyloxycarbonyl-piperidine-4-yloxy)-7-methoxy-quinazoline 4-[(3-Chlor-4-fluor-phenyl)amino]-6-(cis-4-methylamino-cyclohexane-1-yloxy)-7-methoxy-quinazoline 4-[(3-Chlor-4-fluor-phenyl)amino]-6-{cis-4-[N-(2-methoxy-acetyl)-N-methyl-amino]-cyclohexane-1-yloxy}-7-methoxy-quinazoline 4-[(3-Ethinyl-phenyl)amino]-6-(piperidine-4-yloxy)-7-methoxy-quinazoline 4-[(3-Ethinyl-phenyl)amino]-6-[1-(2-methoxy-acetyl)-piperidine-4-yloxy]-7-methoxy-quinazoline 4-[(3-Ethinyl-phenyl)amino]-6-{1-[(morpholine-4-yl)carbonyl]-piperidine-4-yloxy}-7-methoxy-quinazoline 4-[(3-Chlor-4-fluor-phenyl)amino]-6-{1-[(cis-2,6-dimethyl-morpholine-4-yl)carbonyl]-piperidine-4-yloxy}-7-methoxy-quinazoline 4-[(3-Chlor-4-fluor-phenyl)amino]-6-{1-[(2-methyl-morpholine-4-yl)carbonyl]-piperidine-4-yloxy}-7-methoxy-quinazoline 4-[(3-Chlor-4-fluor-phenyl)amino]-6-{1-[(S,S)-(2-oxa-5-aza-bicyclo[2.2.1]hept-5-yl)carbonyl]-piperidine-4-yloxy}-7-methoxy-quinazoline 4-[(3-Chlor-4-fluor-phenyl)amino]-6-{1-[(N-methyl-N-2-methoxyethyl-amino)carbonyl]-piperidine-4-yloxy}-7-methoxy-quinazoline 4-[(3-Chlor-4-fluor-phenyl)amino]-6-(1-ethyl-piperidine-4-yloxy)-7-methoxy-quinazoline 4-[(3-Chlor-4-fluor-phenyl)amino]-6-{1-[(2-methoxyethyl)carbonyl]-piperidine-4-yloxy}-7-methoxy-quinazoline 4-[(3-Chlor-4-fluor-phenyl)amino]-6-{1-[(3-methoxypropyl-amino)-carbonyl]-piperidine-4-yloxy}-7-methoxy-quinazoline 4-[(3-Chlor-4-fluor-phenyl)amino]-6-[cis-4-(N-methansulfonyl-N-methyl-amino)-cyclohexane-1-yloxy]-7-methoxy-quinazoline 4-[(3-Chlor-4-fluor-phenyl)amino]-6-[cis-4-(N-acetyl-N-methyl-amino)-cyclohexane-1-yloxy]-7-methoxy-quinazoline 4-[(3-Chlor-4-fluor-phenyl)amino]-6-(trans-4-methylamino-cyclohexane-1-yloxy)-7-methoxy-quinazoline 4-[(3-Chlor-4-fluor-phenyl)amino]-6-[trans-4-(N-methansulfonyl-N-methyl-amino)-cyclohexane-1-yloxy]-7-methoxy-quinazoline 4-[(3-Chlor-4-fluor-phenyl)amino]-6-(trans-4-dimethylamino-cyclohexane-1-yloxy)-7-methoxy-quinazoline 4-[(3-Chlor-4-fluor-phenyl)amino]-6-(trans-4-{N-[(morpholine-4-yl)carbonyl]-N-methyl-amino}-cyclohexane-1-yloxy)-7-methoxy-quinazoline 4-[(3-Chlor-4-fluor-phenyl)amino]-6-[2-(2,2-dimethyl-6-oxo-morpholine-4-yl)-ethoxy]-7-[(S)-(tetrahydrofuran-2-yl)methoxy]-quinazoline
4-[(3-Chlor-4-fluor-phenyl)amino]-6-(1-methansulfonyl-piperidine-4-yloxy)-7-methoxy-quinazoline
4-[(3-Chlor-4-fluor-phenyl)amino]-6-(1-cyano-piperidine-4-yloxy)-7-methoxy-quinazoline optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred SYK-inhibitors which may be mentioned include

2-[(2-aminoethyl)amino]-4-[(3-bromophenyl)amino]-5-pyrimidinecarboxamide;
2-[[7-(3,4-dimethoxyphenyl)imidazo[1,2-c]pyrimidine-5-yl]amino]-3-pyridinecarboxamide;
6-[[5-fluoro-2-[3,4,5-trimethoxyphenyl]amino]-4-pyrimidinyl]amino]-2,2-dimethyl-2H-pyrido[3,2-b]-1,4-oxazin-3 (4H)-one;
N-[3-bromo-7-(4-methoxyphenyl)-1,6-naphthyridine-5-yl]-1,3-propanediamine;
7-(4-methoxyphenyl)-N-methyl-1,6-naphthyridine-5-amine;
N-[7-(4-methoxyphenyl)-1,6-naphthyridine-5-yl]-1,3-propanediamine;
N-[7-(2-thienyl)-1,6-naphthyridine-5-yl-1,3-propanediamine;
N-[7-[4-(dimethylamino)phenyl]-1,6-naphthyridine-5-yl]-1,2-ethanediamine;
N-[7-(4-methoxyphenyl)-2-(trifluoromethyl)-1,6-naphthyridine-5-yl]-1,3-propanediamine;
N-[7-(4-methoxyphenyl)-3-phenyl-1,6-naphthyridine-5-yl]-1,3-propanediamine;
N-(7-phenyl-1,6-naphthyridine-5-yl)-1,3-propanediamine;
N-[7-(3-fluorophenyl)-1,6-naphthyridine-5-yl]-1,3-propanediamine;
N-[7-(3-chlorophenyl)-1,6-naphthyridine-5-yl]-1,3-propanediamine;
N-[7-[3-(trifluoromethoxy)phenyl]-1,6-naphthyridine-5-yl]-1,3-propanediamine;
N-[7-(4-fluorophenyl)-1,6-naphthyridine-5-yl]-1,3-propanediamine;
N-[7-(4-fluorophenyl)-1,6-naphthyridine-5-yl]-1,3-propanediamine;
N-[7-(4-chlorophenyl)-1,6-naphthyridine-5-yl]-1,3-propanediamine;
N-[7-(4'-methyl[1,1'-biphenyl]-4-yl)-1,6-naphthyridine-1,3-propanediamine;
N-[7-[4-(dimethylamino)phenyl]-1,6-naphthyridine-5-yl]-1,3-propanediamine;
N-[7-[4-(diethylamino)phenyl]-1,6-naphthyridine-5-yl]-1,3-propanediamine;
N-[7-[4-(4-morpholinyl)phenyl]-1,6-naphthyridine-5-yl]-1,3-propanediamine;
N-[7-[4-[[2-(dimethylamino)ethyl]methylamino]phenyl]-1,6-naphthyridine-5-yl]-1,3-propanediamine;
N-[7-(4-bromophenyl)-1,6-naphthyridine-5-yl]-1,3-propanediamine;
N-[7-(4-methylphenyl)-1,6-naphthyridine-5-yl]-1,3-propanediamine;
N-[7-[4-(methylthio)phenyl]-1,6-naphthyridine-5-yl]-1,3-propanediamine;
N-[7-[4-(1-methylethyl)phenyl]-1,6-naphthyridine-5-yl]-1,3-propanediamine;
7-[4-(dimethylamino)phenyl]-N-methyl-1,6-naphthyridine-5-amine;
7-[4-(dimethylamino)phenyl]-N,N-dimethyl-1,6-naphthyridine-5-amine;
N-[7-[4-(dimethylamino)phenyl]-1,6-naphthyridine-5-yl]-1,4-butanediamine;
N-[7-[4-(dimethylamino)phenyl]-1,6-naphthyridine-5-yl]-1,5-pentanediamine;
3-[[7-[4-(dimethylamino)phenyl]-1,6-naphthyridine-5-yl]oxy]-1-propanole;
4-[5-(4-aminobutoxy)-1,6-naphthyridine-7-yl]-N,N-dimethyl-benzenamine;
4-[[7-[4-(dimethylamino)phenyl]-1,6-naphthyridine-5-yl]amino]-1-butanole;
N-[7-[4-(dimethylamino)phenyl]-1,6-naphthyridine-5-yl]-N-methyl-1,3-propanediamine;
N-[7-[4-(dimethylamino)phenyl]-1,6-naphthyridine-5-yl]-N'-methyl-1,3-propanediamine;
N-[7-[4-(dimethylamino)phenyl]-1,6-naphthyridine-5-yl]-N,N'-dimethyl-1,3-propanediamine;
1-amino-3-[[7-[4-(dimethylamino)phenyl]-1,6-naphthyridine-5-yl]amino]-2-propanole;
N-[7-[4-(dimethylamino)phenyl]-1,6-naphthyridine-5-yl]-2,2-dimethyl-1,3-propanediamine;
7-[4-(dimethylamino)phenyl]-N-(3-pyridinylmethyl)-1,6-naphthyridine-5-amine;
N-[(2-aminophenyl)methyl]-7-[4-(dimethylamino)phenyl]-1,6-naphthyridine-5-amine;
N-[7-[6-(dimethylamino)[1,1'-biphenyl]-3-yl]-1,6-naphthyridine-5-yl]-1,3-propanediamine;
N-[7-[3-chloro-4-(diethylamino)phenyl]-1,6-naphthyridine-5-yl]-1,3-propanediamine;
N-[7-[4-(dimethylamino)-3-methoxyphenyl]-1,6-naphthyridine-5-yl]-1,3-propanediamine;
N-[7-[4-(diethylamino)phenyl]-3-methyl-1,6-naphthyridine-5-yl]-1,3-propanediamine;
N-[7-(3'-fluoro[1,1'-biphenyl]-3-yl)-1,6-naphthyridine-5-yl]-1,2-ethanediamin,
N-[7-(4-methoxyphenyl)-1,6-naphthyridine-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridine-5-yl]-1,6-naphthyridine-1,3-propanediamine;
N5-(3-aminopropyl)-7-(4-methoxyphenyl)-N2-(phenylmethyl)-2,5-diamine;
N-[7-(2-naphthalenyl)-1,6-naphthyridine-5-yl]-1,3-propanediamine;
N-[7-(2'-fluoro[1,1'-biphenyl]-4-yl)-1,6-naphthyridine-5-yl]-1,3-propanediamine;
N-[7-(3,4,5-trimethoxyphenyl)-1,6-naphthyridine-5-yl]-1,3-propanediamine;
N-[7-(3,4-dimethylphenyl)-1,6-naphthyridine-5-yl]-1,3-propanediamine;
1-amino-3-[[7-(2-naphthalenyl)-1,6-naphthyridine-5-yl]amino]-2-propanole;
1-amino-3-[[7-(2'-fluoro [1,1'-biphenyl]-4-yl)-1,6-naphthyridine-5-yl]amino]-2-propanole;
1-amino-3-[[7-(4'-methoxy[1,1'-biphenyl]-4-yl)-1,6-naphthyridine-5-yl]amino]-2-propanole;
1-amino-3-[[7-(3,4,5-trimethoxyphenyl)-1,6-naphthyridine-5-yl]amino]-2-propanole;
1-amino-3-[[7-(4-bromophenyl)-1,6-naphthyridine-5-yl]amino]-2-propanole;

N-[7-(4'-methoxy[1,1'-biphenyl]-4-yl)-1,6-naphthyridine-5-yl]-2,2-dimethyl-1,3-propanediamine;
1-[[7-[4-(dimethylamino)phenyl]-1,6-naphthyridine-5-yl]amino]-2-propanole;
2-[[2-[[7-[4-(dimethylamino)phenyl]-1,6-naphthyridine-5-yl]amino]ethyl]thio]-ethanole;
7-[4-(dimethylamino)phenyl]-N-(3-methyl-5-isoxazolyl)-1,6-naphthyridine-5-amine;
7-[4-(dimethylamino)phenyl]-N-4-pyrimidinyl-1,6-naphthyridine-5-amine;
N-[7-[4-(dimethylamino)phenyl]-1,6-naphthyridine-5-yl]-1,3-cyclohexane diamine;
N,N-dimethyl-4-[5(1-piperazinyl)-1,6-naphthyridine-7-yl]-benzenamine;
4-[5-(2-methoxyethoxy)-1,6-naphthyridine-7-yl]-N,N-dimethyl-benzenamine;
1-[7-[4-(dimethylamino)phenyl]-1,6-naphthyridine-5-yl]-4-piperidinole;
1-[7-[4-(dimethylamino)phenyl]-1,6-naphthyridine-5-yl]-3-pyrrolidinole;
7-[4-(dimethylamino)phenyl]-N-(2-furanylmethyl)-1,6-naphthyridine-5-amine;
7-[4-(dimethylamino)phenyl]-N-[3-(1H-imidazole-1-yl)propyl]-1,6-naphthyridine-5-amine;
1-[7-[4-(dimethylamino)phenyl]-1,6-naphthyridine-5-yl]-4-piperidine carboxamide;
1-[3-[[7-[4-(dimethylamino)phenyl]-1,6-naphthyridine-5-yl]amino]propyl]-2-pyrrolidinone;
N-[3'-[5-[(3-aminopropyl)amino]-1,6-naphthyridine-7-yl][1,1'-biphenyl]-3-yl]-acetamide;
N-[7-(4'-fluoro[1,1'-biphenyl]-4-yl)-1,6-naphthyridine-5-yl]-1,3-propanediamine;
N-[4'-[5-[(3-aminopropyl)amino]-1,6-naphthyridine-7-yl][1,1'-biphenyl]-3-yl]-acetamide;
N-[7-[4-(1,3-benzodioxol-5-yl)phenyl]-1,6-naphthyridine-5-yl]-1,3-propanediamine;
N-[7-[4-(2-thienyl)phenyl]-1,6-naphthyridine-5-yl]-1,3-propanediamine;
N-[7-[4-fluoro-3-(trifluoromethyl)phenyl]-1,6-naphthyridine-5-yl]-1,3-propanediamine;
N-[7-[4-(3-pyridinyl)phenyl]-1,6-naphthyridine-5-yl]-1,3-propanediamine;
N-[7-(1,3-benzodioxol-5-yl)-1,6-naphthyridine-5-yl]-1,3-propanediamine;
N-[7-(6-methoxy-2-naphthalenyl)-1,6-naphthyridine-5-yl]-1,3-propanediamine;
7-[4-(dimethylamino)phenyl]-N-(4-pyridinylmethyl)-1,6-naphthyridine-5-amine;
3-[[7-[4-(dimethylamino)phenyl]-1,6-naphthyridine-5-yl]methylamino]-propanenitrile;
7-[4-(dimethylamino)phenyl]-N-[1-(phenylmethyl)-4-piperidinyl]-1,6-naphthyridine-5-amine;
N-[7-[4-(dimethylamino)phenyl]-1,6-naphthyridine-5-yl]-1,2-cyclohexanediamin,
N-[7-[4-(dimethylamino)phenyl]-1,6-naphthyridine-5-yl]-1,2-Cyclohexanediamine, (1R,2S)-rel-.
N-[7-[4-(dimethylamino)phenyl]-1,6-naphthyridine-5-yl]-1,2-benzene dimethanamine;
N-[7-[4-(diethylamino)phenyl]-1,6-naphthyridine-5-yl]-1,4-butanediamine;
N-[7-[3',5'-bis(trifluoromethyl)[1,1'-biphenyl]-4-yl]-1,6-naphthyridine-5-yl]-,3-propanediamine;
N-[7-(3'-methoxy[1,1'-biphenyl]-4-yl)-1,6-naphthyridine-5-yl]-1,3-propanediamine;
N-[7-(3'-fluoro [1,1'-biphenyl]-4-yl)-1,6-naphthyridine-5-yl]-1,3-propanediamine;
4-[[7-[4-(dimethylamino)phenyl]-1,6-naphthyridine-5-yl]oxy]-1-butanole;
N-[7-[4-(dimethylamino)phenyl]-1,6-naphthyridine-5-yl]-1,4-cyclohexanediamine;
7-[4-(dimethylamino)phenyl]-N-(2,2,6,6-tetramethyl-4-piperidinyl)-1,6-naphthyridine-5-amine;
N-[7-[3-bromo-4-(dimethylamino)phenyl]-1,6-naphthyridine-5-yl]-1,3-propanediamine;
N-[7-(1-methyl-1H-indole-5-yl)-1,6-naphthyridine-5-yl]-1,3-propanediamine;
N-[7-[3-(trifluoromethyl)phenyl]-1,6-naphthyridine-5-yl]-1,3-propanediamine;
N-[7-[4-(trifluoromethyl)phenyl]-1,6-naphthyridine-5-yl]-1,3-propanediamine;
N-[7-(3-bromo-4-methoxyphenyl)-1,6-naphthyridine-5-yl]-1,3-propanediamine;
N-[7-[4-[[3-(dimethylamino)propyl]methylamino]phenyl]-1,6-naphthyridine-5-yl]-1,4-cyclohexanediamine;
N-[7-[4-[[2-(dimethylamino)ethyl]methylamino]phenyl]-1,6-naphthyridine-5-yl]-1,4-cyclohexanediamine;
N-[7-[4-(dimethylamino)-3-methoxyphenyl]-1,6-naphthyridine-5-yl]-1,4-cyclohexanediamine;
N-[7-[4-(4-morpholinyl)phenyl]-1,6-naphthyridine-5-yl]-1,4-cyclohexanediamine;
N-[7-[3-bromo-4-(4-morpholinyl)phenyl]-1,6-naphthyridine-5-yl]-1,4-cyclohexanediamine;
4-[[7-[4-[[2-(dimethylamino)ethyl]methylamino]phenyl]-1,6-naphthyridine-5-yl]oxy]-cyclohexanole;
N-[7-[3-bromo-4-(4-morpholinyl)phenyl]-1,6-naphthyridine-5-yl]-1,3-propanediamine;
N,N-dimethyl-4-[5-(4-methyl-1-piperazinyl)-1,6-naphthyridine-7-yl]-benzenamine;
4-[[7-[4-[[3-(dimethylamino)propyl]methylamino]phenyl]-1,6-naphthyridine-5-yl]oxy]-cyclohexanole;
N-[7-[4-[[2-(dimethylamino)ethyl]methylamino]phenyl]-1,6-naphthyridine-5-yl]-1,4-butanediamin;
[3-[[5-[(3-aminopropyl)amino]-7-(4-methoxyphenyl)-1,6-naphthyridine-2-yl]amino]propyl]-carbamic acid-1,1-dimethylethyl ester, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred antiallergic agents which may be mentioned include Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Olopatadine, Desloratidine and Meclozine, optionally in racemic form, as enantiomers, diastereomeres or as pharmacologically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred MAP kinase inhibitors which may be mentioned include
Bentamapimod (AS-602801)
Doramapimod (BIRB-796),
5-Carbamoylindole (SD-169),
6-[(aminocarbonyl)(2,6-difluorophenyl)amino]-2-(2,4-difluorophenyl)-3-pyridine carboxamide (VX-702),
alpha-[2-[[2-(3-pyridinyl)ethyl]amino]-4-pyrimidinyl]-2-benzothiazole acetonitrile (AS-601245),
9,12-Epoxy-1H-diindolo[1,2,3-fg:3',2',1'-kl]pyrrolo[3,4-i][1,6]benzodiazocine-10-Carboxylic acid (CEP-1347),
4-[3-(4-chlorophenyl)-5-(1-methyl-4-piperidinyl)-1H-pyrazole-4-yl]-pyrimidine (SC-409),
optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Indications

The present invention is directed to compounds of general formula 1 which are useful in the prevention and/or treatment of a disease and/or condition wherein the activity of CXCR2 antagonism is of therapeutic benefit, including but not limited to the treatment and/or prevention of inflammatory diseases. Examples include respiratory or gastrointestinal diseases or complaints, inflammatory diseases of the joints, skin, or eyes, cancers and also diseases of the peripheral or central nervous system.

The compounds of general formula 1 are useful for the prevention and/or treatment of diseases of the airways and of the lung which are accompanied by increased mucus production, inflammations, and/or obstructive diseases of the airways. Examples include acute, allergic, or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyper-reactive airways, infections, bronchitis, pneumonitis, paediatric asthma, bronchiectases, pulmonary fibrosis, ARDS (acute adult respiratory distress syndrome), bronchial edema, pulmonary edema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis, or mucoviscidosis, or alpha1-antitrypsin deficiency.

Accordingly, the present invention relates to a compound of general formula 1 as a medicament.

Furthermore, the present invention relates to the use of a compound of general formula 1 for the treatment and/or prevention of a disease and/or condition wherein the activity of CXCR2 antagonism is of therapeutic benefit.

Furthermore, the present invention relates to the use of a compound of general formula 1 for the treatment and/or prevention of inflammatory diseases. Examples include respiratory or gastrointestinal diseases or complaints, inflammatory diseases of the joints, skin, or eyes, cancers and also diseases of the peripheral or central nervous system.

Furthermore, the present invention relates to the use of a compound of general formula 1 for the treatment and/or prevention of diseases of the airways and of the lung which are accompanied by increased mucus production, inflammations, and/or obstructive diseases of the airways. Examples include acute, allergic, or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyper-reactive airways, infections bronchitis or pneumonitis, paediatric asthma, bronchiectases, pulmonary fibrosis, ARDS (acute adult respiratory distress syndrome), bronchial edema, pulmonary edema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis, or mucoviscidosis, or alphal-antitrypsin deficiency.

In a further aspect of the present invention the present invention relates to methods for the treatment or prevention of above mentioned diseases and conditions, which method comprises the administration of an effective amount of a compound of general formula 1 to a human being.

The dose range of the compounds of general formula 1 applicable per day is usually from 0.1 mg to 500 mg, preferably from 1 mg to 50 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Formulations

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised in that they contain one or more compounds of formula I according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula I are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-1-solvents, stabilisers, surfactants, antioxidants, lubricants and pH adjusters. All these ingredients are known in the art.

Propellant-Free Inhalable Solutions

The compounds of formula I according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a pteridine and one or more combination partners selected from those described above.

What we claim:

1. A compound of the formula (1),

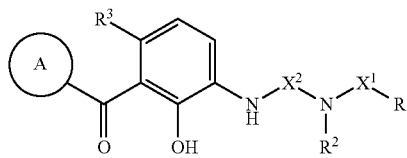

(1)

wherein $R^1$ is an 5-10 membered aromatic, heteroaromatic, non aromatic cyclic or heterocyclic, single or condensed multiring system, optionally substituted by 1-4 residues selected from halogen or $C_{1-6}$-alkyl, optionally substituted with one or more F atoms;

$X^1$ is absent or methylene optionally substituted with $C_{1-5}$-alkyl, said alkyl optionally substituted with one or more F atoms, $C_{1-4}$-alkyl-O—, CN or $C_{3-8}$-cycloalkyl, wherein optionally one carbon atom is replaced by an O;

$R^2$ is H;

$X^2$ is

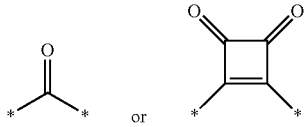

$R^3$ is H, halogen, CN, $C_{1-6}$-alkyl, optionally substituted with one or more F atoms;

A is a N-linked 7-13 membered non-aromatic bicyclic system in which the two rings are either condensed to each other or joined in a spiro system and in which if present one CH group can be optionally replaced by N and one, two three or four $CH_2$ groups in said system are optionally replaced by NH, CO, O, S, SO, $SO_2$, and one, two three or four positions on said ring system are optionally substituted with one or more F atoms, $C_{1-6}$-alkyl, optionally substituted with one or more F atoms, $C_{1-6}$-alkyl-OC(O)—, HO—$C_{1-6}$-alkyl- or $C_{1-6}$-alkyl-O—$C_{1-6}$-alkyl and in which optionally two of these substituents are joined to form an additional ring or a pharmaceutically acceptable salt thereof.

2. A compound of the formula (1), according to claim 1, wherein $R^1$ is selected from the group consisting of phenyl, furanyl, optionally substituted by one or two residues selected from halogen or $C_{1-6}$-alkyl, optionally substituted with one or more F atoms;

$X^1$ is absent or $C_{1-6}$-alkyl; said alkyl optionally substituted with one or more F atoms;

$R^2$ is H;

$X^2$ is

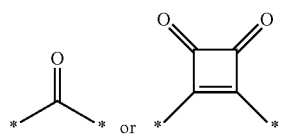

$R^3$ is H, halogen, CN, $C_{1-6}$-alkyl, optionally substituted with one or more F atoms;

A is a N-linked four-, five- or six membered non-aromatic ring, with an additional condensed or spiro attached four-, five- or six membered ring, forming a bicyclic heterocyclic ring system, wherein if present one CH group is optionally replaced by N; and one, two or three $CH_2$ groups are optionally replaced by $C_{1-6}$-alkyl-CH—, ($C_{1-6}$-alkyl$_2$-C—, $C_{1-6}$-alkyl-OC(O)CH—, CO, O, NH, ($C_{1-6}$-alkyl)N—, $SO_2$, wherein $C_{1-6}$-alkyl groups are optionally substituted by OH or a pharmaceutically acceptable salt thereof.

3. A compound of the formula (1), according to claim 1, wherein $R^1$ is selected from the group consisting of phenyl, furanyl, optionally substituted by one or two residues selected from halogen or $C_{1-4}$-alkyl, optionally substituted with one or more F atoms;

$X^1$ is absent or a branched or unbranched $C_{1-4}$-alkyl; said alkyl optionally substituted with one or more F atoms;

$R^2$ is H;

$X^2$ is

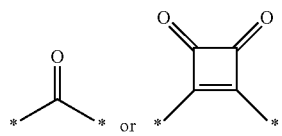

$R^3$ is H, halogen, CN, $C_{1-4}$-alkyl, optionally subsituted with F;

A is a N-linked four-, five- or six membered non-aromatic ring, with an additional condensed or spiro attached four-, five- or six membered ring, forming a bicyclic heterocyclic ring system, wherein if present one CH group is optionally replaced by N; and one, two or three $CH_2$ groups are optionally replaced by $C_{1-6}$-alkyl-CH—, ($C_{1-6}$-alkyl$_2$-C—, $C_{1-6}$-alkyl-OC(O)CH—, CO, O, NH, ($C_{1-6}$-alkyl)N—, $SO_2$, wherein $C_{1-6}$-alkyl groups are optionally substituted by OH.

4. A compound of the formula (1), according to claim 1, wherein $R^1$ is selected from the group consisting of phenyl, furanyl, optionally substituted by one or two residues selected from halogen or $C_{1-4}$-alkyl, optionally substituted with one or more F atoms;

$X^1$ is absent or a branched or unbranched $C_{1-4}$-alkyl; said alkyl optionally substituted with one or more F atoms;
$R^2$ is H;
$X^2$ is

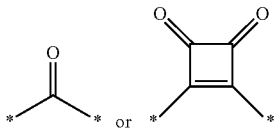

$R^3$ is H, halogen, CN, $C_{1-4}$-alkyl, optionally subsituted with F;
A is a bicyclic heterocyclic system of the formula

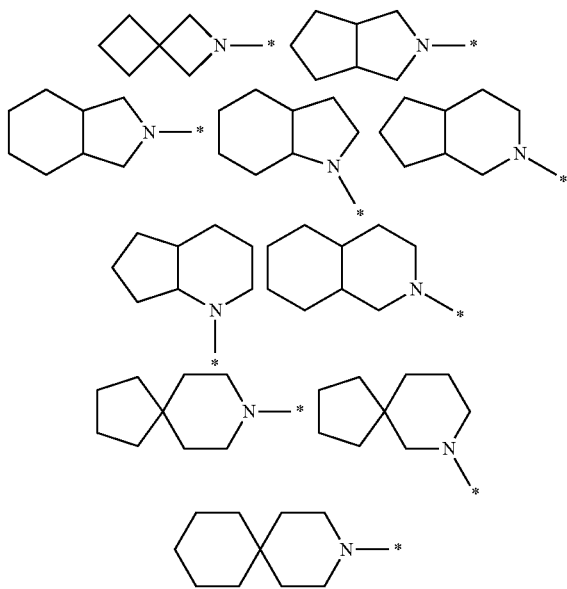

wherein
   if present one CH group is optionally replaced by N; and
   one, two or three $CH_2$ groups are optionally replaced by $C_{1-6}$-alkyl-CH—, $(C_{1-6}$-alkyl$_2$-C—, $C_{1-6}$-alkyl-OC(O)CH—, CO, O, NH, $(C_{1-6}$-alkyl)N—, $SO_2$, wherein $C_{1-6}$-alkyl groups are optionally substituted by OH
or a pharmaceutically acceptable salt thereof.

5. A compound of the formula (1), according to claim 1, wherein
$R^1$ is selected from the group consisting of phenyl, furanyl, optionally substituted by one or two residues selected from Me, $CF_3$, F, Cl;
$X^1$ is absent or a branched or unbranched $C_{1-4}$-alkyl; said alkyl optionally substituted with one or more F atoms;
$R^2$ is H;
$X^2$ is

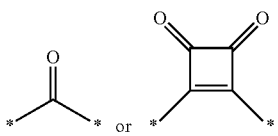

$R^3$ is H, Cl, CN, $CF_3$;
A is a bicyclic heterocyclic system of the formula

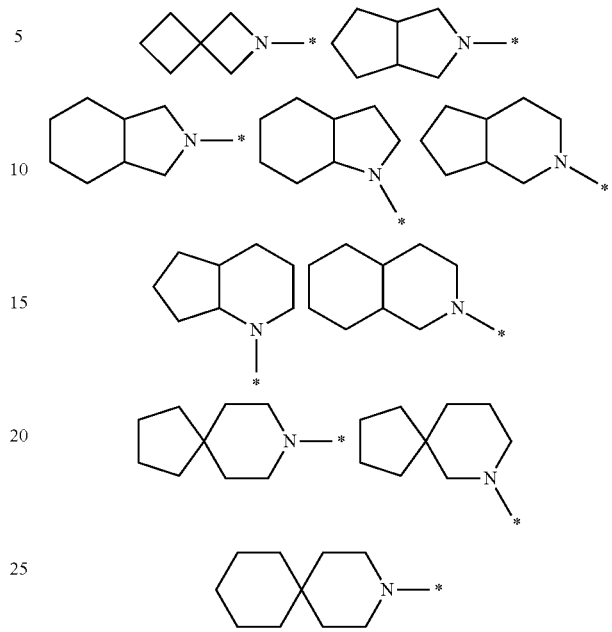

wherein
   if present one CH group is optionally replaced by N; and
   one, two or three $CH_2$ groups are optionally replaced by $CHMe$, $CMe_2$, $CHCH_2OH$, $CHCOOMe$, CO, O, NH, NMe, $SO_2$
or a pharmaceutically acceptable salt thereof.

6. A compound of the formula (1), according to claim 1, wherein
$R^1$ is selected from the group consisting of phenyl, furanyl, optionally substituted by one or two residues selected from Me, $CF_3$, F, Cl;
$X^1$ is absent or a branched or unbranched $C_{1-4}$-alkyl; said alkyl optionally substituted with one or more F atoms;
$R^2$ is H;
$X^2$ is

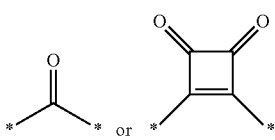

$R^3$ is H, Cl, CN, $CF_3$;
A is a bicyclic heterocyclic system selected from the group consisting of

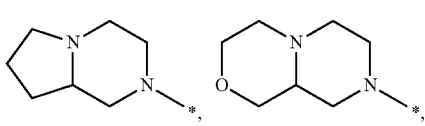

-continued

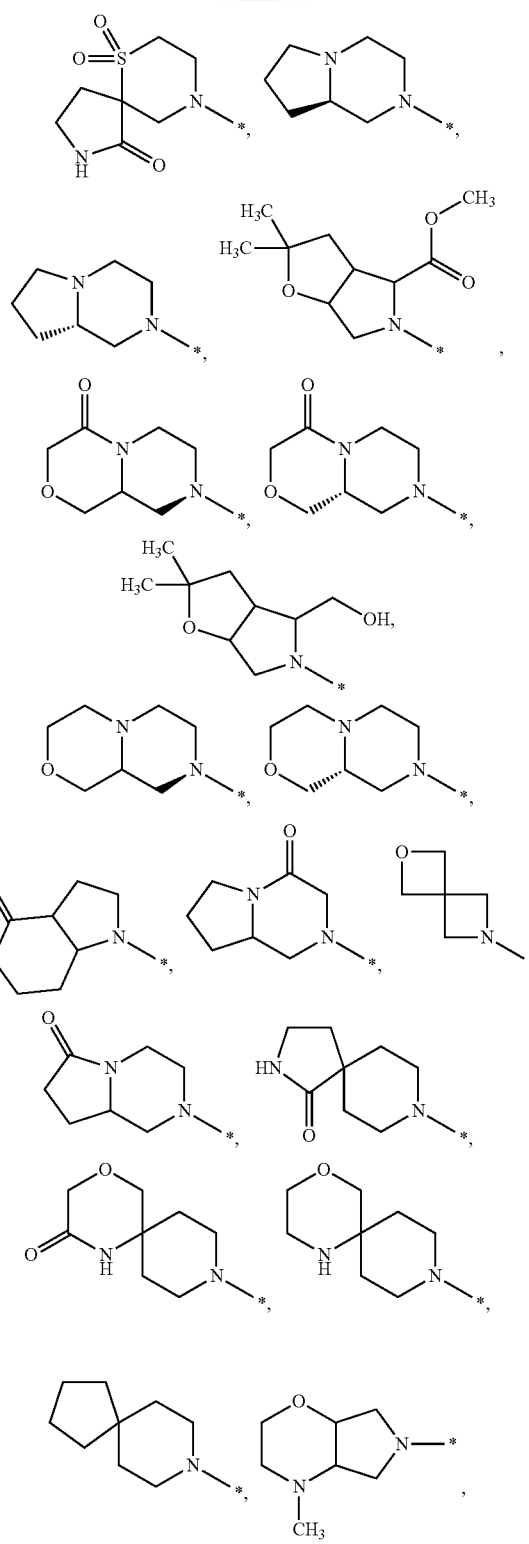

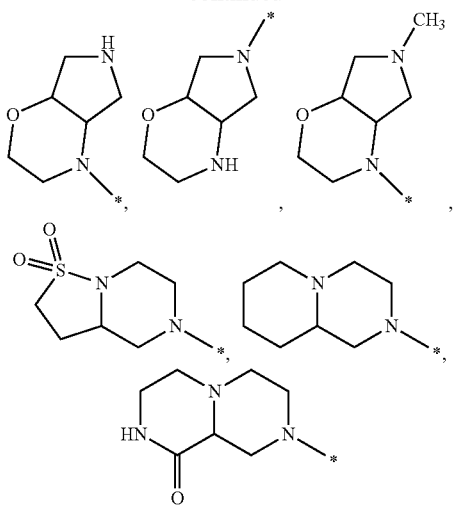

or a pharmaceutically acceptable salt thereof.

7. A compound of the formula (1), according claim 1, wherein $R^1$ is selected from the group consisting of phenyl, furanyl, optionally substituted by one or two residues selected from Me, $CF_3$, F, Cl;

$X^1$ is absent or a branched or unbranched $C_{1-4}$-alkyl; said alkyl optionally substituted with one or more F atoms;

$R^2$ is H;

$X^2$ is

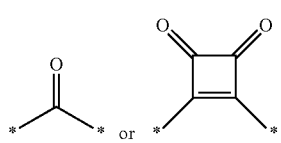

$R^3$ is H, Cl, CN, $CF_3$;

A is a bicyclic heterocyclic system of the formula

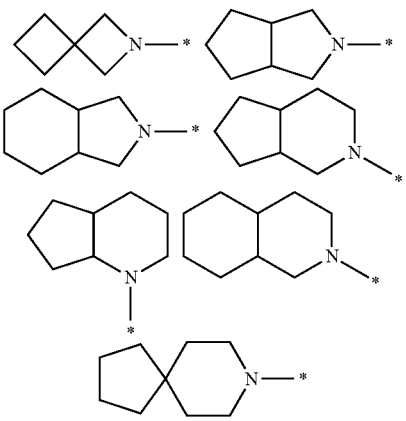

wherein
  if present one CH group is optionally replaced by N; and
  one, two or three $CH_2$ groups are optionally replaced by $CHMe$, $CMe_2$, $CHCH_2OH$, $CHCOOMe$, $CO$, $O$, $NH$, $NMe$
or a pharmaceutically acceptable salt thereof.

8. A compound of the formula (1), according to claim 1, wherein

R¹ is selected from the group consisting of phenyl, furanyl, optionally substituted by one or two residues selected from Me, CF₃, F, Cl;

X¹ is absent or a branched or unbranched C₁₋₄-alkyl; said alkyl optionally substituted with one or more F atoms;

R² is H;

X² is

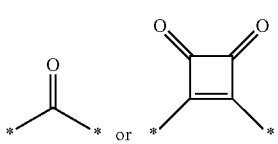

R³ is H;

A is a bicyclic heterocyclic system selected from the group consisting of

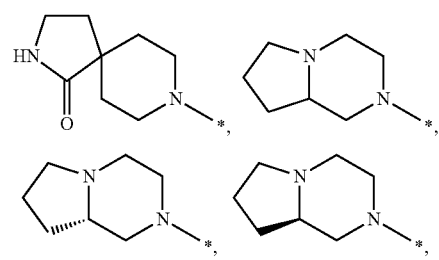

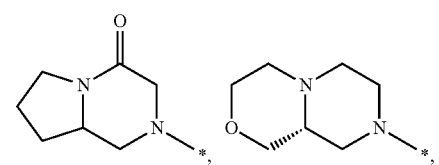

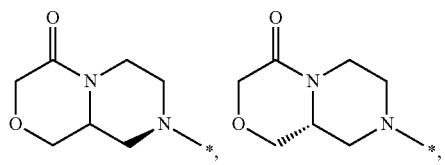

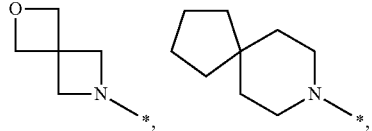

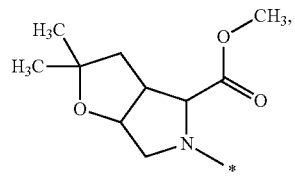

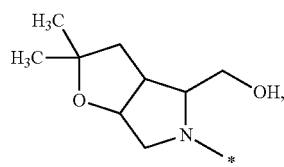

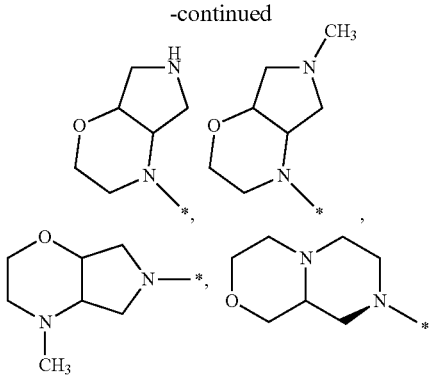

or a pharmaceutically acceptable salt thereof.

9. A compound of the formula (1), according to claim 1, wherein

R¹ is selected from the group consisting of phenyl, furanyl, optionally substituted by one or two residues selected from Me, CF₃, F, Cl;

X¹ is absent or a branched or unbranched C₁₋₄-alkyl; said alkyl optionally substituted with one or more F atoms;

R² is H;

X² is

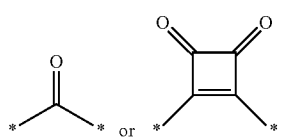

R³ is H, Cl, CN, CF₃;

A is a bicyclic heterocyclic system of the formula

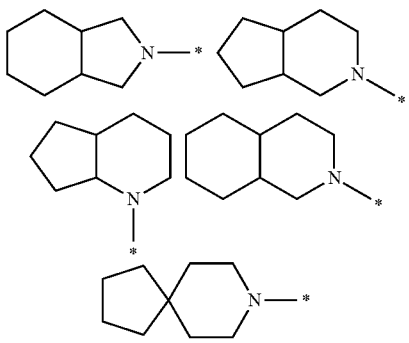

wherein
one CH group is optionally replaced by N; and
one, two or three CH₂ groups are optionally replaced by CHMe, CMe₂, CO, O, NH, NMe
or a pharmaceutically acceptable salt thereof.

10. A compound of the formula (1), according to claim 1, wherein

R¹ is selected from the group consisting of phenyl, furanyl, optionally substituted by one or two residues selected from Me, CF₃, F, Cl;

X¹ is absent or a branched or unbranched C₁₋₄-alkyl; said alkyl optionally substituted with one or more F atoms;

R² is H;

$X^2$ is
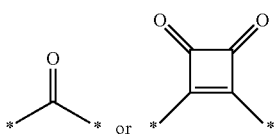
$R^3$ is H;
A is a bicyclic heterocyclic system selected from the group consisting of
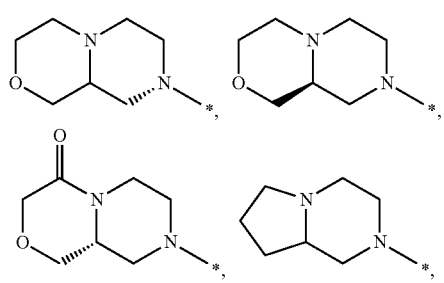
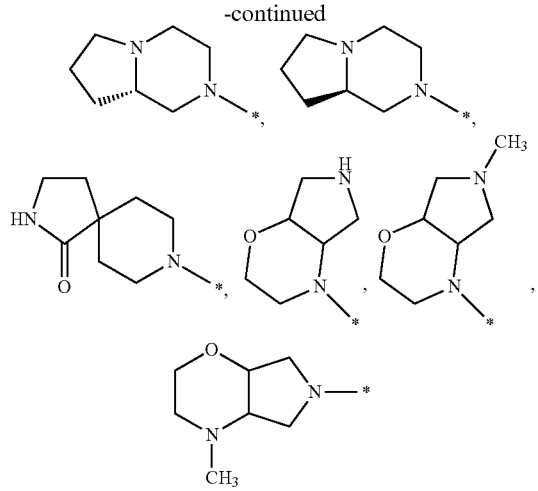
or a pharmaceutically acceptable salt thereof.
11. A pharmaceutical composition comprising a compound of the formula (1), according claim 1 and a pharmaceutically acceptable carrier.
* * * * *